US006297333B1

(12) United States Patent
Imuta et al.

(10) Patent No.: US 6,297,333 B1
(45) Date of Patent: Oct. 2, 2001

(54) OLEFIN POLYMERIZATION CATALYST, PROCESS FOR PREPARING OLEFIN POLYMER, AND OLEFIN POLYMER

(75) Inventors: Junichi Imuta; Masayasu Yoshida; Yasushi Tohi, all of Yamaguchi (JP)

(73) Assignee: Mitsui Chemicals Inc, Tokyo (JP)

( * ) Notice: Subject to any disclaimer, the term of this patent is extended or adjusted under 35 U.S.C. 154(b) by 0 days.

(21) Appl. No.: 09/315,268

(22) Filed: May 20, 1999

Related U.S. Application Data

(62) Division of application No. 08/683,068, filed on Jul. 16, 1996, now Pat. No. 6,004,897.

(30) Foreign Application Priority Data

| Jul. 17, 1995 | (JP) | 7-180178 |
| Jul. 17, 1995 | (JP) | 7-180179 |
| Nov. 17, 1995 | (JP) | 7-300323 |
| Nov. 17, 1995 | (JP) | 7-300324 |
| Dec. 28, 1995 | (JP) | 7-344258 |
| Dec. 28, 1995 | (JP) | 7-344259 |

(51) Int. Cl.$^7$ ..................................................... C08F 4/42

(52) U.S. Cl. ........................ 526/160; 526/127; 526/129; 526/131; 526/943; 526/348.2; 526/348; 502/103; 502/120; 502/152

(58) Field of Search ................................ 526/127, 129, 526/131, 160, 943, 348.2, 348; 502/103, 120, 152

(56) References Cited

U.S. PATENT DOCUMENTS

| 5,391,789 | * | 2/1995 | Rohrmann ............................... 556/11 |
| 5,399,636 |   | 3/1995 | Alt et al. . |
| 5,455,366 |   | 10/1995 | Rohrmann et al. . |
| 5,539,069 |   | 7/1996 | Tsutsui et al. . |
| 5,770,664 | * | 2/1995 | Okumura et al. ..................... 526/127 |

FOREIGN PATENT DOCUMENTS

| 0485822 | 5/1992 | (EP) . |
| 0524624 | 1/1993 | (EP) . |
| 0528287 | 2/1993 | (EP) . |
| 0549900 | 7/1993 | (EP) . |
| 0576970 | 1/1994 | (EP) . |
| 0632066 | 1/1995 | (EP) . |
| 0693497 | 1/1996 | (EP) . |
| 0707016 | 4/1996 | (EP) . |

OTHER PUBLICATIONS

Australian Patent Abstract AU–A–41491/93 (Jan. 6, 1994).

S. Jungling, et al. "The Role of Dormant Sites In . . . ", Macromolecular Symposia, vol. 97, pp. 205–216 (Jul. 1995).

* cited by examiner

Primary Examiner—David W. Wu
Assistant Examiner—Ling-Siu Choi

(57) ABSTRACT

The olefin polymerization catalyst of the invention is formed from a Group IVB transition metal compound represented by the following formula (I) and an organoaluminum oxy-compound or a compound which reacts with the transition metal compound to form an ion pair. In the olefin polymerization process of the invention using this catalyst or a catalyst formed from a Group IVB transition metal compound represented by the following formula (II) and an

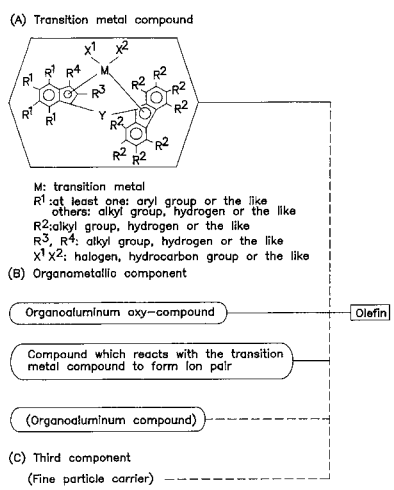

organoaluminum oxy-compound or a compound which reacts with the transition metal compound to form an ion pair, an olefin (co)polymer having a high molecular weight can be obtained with high polymerization activities, and besides an olefin copolymer having a high comonomer content can be obtained even if a comonomer is used in a small amount,

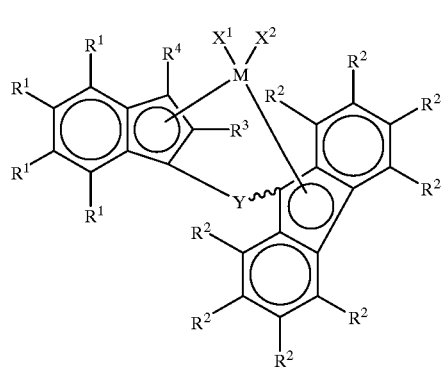

(I)

-continued

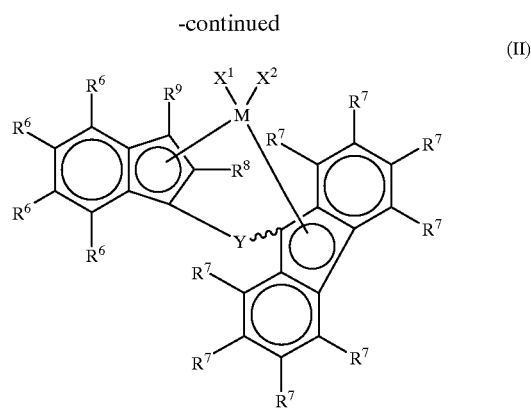

(II)

wherein, M is a transition metal of Group IVB, at least one of $R^1$ is an aryl group and the remainder is hydrogen or the like, $R^2$ is hydrogen, an alkyl group or the like, $R^3$ and $R^4$ are each hydrogen, an alkyl group or the like, $R^6$ is hydrogen, an alkyl group or the like, $R^7$ is hydrogen, an alkyl group or the like, any one of $R^8$ and $R^9$ is an alkyl group, and $X^1$ and $X^2$ are each halogen, a hydrocarbon group or the like.

11 Claims, 2 Drawing Sheets

(A) Transition metal compound

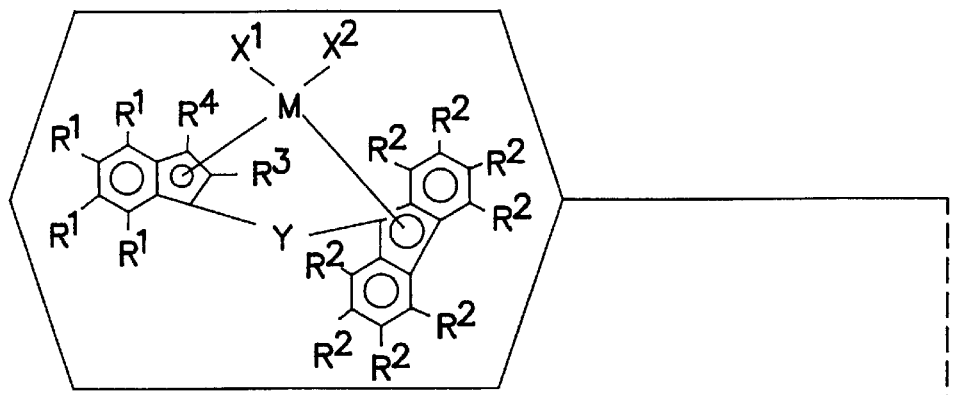

M: transition metal
$R^1$: at least one: aryl group or the like
   others: alkyl group, hydrogen or the like
$R^2$: alkyl group, hydrogen or the like
$R^3$, $R^4$: alkyl group, hydrogen or the like
$X^1 X^2$: halogen, hydrocarbon group or the like (B) Organometallic component ( Organoaluminum oxy-compound ) ─────── Olefin ( Compound which reacts with the transition metal compound to form ion pair )

( Organoaluminum compound )

(C) Third component
    (Fine particle carrier)

FIG. 1

(A) Transition metal compound

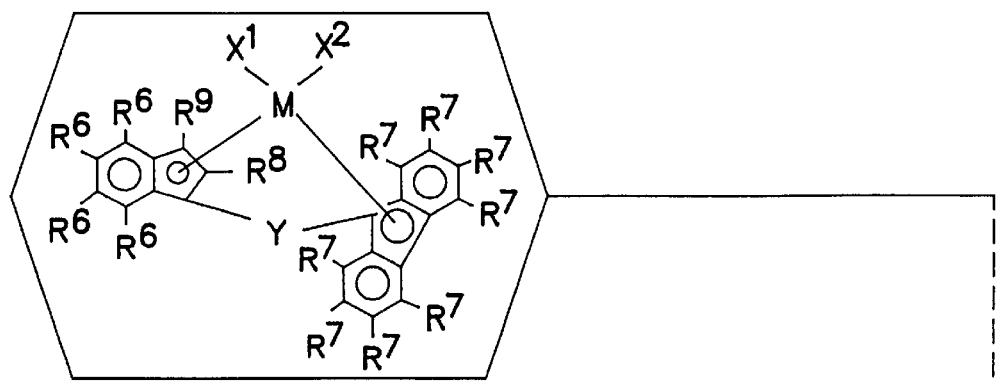

M: transition metal
$R^6$: hydrogen, alkyl group or the like
$R^7$: alkyl group, hydrogen or the like
$R^8$, $R^9$: one: alkyl group of 1 to 5 carbon atoms
the other: hydrogen, alkyl group or the like
$X^1 X^2$: halogen, hydrocarbon group or the like (B) Organometallic component ( Organoaluminum oxy-compound )

( Compound which reacts with the transition metal compound to form ion pair )

( (Organoaluminum compound) )

(C) Third component
(Fine particle carrier)

FIG. 2

OLEFIN POLYMERIZATION CATALYST, PROCESS FOR PREPARING OLEFIN POLYMER, AND OLEFIN POLYMER

CROSS-REFERENCE TO RELATED APPLICATIONS

This application is a division of application Ser. No. 08/683,068, filed Jul. 16, 1996 U.S. Pat. No. 6,004,897.

FIELD OF THE INVENTION

The present invention relates to olefin polymerization catalysts, processes for preparing olefin polymers, and olefin polymers. More particularly, the invention relates to olefin polymerization catalysts which are capable for giving olefin (co)polymers of high molecular weight with extremely high polymerization activities and olefin copolymers having a high comonomer content even if a comonomer is used in a small amount, and also relates to processes for preparing olefin polymers by which olefin (co)polymers of high molecular weight can be obtained with extremely high polymerization activities and olefin copolymers having a high. comonomer content can be obtained even if a comonomer is used in a small amount, and to olefin polymers obtained by the processes.

BACKGROUND OF THE INVENTION

For preparing olefin (co)polymers such as an ethylene homopolymer, an ethylene-α-olefin copolymer, a propylene homopolymer and a propylene-α-olefin copolymer, processes of polymerizing olefins in the presence of a Ziegler catalyst comprising a titanium compound and an organoaluminum compound or a vanadium catalyst comprising a vanadium compound and an organoaluminum compound are conventionally known.

Also known are processes of polymerizing olefins in the presence of a metallocene catalyst comprising a transition metal compound such as zirconocene and an organoaluminum oxy compound (aluminoxane), and it is known that the use of the metallocene catalyst makes it possible to polymerize olefins with high activities and to obtain olefin (copolymers of narrow molecular weight distribution and narrow composition distribution.

Recently, the requirements for properties of the olefin (co)polymers have varied, and olefin (co)polymers of various properties have been desired. Moreover, development of a transition metal compound catalyst component capable of producing such olefin (co)polymers is also desired.

Under the circumstances, Japanese Laid-Open Publication No. 345793/1993 discloses a novel transition metal compound having an indenyl group and a fluorenyl group as ligands serving as an olefin polymerization catalyst component. However, in polymerization of an olefin using this transition metal compound as a catalyst component, the polymerization activity is low so that only a polymer of low molecular weight is produced.

EP0707016A also discloses a transition metal compound having an indenyl group and a fluorenyl group and a catalyst in which a specific aryl group such as a phenyl group or a naphthyl group is introduced into a specific position (4-position) of the indenyl group. However, in polymerization of an olefin using this transition metal compound as a catalyst component, the polymerization activity is also low so that only a polymer of low molecular weight is produced, The present inventors have studied under such circumstances as mentioned above, and as a result they have found that by the use of a compound wherein a specific substituent is introduced at the specific position of the indenyl group in the above-mentioned transition metal compound, an olefin (co)polymer of high molecular weight can be prepared with high polymerization activities and an olefin copolymer of high comonomer content can be obtained. Further, the present inventors have also sound that an olefin (co)polymer of high molecular weight can be prepared with much higher polymerization activities and an olefin copolymer of much higher comonomer consent can be obtained by introducing a specific substituent at the specific position of the fluorenyl group of the characteristic transition metal compound. Thus, the present invention has been accomplished.

OBJECT OF THE INVENTION

It is an object of the present invention to provide an olefin polymerization catalyst which is capable for giving an olefin (co)polymer having a high molecular weight with extremely high polymerization activities and an olefin copolymer having a high comonomer content. It is another object of the invention to provide a process for preparing an olefin polymer using the catalyst and an olefin polymer obtained by the process.

SUMMARY OF THE INVENTION

The olefin polymerization catalyst according to the present invention comprises:

(A-1) a Group IVB transition metal compound represented by the following formula (I), (B) (B-1) an organoaluminum oxy-compound, and/or
(B-2) a compound which reacts with the transition metal compound (A-1) to form an ion pair,
and optionally (C) an organoaluminum compound;

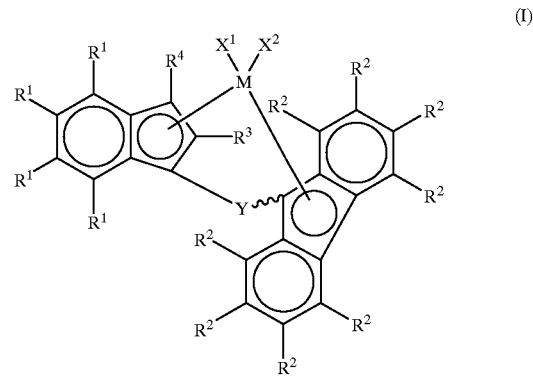

wherein M is a transition metal atom of Group IVB of the periodic table;

$R^1$'s may be the same as or different from each other, at least one Of them is an aryl group of 11 to 20 carbon atoms, an arylalkyl group of 12 to 40 carbon atoms, an arylalkenyl group of 13 to 40 carbon atoms or an alkylaryl group of 12 to 40 carbon atoms, or at least two adjacent groups among groups indicated by $R^1$ form an aromatic ring or an aliphatic ring together with carbon atoms to which said at least two groups are bonded (in this case the rings formed by $R^1$ have 4 to 20 carbon atoms as a whole), and the remainder of $R^1$ is hydrogen atom, a halogen atom or an alkyl group of 1 to 10 carbon atoms, $R^2$'s may be the same as or different from each other, 10 they are each hydrogen atom, a halogen atom, an alkyl group of 1 to 10 carbon atoms, an aryl group of 6 to 20 carbon atoms, an alkenyl group of 2 to 10 carbon atoms, an arylalkyl group of 7 to 40 carbon atoms, an arylalkenyl group of 8 to 40 carbon atoms, an alkylaryl group of 7 to 40 carbon atoms, a silicon-containing group, an oxygen-containing group, a sulfur-containing group, a nitrogen-containing group or a phosphorus-containing group, and at least two adjacent groups among groups indicated by $R^2$ may form an aromatic ring or an aliphatic ring together with carbon atoms to which said at least two groups are bonded (in this case the rings formed by $R^2$ have 4 to 20 carbon atoms as a whole including carbon atoms to which the $R^2$ groups are bonded, and the remainder of $R^2$ is hydrogen atom, a halogen atom or an alkyl group on I to 1i0 carbon atoms), $R^1$ and $R^2$ may be the same as or different from each other, $R^3$ and $R^4$ may be the same as or different from each other, and are each hydrogen atom, a halogen atom, an alkyl group of 1 to 10 carbon atoms, an aryl group of 6 to 20 carbon atoms, an alkenyl group of 2 to 10 carbon atoms, an arylalkyl group of 7 to 40 carbon atoms, an arylalkenyl group of 8 to 40 carbon atoms, an alkylaryl group of 7 to 40 carbon atoms, a silicon-containing group, an oxygen-containing group, a sulfur-containing group, a nitrogen-containing group or a phosphorus-containing group, $X^1$ and $X^2$ may be the same as or different from each other, and are each hydrogen atom, a halogen atom, a hydrocarbon group of 1 to 20 carbon atoms, a halogenated hydrocarbon group of 1 to 20 carbon atoms, an oxygen-containing group, a sulfur-containing group or a nitrogen-containing group, or a combination of $X^1$ and $X^2$ may form a stable conjugated diene (a hydrocarbon group of 1 to 20 carbon atoms, a halogenated hydrocarbon group of 1 to 20 carbon atoms, a silicon-containing group), and Y is a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, —O—, —CO—, —S—, —SO—, —SO$_2$—, —NR$^5$—, —P(R$^5$)—, —P(O)(R$^5$)—, —BR$^5$— or —AlR$^5$— (R$^5$ is hydrogen atom, a halogen atom, a hydrocarbon group of 1 to 20 carbon atoms or a halogenated hydrocarbon group of 1 to 20 carbon atoms).

The olefin polymerization catalyst according to the invention includes an embodiment of a solid catalyst wherein at least one of the component (A-1), the component (B-1) the component (B-2) and the component (C) is supported on a fine particle carrier and an embodiment of a prepolymerized catalyst comprising a fine particle carrier, the component (A-1), the component (B-1) (or the component (B-2)), an olefin polymer produced by prepolymerization, and optionally, the component (C).

The first process for preparing an olefin polymer according to the invention comprises homopolymerizing an olefin or copolymerizing two or more kinds of olefins in the presence of the above-described olefin polymerization catalyst.

The process of the invention can be applied for homopolymerization of ethylene, copolymerization of ethylene and an α-olefin of 3 to 20 carbon atoms, homopolymerization of propylene or copolymerization of propylene and an α-olefin other than propylene.

The first olefins polymer according to the invention is prepared by the above-mentioned process.

The first ethylene polymer and the first propylene polymer according to the invention are prepared by the above-mentioned process.

The second process for preparing an olefin polymer according to the invention comprises homopolymerizing an olefin or copolymerizing two or more kinds of olefins in the presence of a catalyst which comprises:

(A-2) a Group IVB transition metal compound represented by the following formula (II), (B) (B-1) an organoaluminum oxy-compound, and/or
(B-2) a compound which reacts with the transition metal compound (A-2) to form an ion pair, and optionally (C) an organoaluminum compound;

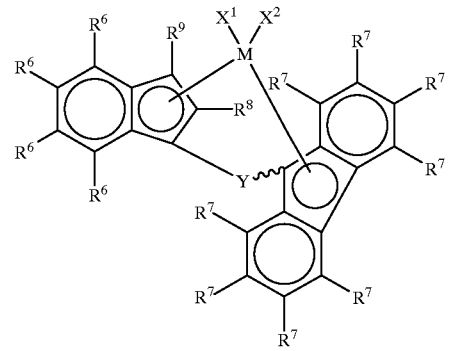

(II)

wherein M is a transition metal atom of Group IVB of the periodic table, $R^6$'s may be the same as or different from each other, and are each hydrogen atom, a halogen atom, an alkyl group of 1 to 10 carbon atoms, an aryl group of 6 to 10 carbon atoms, an alkenyl group of 2 to 10 carbon atoms, a silicon-containing group, an oxygen-containing group, a sulfur-containing group, a nitrogen-containing group or a phosphorus-containing group, $R^7$'s may be the same as or different from each other, and are each hydrogen atom, a halogen atom, an alkyl group of 1 to 10 carbon atoms, an aryl group of 6 to 20 carbon atoms, an alkenyl group of 2 to 10 carbon atoms, an arylalkyl group of 7 to 40 carbon atoms, an arylalkenyl group of 8 to 40 carbon atoms, an alkylaryl group of 7 to 40 carbon atoms, a silicon-containing group, an oxygen-containing group, a sulfur-containing group, a nitrogen-containing group or a phosphorus-containing group, $R^6$ and $R^7$ may be the same as or different from each other, any one of $R^8$ and $R^9$ is an alkyl group of 1 to 5 carbon atoms, and the remainder is hydrogen atom, a halogen atom, an alkyl group of 1 to 10 carbon atoms, an alkenyl group of 2 to 10 carbon atoms, a silicon-Containing group, an oxygen-containing group, a sulfur-containing group, a nitrogen-containing group or a phosphorus-containing group, $X^1$ and $X^2$ may be the same as or different from each other, and are the same as $X^1$ and $X^2$ in the above formula (I), and Y is the same as Y in the above formula (I), The process of the invention can be applied for homopolymerization of ethylene, copolymerization of ethylene and an α-olefin of 3 to 20 carbon atoms, homopolymerization of propylene or copolymerization of propylene and an α-olefin other than propylene.

The second olefin polymer according to the invention is prepared by the above-mentioned process, The second ethylene polymer and the second propylene polymer according to the invention are prepared by the above-mentioned process,

BRIEF DESCRIPTION OF THE DRAWING

FIG. 1 is an explanatory view showing steps for preparing the first olefin polymerization catalyst according to the present invention.

FIG. 2 is an explanatory view showing steps for preparing the olefin polymerization catalyst used in the second process for preparing an olefin polymer according to the present invention.

DETAILED DESCRIPTION OF THE INVENTION

The olefin polymerization catalyst, the process for preparing an olefin polymer and the olefin polymer according to the invention are described in detail hereinafter, The meaning of the term "polymerization" used herein is not limited to "homopolymerization" but may comprehend "copolymerization". Also, the meaning of the term "polymer" used herein is not limited to "homopolymer" but may comprehend "copolymer".

The olefin polymerization catalyst according to the invention is formed from:

(A-1) a Group IVB transition metal compound represented by the following formula (I)

(B) (B-1) an organoaluminum oxy-compound, and/or
(B-2) a compound which reacts with the transition metal compound (A-1) to form an ion pair,
and optionally (C) an organoaluminum compound.

First, each component for forming the olefin polymerization catalyst of the invention is described below.

The transition metal compound (A-1) used in the invention is a transition metal compound represented by the following formula (I).

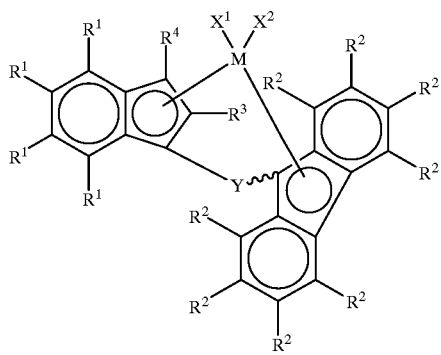

(I)

In the formula (I), M is a transition metal atom of Group IVB of the periodic table, specifically titanium, zirconium or hafnium, preferably zirconium.

$R^1$'s may be the same as or different from each other; and at least one of them is an aryl group of 11 to 20 carbon atoms, an arylalkyl group of 12 to 40 carbon atoms, an arylalkenyl group of 13 to 40 carbon atoms or an alkylaryl group of 12 to 40 carbon atoms, or at least two adjacent groups among groups indicated by RI form single or plural, aromatic or aliphatic rings together with carbon atoms to which said at least two groups are bonded. In this case, the rings formed by $R^1$ have 4 to 20 carbon atoms as a whole.

Examples of rings formed by at least two adjacent $R^1$ groups include a condensed phenyl group, a condensed cyclohexyl group, a condensed cyclopentadienyl group, a condensed dihydrocyclopentadienyl group, a condensed indenyl group, a condensed tetrahydroindenyl group, a condensed octahydrofluorenyl group, a condensed fluorenyl group and a condensed tetrahydrofluorenyl group. The ring formed by $R^1$ may be substituted with a linear alkyl group, a cyclic alkyl group, a halogen atom, a halogen-substituted alkyl group, an aryl group, a silicon-containing group, an oxygen-containing group, a sulfur-containing group, a nitrogen-containing group or a phosphorus-containing group.

$R^1$ other than the aryl group, the arylalkyl group, the arylalkenyl group, the alkylaryl group and $R^1$ for forming the aromatic ring or the aliphatic ring is hydrogen atom, a halogen atom, an alkyl group of 1 to 10 carbon atoms or silicon-containing alkyl group.

Examples of the aryl groups of 11 to 20 carbon atoms include biphenylyl, anthryl and phenanthryl.

Examples of the arylalkyl groups of 12 to 40 carbon atoms include phenanthrylmethyl, phenanthrylmethyl and phenanthrylpropyl.

Examples of the arylalkenyl groups of 13 to 40 carbon. atoms include vinylphenanthryl.

Examples of the alkylaryl groups of 12 to 40 carbon atoms include methylphenanthryl, ethylphenanthryl and propylphenanthryl.

Examples of the halogen atoms include fluorine, chlorine, bromine and iodine.

Examples of the alkyl groups of 1 to 10 carbon atoms include methyl, ethyl, propyl, butyl, hexyl, cyclohexyl, octyl and nonyl.

Examples of the silicon-containing alkyl group include dimethylsilyl, diethylsilyl and trimethylsilyl.

These alkyl groups, aryl groups, arylalkyl groups, arylalkenyl groups and alkylaryl groups may be substituted with halogens.

$R^2$'s may be the same as or different from each other, and are each hydrogen atom, a halogen atom, an alkyl group of 1 to 10 carbon atoms, an aryl group of 6 to 20 carbon atoms, an alkenyl group of 2 to 10 carbon atoms, an arylalkyl group of 7 to 40 carbon atoms, an arylalkenyl group of 8 to 40 carbon atoms, an alkylaryl group of 7 to 40 carbon atoms, a silicon-containing group, an oxygen-containing group, a sulfur-containing group, a nitrogen-containing group or a phosphorus-containing group.

At least two adjacent groups among groups indicated by $R^2$ may form single or plural, aromatic or aliphatic rings together with carbon atoms to which said at least two groups are bonded. In this case, the rungs formed by $R^2$ have 2 to 20 carbon atoms as a whole including carbon atoms to which the $R^2$ groups are bonded, and $R^2$ other than $R^2$ for forming the aromatic ring or the aliphatic ring is hydrogen atom, a halogen atom, an alkyl group of 1 to 10 carbon atoms or silicon-containing alkyl group.

When the two groups indicated by $R^2$ form single or plural, aromatic or aliphatic ring(s), the ring(s) may form the following structure together with the fluorenyl group.

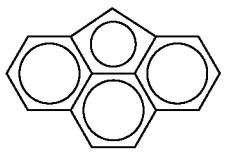

Examples of the alkyl groups of 1 to 10 carbon atoms and the halogen atoms are the same as those described above.

Examples of the aryl groups of 6 to 20 carbon atoms include phenyl, biphenylyl, α- or β-naphthyl, anthryl and phenanthryl.

Examples of the arylalkyl groups of 7 to 40 carbon atoms include benzyl, phenylethyl, phenylpropyl, phenanthrylmethyl, phenanthrylethyl and phenanthrylpropyl.

Examples of the arylalkenyl groups of 8 to 40 carbon atoms include styryl and vinylphenanthryl.

Examples of the alkylaryl groups of 7 to 40 carbon atoms include tolyl, dimethylphenyl, trimethylphenyl, ethylphenyl, propylphenyl, methylnaphthyl, methylphenanthryl, ethylphenanthryl and propylphenanthryl.

Examples of the alkenyl groups of 2 to 10 carbon atoms include vinyl, propenyl and cyclohexenyl.

Examples of the silicon-containing groups include methylsilyl, phenylsilyl, dimethylsilyl, diphenylsilyl, trimethylsilyl, triethylsilyl, tripropylsilyl, tricyclohexylsilyl, triphenylsilyl, dimethylphenylsilyl, methyldiphenylsilyl, tritolylsilyl and trinaphthylsilyl.

Examples of the oxygen-containing groups include hydroxyl group; alkoxy groups, such as methoxy, ethoxy, propoxy and butoxy; aryloxy groups, such as phenoxy, methylphenoxy, dimethylphenoxy and naphthoxy; and arylalkoxy groups, such as phenylmethoxy and phenylethoxy.

Examples of the sulfur-containing groups include those wherein oxygen is replaced with sulfur in the above-exemplified oxygen-containing groups, sulfonato groups, such as methylsulfonato, trifluoromethanesulfonato, phenylsulfonato, benzylsulfonato, p-toluenesulfonato, trimethylbenzenesulfonato, triisobutylbenzenesulfonato, p-chlorobenzenesulfonato and pentafluorobenzenesulfonato; and sulfinato groups, such as methylsulfinato, phenylsulfinato, benzenesulfinato, p-toluenesulfinato, trimethylbenzenesulfinato and pentafluorobenzenesulfinato.

Examples of the nitrogen-containing groups include amino group; alkylamino groups, such as methylamino, dimethylamino, diethylamino, dipropylamino, dibutylamino and dicyclohexylamino; and arylamino or alkylarylamino groups, such as phenylamino, diphenylamino, ditolylamino, dinaphtylamino and methylphenylamino.

Examples of the phosphorus-containing groups include dimethylphosphino and diphenylphosphino.

Of these, $R^2$ is preferably hydrogen or an alkyl group, particularly preferably hydrogen or a hydrocarbon group of 1 to 3 carbon atoms, i.e., methyl, ethyl or propyl.

$R^1$ and $R^2$ may be the same as or different from each other.

$R^3$ and $R^4$ may be the same as or different from each other, and are each hydrogen atom, a halogen atom, an alkyl group of 1 to 10 carbon atoms, an aryl group of 6 to 20 carbon atoms, an alkenyl group of 2 to 10 carbon atoms, an arylalkyl group of 7 to 40 carbon atoms, an arylalkenyl group of 8 to 40 carbon atoms, an alkylaryl group of 7 to 40 carbon atoms, a silicon-containing group, an oxygen-containing group, a sulfur-containing group, a nitrogen-containing group or a phosphorus-containing group.

Of these, at least one of $R^3$ and $R^4$ is preferably an alkyl group of 1 to 3 carbon atoms.

$X^1$ and $X^2$ may be the same as or different from each other, and are each hydrogen atom, a halogen atom, a hydrocarbon group of 1 to 20 carbon atoms, a halogenated hydrocarbon group of 1 to 20 carbon atoms, an oxygen-containing group, a sulfur-containing group or a nitrogen-containing group, or a combination of $X^1$ and $X^2$ may form a stable conjugated diene (a hydrocarbon group of 1 to 20 carbon atoms, a halogenated hydrocarbon group of 1 to 20 carbon atoms and a silicon-containing group).

Examples of the halogen atoms, the oxygen-containing groups, the sulfur-containing groups and the nitrogen-containing groups are the same as those described above.

Examples of the hydrocarbon groups of 1 to 20 carbon atoms include alkyl groups, such as methyl, ethyl, propyl, butyl, hexyl, cyclohexyl, octyl, nonyl, dodecyl, eicosyl, norbornyl and adamantyl; alkenyl groups, such as vinyl, propenyl and cyclohexenyl; arylalkyl groups, such as benzyl, phenylethyl and phenylpropyl; and aryl groups, such as phenyl, tolyl, dimethylphenyl, trimethylphenyl, ethylphenyl, propylphenyl, biphenylyl, α- or β-naphthyl, methylnaphthyl, anthryl, phenanthryl, benzylphenyl, pyrenyl, acenaphthyl, phenalenyl, aceanthrylenyl, tetrahydronaphthyl and indanyl.

Examples of the halogenated hydrocarbon groups of 1 to 20 carbon atoms include those wherein halogens are substituted in the above-exemplified hydrocarbon groups of 1 to 20 carbon atoms.

As the diene formed from $X^1$ and $X^2$, there are exemplified $\eta^4$-1,4-diphenyl-1,3-butadiene, $\eta^4$-1,3-butadiene, $\eta^4$-1,4-dibenzyl-1,3-butadiene, $\eta^4$-1-phenyl-1,3-pentadiene, $\eta^4$-3-methyl-1,3-pentadiene, $\eta^4$-1,4-bis(trimethylsilyl)-1,3-butadiene, 2,3-dimethylbutadiene, $\eta^4$-2,4-hexadiene, and isoprene. Among these, preferred are 1,3-butadiene, 2,4-hexadiene, 1-phenyl-1,3-pentadiene, and 1,4-diphenylbutadiene, and each may be substituted with a hydrocarbon group of 1 to 10 carbon atoms.

Of these, preferable are the halogen atoms, the hydrocarbon groups of 1 to 20 carbon atoms and the sulfur-containing groups.

Y s a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, —O—, —CO—, —S—, —SO—, —SO$_2$—, —NR$^5$—, —P (R$^5$)—, —P(O)(R$^5$) —, —BR$^5$— or —AlR$^5$— (R$^5$ is hydrogen atom, a halogen atom, a hydrocarbon group of 1 to 20 carbon atoms or a halogenated hydrocarbon group of 1 to 20 carbon atoms).

Examples of such groups include:

divalent hydrocarbon groups of 1 to 20 carbon atoms, such as alkylene groups, specifically, methylene, dimethylmethylene, 1,2-ethylene, dimethyl-1,2-ethylene, 1,3-trimethylene, 1,4-tetramethylene, 1,2-cyclohexylene and 1,4-cyclohexylene, and arylalkylene groups, specifically, diphenylmethylene and diphenyl-1,2-ethylene;

halogenated hydrocarbon groups wherein halogens are substituted in the above-exemplified divalent hydrocarbon groups of 1 to 20 carbon atoms, such as chloromethylene;

divalent silicon-containing groups, such as alkylsilylene, alkylarylsilylene and arylsilylene groups specifically, methylsilylene, dimethylsilylene, diethylsilylene, di(n-propyl)silylene, di(i-propyl) silylene, di (cyclohexyl) silylene, methylphenylsilylene, diphenylsilylene, di(p-tolyl)silylene and di(p-chlorophenyl)silylene, and alkyldisilylene, alkylaryldisilylene and aryldisilylene groups, specifically, tetramethyl-1,2-disilylene and tetraphenyl-1,2-disilylene;

divalent germanium-containing groups wherein silicon is replaced with germanium in the above-exemplified divalent silicon-containing groups; and divalent tin-containing groups wherein silicon is replaced with tin in the above-exemplified divalent silicon-containing groups.

Of these divalent groups, preferable are those wherein the shortest linkage part of —Y— in the formula (I) is composed of one or two atoms.

$R^5$ is the same halogen atom, hydrocarbon group of 1 to 20 carbon atoms or halogenated hydrocarbon group of 1 to 20 carbon atoms as described above.

Of these, Y is preferably a divalent hydrocarbon group of 1 to 5 carbon atoms, a divalent silicon-containing group or a divalent germanium-containing group, more preferably a divalent silicon-containing group, particularly preferably alkylsilylene, alkylarylsilylene or aylsilylene.

Listed below are examples of the transition metal compounds represented by the formula (I)

Ethylene{2-methyl-4(9-phenanthryl)-1-indenyl}(9-fluorenyl)zirconium dichloride,

Ethylene{2-methyl-4(9-phenanthryl)-1-indenyl}(2,7-dimethyl-9-fluorenyl)zirconium dichloride, Ethylene{2-methyl-4(9-phenanthryl)-1-indenyl}(2,7-di-t-butyl-9-fluorenyl)zirconium dichloride, Ethylene(2-methyl-4,5-benzo-1-indenyl)(9-fluorenyl)zirconium dichloride, Ethylene(2-methyl-4,5-benzo-1-indenyl)(2,7-dimethyl-9-fluorenyl)zirconium dichloride, Ethylene(2-methyl-4,5-benzo-1-indenyl)(2,7-di-t-butyl-9-fluorenyl)zirconium dichloride, Ethylene(2-methyl-4,3-benzo-1-indenyl)(2,7-dibromo-9-fluorenyl)zirconium dichloride, Ethylene(2,6-dimethyl-4,5-benzo-1-indenyl)(2,7-di-t-butyl-9-fluorenyl)zirconium dichloride, Ethylene(2,6-dimethyl-4,5-benzo-1-indenyl)(2,7-dibromo-9-fluorenyl)zirconium dichloride, Ethylene(2-methyl-α-acenaphtho-1-indenyl)(9-fluorenyl)zirconium dichloride, Ethylene(2-methyl-α-acenaphtho-1-indenyl)(2,7-dimethyl-9-fluorenyl)zirconium dichloride, Ethylene(2-methyl-α-acenaphtho-1-indenyl)(2,7-di-t-butyl-9-fluorenyl)zirconium dichloride, Dimethylsilylene{2-methyl-4(9-phenanthryl)-1-indenyl}(9-fluorenyl)zirconium dichloride, Dimethylsilylene{2-n-propyl-4(9-phenanthryl)-1-indenyl}(9-fluorenyl)zirconium dichloride, Dimethylsilylene{2-methyl-4(9-phenanthryl)-1-indenyl}(2,7-dimethyl-9-fluorenyl)zirconium dichloride, Dimethylsilylene{2-methyl-4(9-phenanthryl)-1-indenyl}(2,7-di-t-butyl-9-fluorenyl)zirconium dichloride, Dimethylsilylene(2-methyl-4,5-benzo-1-indenyl)(9-fluorenyl)zirconium dichloride, Dimethylsilylene(2-methyl-4,5-benzo-1-indenyl)(2,7-dimethyl-9-fluorenyl)zirconium dichloride, Dimethylsilylene(2-methyl-4,5-benzo-1-indenyl)(2,7-di-t-butyl-9-fluorenyl)zirconium dichloride, Dimethylsilylene(2-methyl-α-acenaphtho-1-indenyl)(9-fluorenyl)zirconium dichloride, Dimethylsilylene(2-methyl-α-acenaphtho-1-indenyl)(2,7-dimethyl-9-fluorenyl)zirconium dichloride, Dimethylsilylene(2-methyl-α-acenaphtho-1-indenyl)(2,7-di-t-butyl-3-fluorenyl)zirconium dichloride, Diphenylsilylene{2-methyl-4(9-phenanthryl)-1-indenyl}(9-fluorenyl)zirconium dichloride, Diphenylsilylene{2-methyl-4(9-phenanthryl)-1-indenyl}(2,7-dimethyl-9-fluorenyl)zirconium dichloride, Diphenylsilylene{2-methyl-4(9-phenanthryl)-1-indenyl}(2,7-di-t-butyl-9-fluorenyl)zirconium dichloride, Diphenylsilylene(2-methyl-4,5-benzo-1-indenyl)(9-fluorenyl)zirconium dichloride, Diphenylsilylene(2-methyl-4,5-benzo-1-indenyl)(2,7-dimethyl-9-fluorenyl)zirconium dichloride, Diphenylsilylene(2-methyl-4,5-benzo-1-indenyl)(2,7-di-t-butyl-9-fluorenyl)zirconium dichloride, Diphenylsilylene(2-methyl-α-acenaphtho-1-indenyl)(9-fluorenyl)zirconium dichloride, Diphenylsilylene(2-methyl-α-acenaphtho-1-indenyl)(2,7-dimethyl-9-fluorenyl)zirconium dichloride, Diphenylsilylene(2-methyl-α-acenaphtho-1-indenyl)(2,7-di-t-butyl-9-fluorenyl)zirconium dichloride, Methylphenylsilylene{2-methyl-4(9-phenanthryl)-1-indenyl}(9-fluorenyl)zirconium dichloride, Methylphenylsilylene{2-methyl-4(9-phenanthryl)-1-indenyl}(2,7-dimethyl-9-fluorenyl)zirconium dichloride, Methylphenylsilylene{2-methyl-4(9-phenanthryl)-1-indenyl}(2,7-di-t-butyl-9-fluorenyl)zirconium dichloride, Methylphenylsilylene(2-methyl-4,5-benzo-1-indenyl)(9-fluorenyl)zirconium dichloride, Methylphenylsilylene(2-methyl-4,5-benzo-1-indenyl)(2,7-dimethyl-9-fluorenyl)zirconium dichloride, Methylphenylsilylene(2-methyl-4,5-benzo-1-indenyl)(2,7-di-t-butyl-9-fluorenyl)zirconium dichloride, Methylphenylsilylene(2-methyl-α-acenaphtho-1-indenyl)(9-fluorenyl)zirconium dichloride, Methylphenylsilylene(2-methyl-α-acenaphtho-1-indenyl)(2,7-dimethyl-9-fluorenyl)zirconium dichloride, Methylphenylsilylene(2-methyl-α-acenaphtho-1-indenyl)(2,7-di-t-butyl-9-fluorenyl)zirconium dichloride, Ethylene{3-methyl-4(9-phenanthryl)-1-indenyl}(9-fluorenyl)zirconium dichloride, Ethylene{3-methyl-4(9-phenanthryl)-1-indenyl}(2,7-dimethyl-9-fluorenyl)zirconium dichloride, Ethylene{3-methyl-4(9-phenanthryl)-1-indenyl}(2,7-di-t-butyl-9-fluorenyl)zirconium dichloride, Ethylene(3-methyl-4,5-benzo-1-indenyl)(9-fluorenyl)zirconium dichloride, Ethylene(3-methyl-4,5-benzo-1-indenyl)(2,7-dimethyl-9-fluorenyl)zirconium dichloride, Ethylene(3-methyl-4,5-benzo-1-indenyl)(2,7-di-t-butyl-9-fluorenyl)zirconium dichloride, Ethylene(3-methyl-α-acenaphtho-1-indenyl)(9-fluorenyl)zirconium dichloride, Ethylene(3-methyl-α-acenaphtho-1-indenyl)(2,7-dimethyl-9-fluorenyl)zirconium dichloride, Ethylene(3-methyl-α-acenaphtho-1-indenyl)(2,7-di-t-butyl-9-fluorenyl)zirconium dichloride, Dimethylsilylene{3-methyl-4(9-phenanthryl)-1-indenyl}(9-fluorenyl)zirconium dichloride, Dimethylsilylene{3-methyl-4(9-phenanthryl)-1-indenyl}(2,7-dimethyl-9-fluorenyl)zirconium dichloride,
Dimethylsilylene{3-methyl-4(9-phenanthryl)-1-indenyl}(2,7-di-t-butyl-9-fluorenyl)zirconium dichloride,
Dimethylsilylene(3-methyl-4,5-benzo-1-indenyl)(9-fluorenyl)zirconium dichloride,
Dimethylsilylene(3-methyl-4,5-benzo-1-indenyl)(2,7-dimethyl-9-fluorenyl)zirconium dichloride,
Dimethylsilylene(3-methyl-4,5-benzo-1-indenyl)(2,7-di-t-butyl-9-fluorenyl)zirconium dichloride,
Dimethylsilylene(3-methyl-α-acenaphtho-1-indenyl)(9-fluorenyl)zirconium dichloride,
Dimethylsilylene(3-methyl-α-acenaphtho-1-indenyl)(2,7-dimethyl-9-fluorenyl)zirconium dichloride,
Dimethylsilylene(3-methyl-α-acenaphtho-1-indenyl)(2,7-di-t-butyl-9-fluorenyl)zirconium dichloride,
Diphenylsilylene{3-methyl-4(9-phenanthryl)-1-indenyl}(2,7-dimethyl-9-fluorenyl)zirconium dichloride,
Dipenylsilylene{3-methyl-4(9-phenanthryl)-1-indenyl}(2,7-di-t-butyl-9-fluoreny)zirconium dichloride,
Diphenylsilylene(3-methyl-4,5-benzo-1-indenyl)(9-fluorenyl)zirconium dichloride,
Diphenylsilylene(3-methyl-4,5-benzo-1-indenyl)(2,7-dimethyl-9-fluorenyl)zirconium dichloride,
Diphenylsilylene(3-methyl-4,5-benzo-1-indenyl)(2,7-di-t-butyl-9-fluorenyl)zirconium dichloride,
Diphenylsilylene(3-methyl-α-acenaphtho-1-indenyl)(9-fluorenyl)zirconium dichloride,
Diphenylsilylene(3-methyl-α-acenaphtho-1-indenyl)(2,7-dimethyl-9-fluorenyl)zirconium dichloride,
Diphenylsilylene(3-methyl-α-acenaphtno-1-indenyl)(2,7-di-t-butyl-9-fluorenyl)zirconium dichloride,
Methylphenylsilylene{3-methyl-4(9-phenanthryl)-1-indenyl}(9-fluorenyl)zirconium dichloride,
Methylphenylsilylene{3-methyl-4(9-phenarthryl)-1-indenyl}(2,7-dimethyl-9-fluorenyl)zirconium dichioride,
Methylphenylsilylene{3-methyl-4(9-phenarthryl)-1-indenyl}(2,7-di-t-butyl-9-fluorenyl)zirconium dichloride,
Methylphenylsilylene(3-methyl-4,5-benzo-1-indenyl)(9-fluorenyl)zirconium dichloride,
Methylphenylsilylene(3-methyl-4,5-benzo-1-indenyl)(2,7-dimethyl-9-fluorenyl)ziconium dichloride,
Methylphenylsilylene(3-methyl-4,5-benzo-1-indenyl)(2,7-di-t-butyl-9-fluorenyl)zirconium dichloride,
Methylphenylsilylene(3-methyl-α-acenaphtho-1-indenyl)(9-fluorenyl)zirconium dichloride,
Methylphenylsilylene(3-methyl-α-acenaphtho-1-indenyl)(2,7-dimethyl-9-fluorenyl)zirconium dichloride,
Methylphenylsilylene(3-methyl-α-acenaphtho-1-indenyl)(2,7-di-t-butyl-9-fluorenyl)zirconium dichloride,
Ethylene(2-methyl-4,5-benzo-1-indenyl)(2,7-ditrimethylsilyl-9-fluorenyl)zirconium dichloride,
Ethylene(2,6-dimethyl-4,5-benzo-1-indenyl)(2,7-di-t-butyl-9-fluorenyl)zirconium dichloride,
Ethylene(2,7-dimethyl-4,5-benzo-1-indenyl)(2,7-di-t-butyl-9-fluorenyl)zirconium dichloride,
Ethylene(2,7-dimethyl-4,5-(2-methyl-benzo)-1-indenyl)(2,7-di-t-butyl-9-fluorenyl)zirconium dichloride,
Dimethylsilylene(2-methyl-4,5-benzo-1-indenyl)(2,7-ditrimethylsilyl-9-fluorenyl)zirconium dichloride,
Dimethylsilylene(2-methyl-4,5-benzo-1-indenyl)(2,7-di-t-butyl-9-fluorenyl)zirconium-bis(methanesulfonate),
Dimethylsilylene(2-methyl-4,5-benzo-1-indenyl)(2,7-di-t-butyl-9-fluorenyl)zirconium-bis(trifluoromethanesulfonato),
Dimethylsilylene(2,6-dimethyl-4,5-benzo-1-indenyl)(2,7-ditrimethylsilyl-9-fluorenyl)zirconium dichloride,
Dimethylsilylene(2,6-dimethyl-4, 5-benzo-1-indenyl)(2,7-ditrimethylsilyl-9-fluorenyl)zirconium-bis(methanesulfonate),
Diemthylsilylene(2,5-dimethyl-4,5-benzo-1-indenyl)(2,7-ditrimethylsilyl-9-fluorenyl)zirconium-bis(trifluoromethanesulfonate),
Dimethylsilylene(2,6-dimethyl-4,5-benzo-1-indenyl)(2,7-di-t-butyl-9-fluorenyl)zirconium dichloride,
Dimethylsilylene(2,7-dimethyl-4,5-benzo-1-indenyl)(2,7-di-t-butyl-9-fluorenyl)zirconium dichloride,
Dimethylsilylene(2,7-dimethyl-4,5-(2-methyl-benzo)-1-indenyl)(2,7-di-t-butyl-9-fluorenyl)zirconium dichioride,
Dimetlylsilylene(2-methyl-4,5-benzo-1-indenyl)(2,7-dibromo-9-fluorenyl)zirconium dichloride,
Dimethylsilylene(2,6-dimethyl-4,5-benzo-1-indenyl)(2,7-dibromo-9-fluorenyl)zirconium dichloride,
Dimethylsilylene(2-methyl-4,5-benzo-1-indenyl)(2,7-di-t-butoxy-9-fluorenyl)zirconium dichloride,
Dimethylsilylene(2,6-dimethyl-4,5-benzo-1-indenyl)(2,7-di-t-butoxy-9-fluorenyl)zirconium dichloride,
Dimethylsilylene(2-methyl-4,5-benzo-1-indenyl)(2,7-diphenyl-9-fluorenyl)zirconium dichloride,
Dimethylsilylene(2,6-dimethyl-4,5-benzo-1-indenyl)(2,7-diphenyl-9-fluorenyl)zirconium dichloride,
Dimethylsilylene(2-methyl-4,5-benzo-1-indenyl)(2,7-di-i-propyl-9-fluorenyl)zirconium dichloride,
Dimethylsilylene(2,6-dimethyl-4,5-benzo-1-indenyl)(2,7-di-i-propyl-9-fluorenyl)zirconium dichloride,
Dimethylsilylene(2,6-dimethyl-4,5-benzo-1-indenyl)(2,7-dimethyl-9-fluorenyl)zirconium dichloride,
Dimethylsilylene(2,6-dimethyl-4,5-(1-methyl-benzo)-1-indenyl)(2,7-di-t-butyl-9-fluorenyl)zirconium dichloride,
Dimethylsilylene(2,7-dimethyl-4,5-(2-methyl-benzo)-1-indenyl)(2,7-di-trimethylsilyl-9-fluorenyl)zirconium dichloride,
Dimethylsilylene(2,7-dimethyl-4,5-(2-methyl-benzo)-1-indenyl)(2,7-dibromo-9-fluorenyl)zirconium dichloride,
Dimethylsilylene(2,7-dimethyl-4,3-(2-methyl-benzo)-1-indenyl) (2,7-di-t-butoxy-9-fluorenyl)zirconium dichloride,
Dimethylsilylene(2,7-dimethyl-4,5-(2-methyl-benzo)-1-indenyl)(2,7-diphenyl-9-fluorenyl)zirconium dichloride,
Dimethylsilylene(2,7-dimethyl-4,5-(2-methyl-benzo)-1-indenyl)(2,7-di-i-propyl-9-fluorenyl)zirconium dichloride,
Dimethylsilylene(2,7-dimethyl-4,5-(2-methyl-benzo)-1-indenyl)(2,7-dimethyl-9-fluorenyl)zirconium dichloride,
Dimethylsilylene(2,7-dimethyl-4,5-(1-methyl-benzo)-1-indenyl)(2,7-di-t-butyl-9-fluorenyl)zirconium dichloride, Dimethylsilylene(2,7-dimethyl-4,5-(1-methyl-benzo)-1-indenyl)(2,7-di-trimethylsilyl-9-fluorenyl)zirconium dichloride, Dimethylsilylene(2,7-dimethyl-4,5-(1-methyl-benzo)-1-indenyl)(2,7-dibromo-9-fluorenyl)ziroonium dichloride, Dimethylsilylene(2,7-dimethyl-4,5-(1-methyl-benzo)-1-indenyl)(2,7-di-t-butoxy-9-fluorenyl)zirconium dichloride, Dimemhylsilylene(2,7-dimethyl-4,5-(1-methyl-benzo)-1-indenyl)(2,7-diphenyl-9-fluorenyl)zirconium dichloride, Dimethylsilylene(2,7-dimethyl-4,5-(1-methyl-benzo)-1-indenyl)(2,7-di-i-propyl-9-fluorenyl)zirconium dichloride, Dimethylsilylene(2,7-dimethyl-4,5-(1-methyl-benzo)-1-indenyl)(2,7-dimethyl-9-fluorenyl)zirconium dichloride, Dimethylsilylene(2-methyl-4,5-benzo-1-indenyl)(2,7-dibromo-9-fluorenyl)zirconium bis(methanesulfonate), Dimethylsilylene(2,6-dimethyl-4,5-benzo-1-indenyl)(2,7-dibromo-9-fluorenyl)zirconium bis(methanesulfonate), Dimethylsilylene(2-methyl-4,5-benzo-1-indenyl)(2,7-di-t-butoxy-9-fluorenyl)zirconium bis(methanesulfonate), Dimethylsilylene(2,6-dimethyl-4,5-benzo-1-indenyl)(2,7-di-t-butoxy-9-fluoenyl)zirconium bis(methanesulfanate), Dimethylsilylene(2-methyl-4,5-benzo-1-indenyl)(2,7-diphenyl-9-fluorenyl)zirconium bis(methanesulfonate), Dinethylsilylene(2,6-dimethyl-4,5-benzo-1-indenyl)(2,7-diphenyl-9-fluorenyl)ziconium bis(methanesulfonate), Dimethylsilylene(2-methyl-4,5-benzo-1-indenyl)(2,7-di-i-propyl-9-fluorenyl)zirconium bis(methanesulfonate), Dimethylsilylene(2,6-dimethyl-4,5-benzo-1-indenyl)(2,7-d4-i-propyl-9-fluorenyl)zirconium bis(methanesulfonate), Dimethylsilylene(2,6-dimethyl-4,5-benzo-1-indenyl)(2,7-dimethyl-9-fluorenyl)zirconium bis(methanesulfonate), Dimethylsilylene(2,7-dimethyl-4,5-(2-methyl-benzo)-1-indenyl)(2,7-di-trimethylsilyl-9-fluorenyl)zirconium bis(methanesulfonate), Dimethylsilylene(2,7-dimethyl-4,5-(2-methyl-benzo)-1-indenyl)(2,7-dibromo-9-fluorenyl)zirconium bis(methanesulfonate), Dimethylsilylene(2,7-dimethyl-4,5-(2-methyl-benzo)-1-indenyl)(2,7-di-t-butoxy-9-fluorenyl)zirconium bis(methanesulfonate), Dimethylsilylene(2,7-dimethyl-4,5-(2-methyl-benzo)-1-indenyl)(2,7-diphenyl-9-fluorenyl)zirconium bis(methanesulfonate), Dimethylsilylene(2,7-dimethyl-4,5-(2-methyl-benzo)-1-indenyl)(2,7-di-i-propyl-9-fluorenyl)zirconium bis(methanesulfonate), Dimethylsilylene(2,7-dimethyl-4,5-(2-methyl-benzo)-1-indenyl)(2,7-dimethyl-9-fluorenyl)zirconium bis(methanesulfonate), Dimethylsilylene(2,7-dimethyl-4,5-(1-methyl-benzo)-1-indenyl)(2,7-di-t-butyl-9-fluorenyl)zirconium bis(methanesulfonate), Dimethylsilylene(2,7-dimethyl-4,5-(1-methyl-benzo)-1-indenyl)(2,7-di-trimethylsilyl-9-fluorenyl)zirconium bis(methanesulfonate), Dinethylsilylene(2,7-dimethyl-4,5-(1-methyl-benzo)-1-indenyl)(2,7-dibromo-9-fluorenyl)zirconium bis(methanesulfonate), Dimethylsilylene(2,7-dimethyl-4,5-(1-methyl-benzo)-1-indenyl)(2,7-di-t-butoxy-9-fluorenyl)zirconium bis(methanesulfonate), Dimethylsilylene(2,7-dimethyl-4,5-(1-methyl-benzo)-1-indenyl)(2,7-diphenyl-9-fluorenyl)zirconium bis(methanesulfonate), Dimethylsilylene(2,7-dimethyl-4,5-(1-methyl-benzo)-1-indenyl)(2,7-di-i-propyl-9-fluorenyl)zirconium bis(methanesulfonate), Dimethylsilylene(2,7-dimethyl-4,5-(1-methyl-benzo)-1-indenyl)(2,7-dimethyl-9-fluorenyl)zirconium bis(methanesulfonate), Dimethylsilylene(2-methyl-4,5-benzo-1-indenyl)(2,7-dibromo-9-(4,5-methylenephenanthryl))zirconium dichloride, Dimethylsilylene(2,6-dimethyl-4,5-benzo-1-indenyl)(2,7-dibromo-9-(4,5-methylenephenanthryl))zirconium dichloride, Dimethylsilylene(2-methyl-4,5-benzo-1-indenyl)(2,7-di-t-butoxy-9-(4,5-methylenephenanthryl))zirconium dichloride, Dimethylsilylene(2,6-dimethyl-4,5-benzo-1-indenyl)(2,7-di-t-butoxy-9-(4,5-methylenephenanthryl))zirconium dichloride, Dimethylsilylene(2-methyl-4,5-benzo-1-indenyl)(2,7-diphenyl-9-(4,5-methylenephenanthryl))zirconium dichloride, Dimethylsilylene(2,6-dimethyl-4,5-benzo-1-indenyl)(2,7-diphenyl-9-(4,5-methylenephenanthryl))zirconium dichloride, Dimethylsilylene(2-methyl-4,5-benzo-1-indenyl)(2,7-di-i-propyl-9-(4,5-methylenephenanthryl))zirconium dichloride, Dimethylsilylene(2,6-dimethyl-4,5-benzo-1-indenyl)(2,7-di-i-propyl-9-(4,5-methylenephenanthryl))zirconium dichloride, Dimethylsilylene(2,6-dimethyl-4,5-benzo-1-indenyl)(2,7-dimethyl-9-(4,5-methylenephenanthryl))zirconium dichloride, Dimethylsilylene(2,7-dimethyl-4,5-(2-methyl-benzo)-1-indenyl)(2,7-di-trimethylsilyl-9-(4,5-methylenephenanthryl))zirconium dichloride, Dimethylsilylene(2,7-dimethyl-4,5-(2-methyl-benzo)-1-indenyl)(2,7-dibromo-9-(4,5-methylenephenanthryl))zirconium dichloride, Dimethylsilylene(2,7-dimethyl-4,5-(2-methyl-benzo)-1-indenyl)(2,7-di-t-butoxy-9-(4,5-methylenephenanthryl))zirconium dichloride, Dimethylsilylene(2,7-dimethyl-4,5-(2-methyl-benzo)-1-indenyl)(2,7-diphenyl-9-(4,5-methylenephenanthryl))zirconium dichloride, Dimethylsilylene(2,7-dimethyl-4,5-(2-methyl-benzo)-1-indenyl)(2,7-di-i-propyl-9-(4,5-methylenephenanthryl))zirconium dichloride, Dimethylsilylene(2,7-dimethyl-4,5-(2-methyl-benzo)-1-indenyl)(2,7-dimethyl-9-(4,5-methylenephenanthryl))zirconium dichloride, Dimethylsilylene(2,7-dimethyl-4,5-(1-methyl-benzo)-1-indenyl)(2,7-di-t-butyl-9-(4,5-methylenephenanthryl))zirconium dichloride, Dimethylsilylene(2,7-dimethyl-4,5-(1-methyl-benzo)-1-indenyl)(2,7-di-trimethylsilyl-9-(4,5-methylenephenanthryl))zirconium dichloride, Dimethylsilylene(2,7-dimethyl-4,5-(1-methyl-benzo)-1-indenyl) (2,7-dibromo-9-(4,5-methylenephenanthryl))zirconium dichloride, Dimethylsilylene(2,7-dimethyl-4,5-(1-methyl-benzo)-1-indenyl)(2,7-di-t-butoxy-9-(4,5-methylenephenanthryl))zirconium dichloride, Dimethylsilylene(2,7-dimethyl-4,5-(1-methyl-benzo)-1-indenyl)(2,7-diphenyl-9-(4,5-methylenephenanthryl))zirconium dichloride, Dimethylsilylene(2,7-dimethyl-4,5-(1-methyl-benzo)-1-indenyl)(2,7-di-i-propyl-9-(4,5-methylenephenanthryl))zirconium dichloride, Dimethylsilylene(2,7-dimethyl-4,5-(1-methyl-benzo)-1-indenyl)(2,7-dimethyl-9-(4,5-methylenephenanthryl))zirconium dichloride, Dimethylsilylene(2-methyl-4,5-benzo-1-indenyl)(2,7-di-t-butyl-9-(4,5-methylenephenanthryl))zirconium dichloride, Dimethylsilylene(2-methyl-4,5-benzo-1-indenyl)(2,7-di-trimethylsilyl-9-(4,5-methylenephenanthryl))zirconium dichloride, Dimethylsilylene(2,6-dimethyl-4,3-benzo-1-indenyl)(2,7-di-t-butyl-9-(4,5-methylenephenanthryl))zirconium dichloride, Dimethylsilylene(2,6-dimethyl-4,5-benzo-1-indenyl)(2,7-di-trimethylsilyl-9-(4,5-methylenephenanthryl))zirconium dichloride, Dimethylsilylene(2,7-dimethyl-4,5-(2-methyl-benzo)-1-indenyl)(2,7-di-t-butyl-9-(4,5-methylenephenanthryl))zirconium dichloride, Dimethylsilylene(2,7-dimethyl-4,5-(2-methyl-benzo)-1-indenyl)(2,7-di-trimethylsilyl-9-(4,5-methylenephenanthryl))zirconium dichloride, Dimethylmethylene(2-methyl-4,5-benzo-1-indenyl)(2,7-dibromo-9-fluorenyl)zirconium dichloride, Dimethylmethylene(2,6-dimethyl-4,5-benzo-1-indenyl) (2,7-dibromo-9-fluorenyl)zirconium dichloride, Dimethylmethylene(2-methyl-4,5-benzo-1-indenyl)(2,7-di-t-butoxy-9-fluorenyl)zirconium dichloride, Dimethylmethylene(2,6-dimethyl-4,5-benzo-1-indenyl) (2,7-di-t-butoxy-9-fluorenyl)zirconium dichloride, Dimethylmethylene(2-methyl-4,5-benzo-1-indenyl)(2,7-diphenyl-9-fluorenyl)zirconium dichloride, Dimethylmethylene(2,6-dimethyl-4,5-benzo-1-indenyl) (2,7-diphenyl-9-fluorenyl)zirconium dichloride, Dimethylmethylene(2-methyl-4,5-benzo-1-indenyl)(2,7-di-i-propyl-9-fluorenyl)zirconium dichloride, Dimethylmethylene(2,6-dimethyl-4,5-benzo-1-indenyl) (2,7-di-i-propyl-9-fluorenyl)zirconium dichloride, Dimethylmethylene(2,6-dimethyl-4,5-benzo-1-indenyl) (2,7-dimethyl-9-fluorenyl)zirconium dichloride, Dimethylmethylene(2,7-dimethyl-4,5-(2methyl-benzo)-1-indenyl)(2,7-di-trimethylsilyl-9-fluorenyl)zirconium dichloride, Dimethylmethylene(2,7-dimethyl-4,5-(2-methyl-benzo)-1-indenyl)(2,7-dibromo-9-fluorenyl)zirconium dichloride, Dimethylmethylene(2,7-dimethyl-4,5-(2-methyl-benzo)-1-indenyl)(2,7-di-t-butoxy-9-fluorenyl)zirconium dichloride, Dimethylmethylene(2,7-dimethyl-4,5-(2-methyl-benzo)-1-indenyl)(2,7-diphenyl-9-fluorenyl)zirconium dichloride, Dimethylmethylene(2,7-dimethyl-4,5-(2-methyl-benzo)-1-indenyl)(2,7-di-i-propyl-9-fluorenyl)zirconium dichloride, Dimethylmethylene(2,7-dimethyl-4,5-(2-methyl-benzo)-1-indenyl)(2,7-dimethyl-9-fluorenyl)zirconium dichloride, Dimethylmethylene(2,7-dimethyl-4,5-(1-methyl-benzo)-1-indenyl)(2,7-di-t-butyl-9-fluorenyl)zirconium dichloride, Dimethylmethylene(2,7-dimethyl-4,5-(1-methyl-benzo)-1-indenyl)(2,7-di-trimethylsilyl-9-fluorenyl)zirconium dichloride, Dimethylmethylene(2,7-dimethyl-4,5-(1-methyl-benzo)-1-indenyl)(2,7-dibromo-9-fluorenyl)zirconium dichloride, Dimethylmethylene(2,7-dimethyl-4,5-(1-methyl-benzo)-1-indenyl)(2,7-di-t-butoxy-9-fluorenyl)zirconium dichloride, Dimethylmethylene(2,7-dimethyl-4,5-(1-methyl-benzo)-1-indenyl)(2,7-diphenyl-9-fluorenyl)zirconium dichloride, Dimethylmethylene(2,7-dimethyl-4,5-(1-methyl-benzo)-1-indenyl)(2,7-di-i-propyl-9-fluorenyl)zirconium dichloride, Dimethylmethylene(2,7-dimethyl-4,5-(1-methyl-benzo)-1-indenyl)(2,7-dimethyl-9-fluorenyl)zirconium dichloride, Dimethylmethylene(2-methyl-4,5-benzo-1-indenyl)(2,7-di-t-butyl-9-fluorenyl)zirconium dichloride, Dimethylmethylene(2-methyl-4,3-benzo-1-indenyl)(2,7-di-trimethylsilyl-9-fluorenyl)zirconium dichloride, Dimethylmethylene(2,6-dimethyl-4,5-benzo-1-indenyl) (2,7-di-t-butyl-9-fluorenyl)zirconium dichloride, Dimethylmethylene(2,6-dimethyl-4,5-benzo-1-indenyl) (2,7-di-trimethylsilyl-9-fluorenyl)zirconium dichloride, Dimethylmethylene(2,7-dimethyl-4,5-(2-methyl-benzo)-1-indenyl)(2,7-di-t-butyl-9-fluorenyl)zirconium dichloride, Dimethylmethylene(2,7-dimethyl-4,5-(2-methyl-benzo)-1-indenyl)(2,7-di-trimethylsilyl-9-fluorenyl)zirconium dichloride, Dimethylsilylene(2-methyl-4,5-benzo-1-indenyl)(2,7-di-t-butyl-9-fluorenyl)zirconium $\eta^4$-1-phenyl-1,3-pentadiene, Dimethylsilylene(2-methyl-4,5-benzo-1-indenyl)(2,7-di-trimethylsilyl-9-fluorenyl)zirconium $\eta^4$-1,4-diphenylbutadiene, Dimethylsilylene(2-methyl-4,5-benzo-1-indenyl)(2,7-dibromo-9-fluorenyl)zirconium $\eta^4$-2,4-hexadiene, Dimethylsilylene(2,6-dimethyl-4,5-benzo-1-indenyl)(2,7-di-t-butyl-9-fluorenyl)zirconium $\eta^4$-1,4-diphenyl-1,3-butadiene, Dimethylsilylene(2,6-dimethyl-4,5-benzo-1-indenyl)(2,7-di-trimethylsilyl-9-fluorenyl)zirconium $\eta^4$-3-methyl-1,3-pentadiene, Dimethylsilylene(2,6-dimethyl-4,5-benzo-1-indenyl)(2,7-dibromo-9-fluorenyl)zirconium $\eta^4$-2,4-hexadiene, Diphenylsilylene(2-methyl-4,5-benzo-1-indenyl)(2,7-ditrimethylsilyl-9-fluorenyl)zirconium dichloride, Dipenylsilylene(2,6-dimethyl-4,5-benzo-1-indenyl)(2,7-di-t-butyl-9-fluorenyl)zirconium dichloride, Diphenylsilylene(2,7-dimethyl-4,5-benzo-1-indenyl)(2,7-di-t-butyl-9-fluorenyl)zirconium dichloride, Diphenylsilylene(2,7-dimethyl-4,5-(2-methyl-benzo)-1-indenyl)(2,7-di-t-butyl-9-fluorenyl)zirconium dichloride, Methylphenylsilylene (2-methyl-4,5-benzo-1-indenyl)(2,7-di(trimethyl)silyl-9-fluorenyl)zirconium dichloride, Methylphenylsilylene(2,6-dimethyl-4,5-benzo-1-indenyl)(2,7-di-t-butyl-9-fluorenyl)zirconium dichloride, Methylphenylsilylene(2,7-dimethyl-4,5-benzo-1-indenyl)(2,7-di-t-butyl-9-fluorenyl)zirconium dichloride, and Methylphenylsilylene(2,7-dimethyl-4,5-(2-methyl-benzo)-1-indenyl)(2,7-di-t-butyl-9-fluorenyl)zirconium dichloride.

Also employable are compounds wherein zirconium is replaced with titanium or hafnium in the above-exemplified zirconium compounds.

Of the zirconium compounds as described above, the chemical structure of dimethylsilylene(2,7-dimethyl-4,5-(2-methyl-benzo)-1-indenyl)(2,7-di-t-butyl- 9-fluorenyl) z4zirconium dichloride is represented by the following formula:

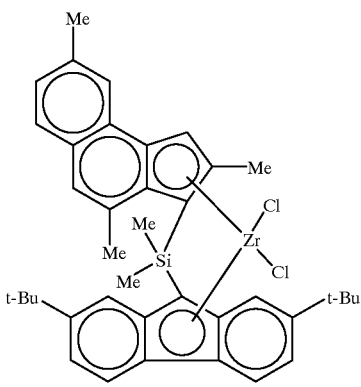

Me: methyl group
t-Bu: t-butyl group

The chemical structure of dimethylsilylene(2,6-dimethyl-4,3(1-methyl-benzo)-1-indenyl)(2,7-di-t-butyl-9-fluorenyl)zirconium dichloride is represented by the following formula:

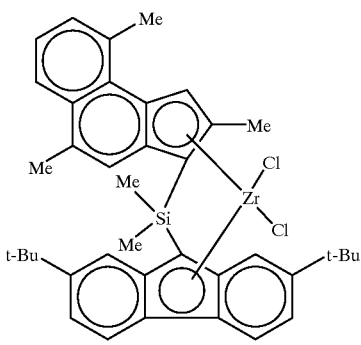

Me: methyl group
t-Bu: t-butyl group

The transition metal compounds (A-1) mentioned above may roe used in combination of two or more kinds.

The transition metal compound (A-1) used in the present invention is prepared, for example, as described below.

Firstly, a substituted fluorenyl anion (compound (i)) represented by the following formula (i) reacts with a compound (ii) represented by the following formula (ii) in solvent to prepare a compound (iii) represented by the following formula (iii).

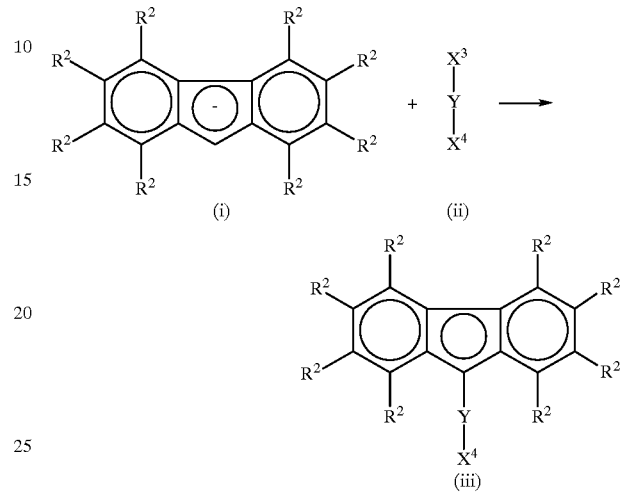

In the formula (i) $R^2$'s may be the same as or different from each other, and has the same meaning described for $R^2$ in the aforesaid formula (I)

In the formula (ii), Y has the same meaning described for $R^2$ in the aforesaid formula (I). $X^3$ and $X^4$ may be the same as or different from each other and are each hydrogen atom, a halogen atom, —OR group, —OCOR group, —SR group, —OSO$_2$R group, —SO$_2$R group, NRR' group (R and R' may be the same as or different from each other and are each hydrogen atom, a halogen atom, an alkyl group of 1 to 10 carbon atoms, an aryl group of 6 to 20 carbon atoms or an alkylaryl group of 7 to 30 carbon atoms).

In the formula (iii), $R^2$, Y and $X^4$ have the same meaning described for those in the aforesaid formulas (i) and (ii).

Examples of solvent applicable for aforesaid reaction include ethers, such as diethylether, tetrahydrofuran and dioxane; aromatic hydrocarbons, such as benzene, toluene and mesitylene; aliphatic hydrocarbons, such as pentane, hexane and heptane.

Of these, preferred are diethylether, tetrahydrofuran, toluene and hexane.

In the reaction of compound (i) and compound (ii), the compound (ii) is used in a molar ratio of from 0.5 to 200, preferably from 1 to 60 based on the compound (i) The solvent is used in a weight ratio of from 1 to 100, preferably from 1 to 20 based on compound (ii).

The compound (i) reacts with the compound (ii) at a reaction temperature of −78 to 150° C., preferably −78 to 50° C., for a reaction time of 0.1 to 50 hours, preferably 1 to 25 hours.

The compound (i) can be prepared by the reaction of a substituted fluorene and the base in the presence or absence of solvent.

Examples of base include elemental metals, such as metallic sodium, metallic potassium and metallic lithium; hydride compounds, such as sodium hydride and potassium hydride; organic lithium compounds, such as methyl lithium and n-butyl lithium. Of these, preferred are metallic sodium, sodium hydride and n-butyl lithium, especially preferred is n-butyl lithium.

Examples of solvent applicable for the reaction of substituted fluorene and base include the same solvents used the reaction of compound (i) and compound (ii) Of these, preferred are diethylether, tetrahydrofuran, toluene and hexane, especially preferred are diethylether and toluene.

In the reaction of substituted fluorene and base, the base is used in a molar ratio of from 0.5 to 200, preferably from 1 to 60 based on the substituted fluorene. The solvent is used in a weight ratio of from 1 to 100, preferably from 1 to 20 based on the substituted fluorene.

The temperature of the reaction of the substituted fluorene and the base is in the range of −78 to 150° C., preferably −78 to 50° C., and the reaction time is in the range of 0.1 to 50 hours, preferably 1 to 25 hours, Then, the compound of the general formula (iii) (the compound (iii)) and a substituted indenyl anion of the following general formula (iv) (the compound (iv)) are reacted to prepare the compound of the following general formula (v).

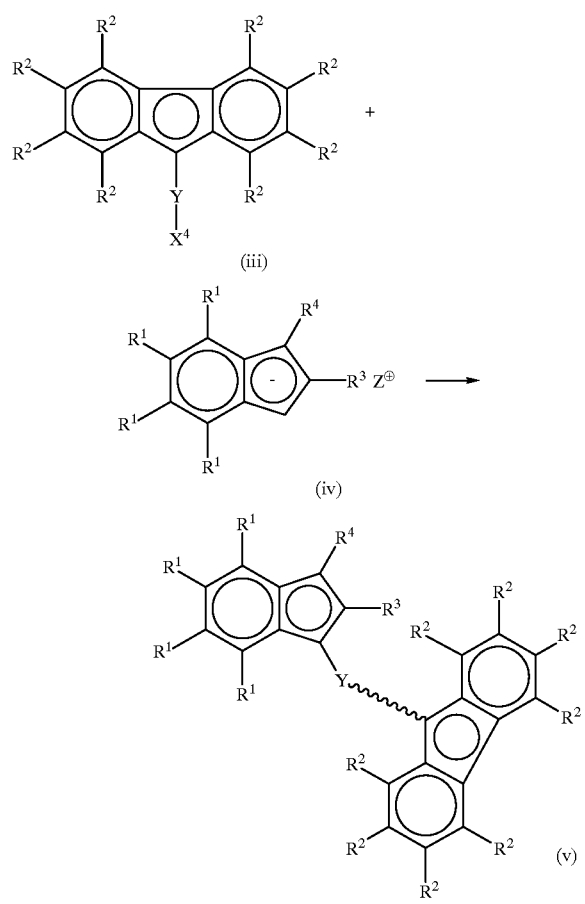

In the above formula (iv), each of $R^1$, $R^3$ and $R^4$ is the same as each of $R^1$, $R^3$ and $R^4$ of the above formula (I), Z is an alkali metal such as lithium, sodium and potassium.

In the above formula (v), each of $R^1$, $R^2$, $R^3$, $R^4$ and Y is the same as each of $R^1$, $R^2$, $R^3$, $R^4$ and Y of the above formula (I).

In the reaction of the compound (iii) and the compound (iv), the compound (iii) is used in the amount of 0.5 to 10, preferably 0.5 to 5 by mol based on the amount of the compound (iv) used, and a solvent is used in the amount of 1 to 100, preferably 1 to 20 by weight based on the amount of the compound (iv) used .

The temperature of the reaction of the compound (iii) and the compound (iv) is in the range of −75 to 150° C., preferably −78 to 50° C., and the reaction time is in the range of 0.1 to 50 hours, preferably 1 to 25 hours.

The substitute indenyl-substituted fluorenyl bridging compound of the formula (v) can be obtained by reacting the compound (iii) with the compound (iv) under the above conditions.

The compound (iv) can be obtained by reacting the substituted indene and the base in the presence or absence of solvent.

The base used for the reaction includes the same bases as used for preparing the substituted fluorenyl anion. Of these, sodium metal, sodium hydride and n-butyllithium are preferable, in particular, n-butyllithium is preferable.

The solvent used for the reaction includes the same solvent as used for reacting the compound (i) and the compound (ii). Of these, diethyl ether, tetrahydrofuran, toluene and hexane are preferable, in particular, diethyl ether and toluene are preferable.

In the reaction of the substituted indene and the base, the base is used in the amount of 0.5 to 2.0, preferably 0.90 to 1.5 by mol based on the amount of the substituted indene used, and tie solvent is used in the amount of 1 to 100, preferably 1 to 20 by weight based on the amount of the substituted indene used.

The temperature of the reaction of the substituted indene and the base is in the range of −78 to 150° C., preferably −78 to 50° C., and the reaction time is in the range of 0.5 to 50 hours, preferably 1 to 25 hours.

The transition metal compound of the formula (I) of the invention can be prepared by reacting an anion of the substituted indenyl-substituted fluorenyl bridging compound with a compound of the following general formula (vii)

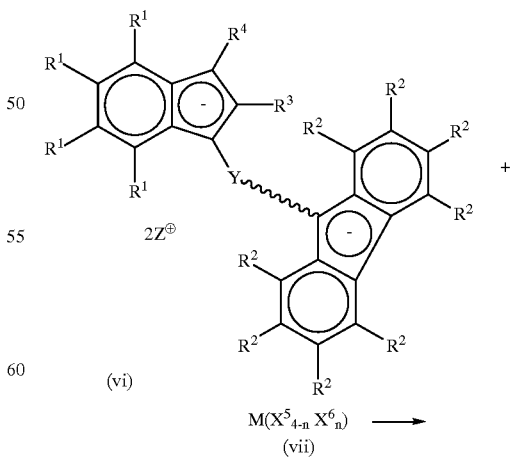

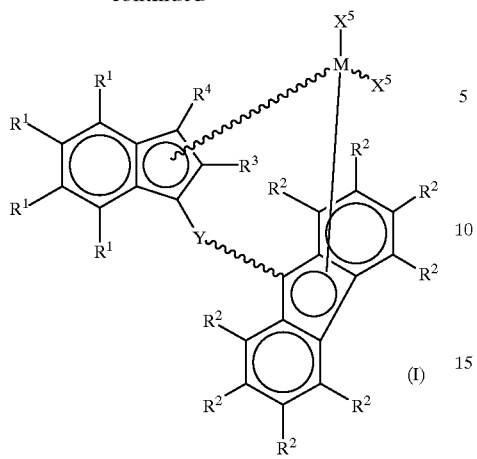

(I)

In the above formula (vi), each of $R^1$, $R^2$, $R^3$, $R^4$ and Y is the same as each of $R^1$, $R^2$, $R^3$, $R^4$ and Y of the above formula (I).

In the above formula (vii), M is the same as in the formula (I); $X^5$ may be the same as or different from each other, and are each hydrogen atom, a halogen atom, —OR group, —OCOR group, —SR group, —OSO$_2$R group or —SO$_2$R group; $X^6$ are each hydrogen atom, a halogen atom, —OR group, —OCOR group, —SR group, —OSO$_2$R group, —SO$_2$R group or —NRR' group (R and R' may be the same as or different from each other, and are each hydrogen atom, a halogen atom, an alkyl group of 1 to 10 carbon atoms, an aryl group of 6 to 20 carbon atoms or an alkylaryl group of 7 to 30 carbon atoms); n is 1 or 2. When n is 2, $X^6$ may be the same as or different from each other.

In the reaction of the substituted indenyl-substituted fluorenyl bridging compound of the formula (vi) (the compound (vi)) and a compound of the formula (vii) (the compound (vii)), the compound (vii) is used in the amount of 0.1 to 200, preferably 0.5 to 5.0 by mol based on the amount of the compound (vi) used, and a solvent is used in amount of 1 to 100, preferably 1 to 20 by weight based on the amount of the substituted indenyl anion used.

The temperature of the reaction of the compound (vi) and the compound (vii) is in the range of −78 to 150° C., preferably −78 to 50° C., and the reaction time is in the range of 0.1 to 50 hours, preferably 1 to 25 hours.

The compound (vi) can be obtained by reacting the substituted indenyl-substituted fluorenyl bridging compound (the compound (v)) with the base in the presence or absence of solvent.

The base used for the reaction includes the same base as used for preparing the substituted fluorenyl anion. Of these, sodium metal, sodium hydride and n-butyllithium are preferable, in particular, n-butyllithium is preferable The solvent used for the reaction includes the same solvent as used for the reaction of the compound (i) and the compound (ii). Of these, diethyl ether, tetrahydrofuran, toluene and hexane are preferable, in particular, diethyl ether and toluene are preferable.

In the reaction of the compound (v) and the base, the base is used in amount of 1.0 to 10.00, preferably 1.5 to 3.0 by mol based on the amount of the compound (v) used, and the solvent is used in the amount of 1 to 100, preferably 1 to 20 by weight based on the amount of the compound (v).

The temperature of the reaction of the substituted indene and the base is in the range of −78 to 150° C., preferably −78 to 50° C., and the reaction time is in the range of 0.1 to 50 hours, preferably 1 to 25 hours.

The transition metal compound obtained as above mentioned can be purified by crystallizing the compound after removing an inorganic salt by the ordinary procedure.

The transition metal compound (A-1) can be also prepared as described below. Firstly, the compound (iv) and the compound (ii) are reacted to prepare a compound of the following formula (viii) (the compound (viii)).

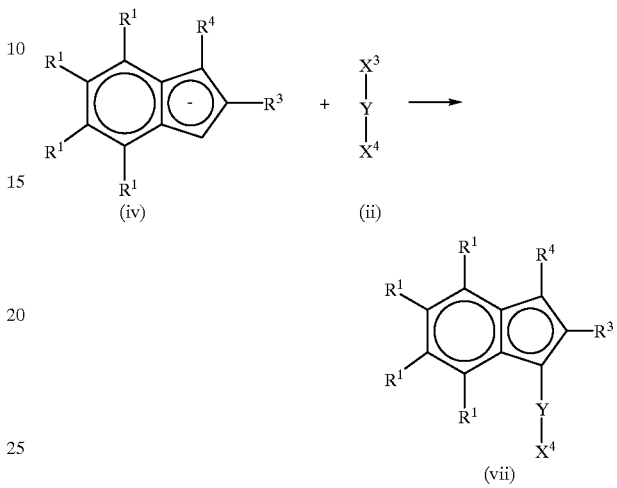

The compound (viii) and the substituted fluorenyl anion (the compound (i)) are reacted to obtain a substituted indenyl-substituted fluorenyl bridging compound (the compound (v)) Subsequently, a compound (vi) which is obtained by anionizing the compound (v) and the compound (vii) are reacted to obtain the transition metal compound (A-1). In this process, the same conditions as above mentioned are employable as each of reaction conditions.

Moreover, the transition metal compound (A-1) can be also prepared as described below. Firstly, a substituted indene of the following formula (ix) (the compound (ix)) and a substituted ketone of the following formula (x) (the compound (x)) are reacted to prepare a compound of the following formula (xi) (the compound (xi)).

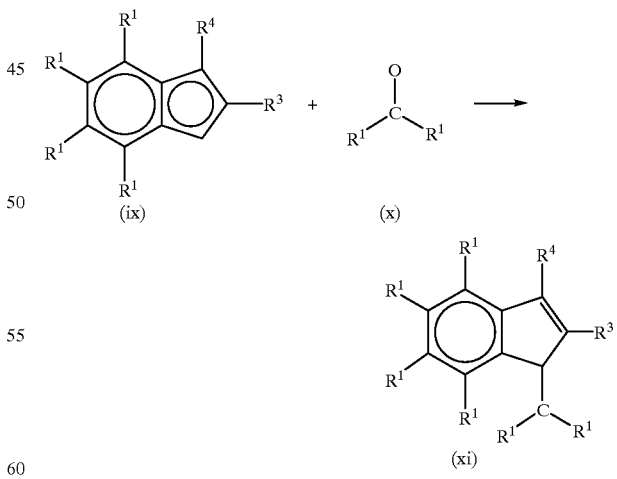

The reaction is conducted so that the base as mentioned above is employed, that the substituted indene is changed into a substituted indenyl anion and that the substituted ketone is then added in the amount of 0.1 to 100, preferably 0.1 to 20 by mol based on the amount of the substituted indenyl anion used.

The compound (xi) thus obtained and the substituted fluorenyl anion (the compound (i)) are reacted to obtain a substituted indenyl-substituted fluorenyl bridging compound (the compound (v)). In the reaction of the compound (xi) and the compound (i) the compound (i) is used in the amount of the range of 0.1 to 100, preferably 0.5 to 5.0 by mol based on the amount of the compound (xi) used. Subsequently, an anion of the substituted indenyl-substituted fluorenyl bridging compound and the compound (vii) are reacted in a solvent to obtain the transition metal compound (A-1). In this process, the same conditions as above mentioned are employable as each of reaction conditions.

The organoaluminum oxy-compound (B-1) used in the invention may be aluminoxane conventionally known or a benzene-insoluble organoaluminum oxy-compound exemplified in Japanese Patent Laid-Open Publication No. 78687/1990.

The conventionally known aluminoxane call be prepared by, for example, the following procedures.

(1) An organoaluminum compound such as trialkylaluminum is added to a hydrocarbon medium suspension of compounds containing adsorbed water or salts containing water of crystallization, e.g., magnesium chloride hydrate copper sulfate hydrate, aluminum sulfate hydrate, nickel sulfate hydrate or cerous chloride hydrate, so as to allow the organoaluminum compound to react with the adsorbed water or the water of crystallization.

(2) Water, ice or water vapor is allowed to directly act on an organoaluminum compound such as trialkylaluminum in a medium such as benzene, toluene, ethyl ether or tetrahydrofuran.

(3) An organotin oxide such as dimethyltin oxide or dibutyltin oxide is allowed to react with an organoaluminum compound such as trialkylaluminum in a medium such as decane, benzene or toluene.

The aluminoxane may contain a small amount of an organometallic component. Further, it is also possible that the solvent or the unreacted organoaluminum compound is distilled off from the recovered solution of aluminoxane and the remainder is redissolved in a solvent.

Examples of the organoaluminum compounds used for preparing the aluminoxane include:

trialkylaluminums, such as trimethylaluminum, triethylaluminum, tripropylaluminum, triisopropylaluminum, tri-n-butylaluminum, triisobutylaluminum, tri-sec-butylaluminum, tri-tert-butylaluminum, tripentylaluminum, tritexylaluminum, trioctylaluminum and tritexylaluminum;

tricycloalkylaluminums, such as tricyclohexylaluminum and tricyclooctylaluninum;

dialkylaluminum halides, such as dimethylaluminum chloride, diethylaluminum chloride, diethylaluminum bromide and diisobutylalurninum chloride;

dialkylaluminum hydrides, such as diethylaluminum hydride and diisobutylalurninum hydride;

dialkylaluminum alkoxides, such as dimethylaluminum methoxide and diethylaluminum ethoxide; and dialkylaluminum aryloxides, such as diethylaluminum phenoxide.

Of these, trialkylaluminums and tricycloalkylaluminums are particularly preferable.

Also employable as the organoaluminum compound for preparing the aluminoxane is isoprenylaluminum represented by the formula $(i\text{-}C_4H_9)_xAl_y(C_5H_{10})_z$ (wherein x, y, z are each a positive number, and $z \geq 2x$)

The organoaluminum compounds mentioned above can be used in combination of two or more kinds.

Examples of the solvents used for preparing the aluminoxane include:

aromatic hydrocarbons, such as benzene, toluene, xylene, cumene and cymene;

aliphatic hydrocarbons, such as pentane, hexane, heptane, octane, decane, dodecane, hexadecane and octadecane;

alicyclic hydrocarbons, such as cyclopentane, cyclohexane, cyclooctane and methylcyclopentene;

petroleum fractions, such as gasoline, kerosine and gas oil; and halides of these aromatic, aliphatic and alicyclic hydrocarbons, particularly chlorides and bromides thereof.

Also employable are ethers such as ethyl ether and tetrahydrofuran. Of the solvents, particularly preferable are aromatic hydrocarbons.

The compound (B-2) which reacts with the transition metal compound (A-1) to form an ion pair (sometimes referred to as "ionized ionic compound" hereinafter), that is used in the invention, includes Lewis acid, ionic compounds, borane compounds and carborane compounds described in National Publications of International Patent No. 501950/1989 and No. 502036/1989, Japanese Patent Laid-Open Publication No, 179005/1991, No. 179006/1991, No. 207703/1991 and No. 207704/1991, and U.S. Pat. No. 5,321,106.

The Lewis acid includes magnesium-containing Lewis acid, aluminum-containing Lewis acid and boron-containing Lewis acid. Of these, boron-containing Lewis acid is preferable.

The Lewis acid which contains a boron atom is, for example, a compound represented by the following formula (III):

$$BR^{11}R^{12}R^{13} \tag{III}$$

wherein $R^{11}$, $R^{12}$ and $R^{13}$ may be the same as or different from each other, and are each a phenyl group which may have a substituent such as fluorine, methyl or trifluoromethyl, or a fluorine atom.

Examples of the compounds represented by the above formula (III) include trifluoroboron, triphenylboron, tris (4-fluorophenyl) boron, tris (3,5-difluorophenyl)boron, tris (4-fluoromethylphenyl)boron, tris (pentafluoroethyl) boron, tris (p-tolyl) boron, tris (o-tolyl)boron, tris(3,5-dimethylphenyl)boron and tris{3,5-di(trifluoromethylphenyl)}boron. Of these, particularly preferable is tris(pentafluorophenyl)boron.

The ionic compound used in the invention is a salt comprising a cationic compound and an anionic compound. The anion reacts with the transition metal compound (A-1) to render the compound (A-1) cationic and to form an ion pair, thereby to stabilize the transition metal cation seed. Examples of such anions include organoboron compound anion, organoarsenic compound anion and organoaluminum compound anion. Preferred anions are relatively bulky and stabilize the transition metal cation seed. Examples of the cations include metallic cation, organometallic cation, carbonium cation, tripium cation, oxonium cation, sulfonium cation, phosphonium cation and ammonium cation. More specifically, there can be mentioned triphenylcarbenium cation, tributylammonium cation, N,N-dimethylammonium cation, ferrocenium cation, etc.

Of these, preferable are ionic compounds containing a boron compound as anion, and examples thereof include:

trialkyl-substituted ammonium salts, such as triethylammoniumtetra(phenyl)boron, tripropylammoniumtetra (phenyl)boron, tri(n-butyl)ammoniumtetra (phenyl)boron, trimethylammoniumtetra(p-tolyl) boron, trimethylammoniumtetra(o-tolyl)boron, tributylammoniumtetra(pentafluorophenyl)boron, tripropylammoniumtetra(o,p-dimethylphenyl)boron, tributylammoniumtetra(m,m-dimethylphenyl)boron, tributylammoniumtetra(p-trifluoromethylphenyl) boron, tri(n-butyl)ammoniumtetra(o-tolyl)boron and tri(n-butyl)ammoniumtetra(4-fluorophenyl)boron;

N,N,-dialkylaniline salts, such as N,N-dimethylaniliniumtetra(phenyl)boron, N,N-diethylaniliniumtetra(phenyl)boron and N,N-2,4,6-pentamethylaniliniumtetra(phenyl)boron;

dialkylammonium salts, such as di(n-propyl)ammoniumtetra(pentaluorophenyl)boron and dicyclohexylammionumtetra(phenyl)boron; and triarylphosphonium salts, such as triphenylphosphoniumtetra(phenyl)boron, tri(methylphenyl)phosphoniumtetra(phenyl)boron and tri(dimethylphenyl)phosphoniumtetra(phenyl)boron.

As the ionic compounds containing a boron atom, triphenylcarbeniumtetakis(pentafluorophenyl)borate, N,N-dimethylaniliniumzetrakis(pentafluorophenyl)borate and ferroceniumtetra(pentafluorophenyl)borate are also employable.

Further, the following compounds are also employable as the ionic compounds containing a boron atom. (In the ionic compounds enumerated below, the counter ion is tri(n-butyl) ammonium, but the counter ion is in no way limited thereto.)

That is, there can be mentioned:

salts of anions, such as bis[tri(n-butyl)ammonium] nonaborate, bis[tri(n-butyl)ammonium]decaborate, bis[tri(n-butyl)ammonium]undecaborate, bis[tri(n-butyl)ammonium]dodecaborate, bis[tri(n-butyl)ammonium]decachlorodecaborate, bis[tri(n-butyl)ammonium]dodecachlorododecaborate, tri(n-butyl)ammonium-1-carbadecaborate, tri(n-butyl)ammonium-1-carbaundecaborate, tri(n-butyl)ammonium-1-carbadodecaborate, tri(n-butyl)ammonium-1-trimethylsilyl-1-carbadecaborate and tri(n-butyl)ammoniumbromo-1-carbadodecaborate;

borane compounds, carborane complex compounds and salts of carborane anions, such as decaborane(14), 7,8-dicarbaundecaborane(13), 2,7-dicarbaundecaborane(13), undecahydride-7,8-dimethyl-7,6-dicarbaundecaborane, dodecahydride-11-methyl-2,7-dicarbaundecaborane, tri(n-butyl)ammonium-6-carbadecaborate(14), tri(n-butyl)ammonium-6-carbadecaborate(12), tri(n-butyl)ammonium-7-carbaurdecaoorate(13), tri(n-butyl)ammonium-7,8-dicarbaundecalorate(12), tri(n-butyl)ammonium-2,9-dicarbaundecaborate(12), tri(n-butyl)ammoniumdodecalydride-8-methyl-7,9-dicarbaundecaborate, tri(n-butyl)ammoniumundecahydride-8-ethyl-7,9-dicarbaundecaborate, tri(n-butyl)ammoniumurndecahydride-8-butyl-7,9-dicarbaundecaborate, tri(n-butyl)ammoniumundecahydride-8-allyl-7,9-dicarbaundecaborate, tri(n-butyl)ammoniumundecahydride-9-trimethylsilyl-7,8-dicarbaundecaborate and tri(n-butyl)ammoniumundecahydride-4,6-dibromo-7-carbaundecaborate;and carborane compounds and salts of carboranes, such as 4-carbancnaborane(14), 1,3-dicarbanonaborane(13), 6,9-dicarbadecaborane(14), dodecahydride-1-phenyl-1,3-dicarbanonaborane, dodecahydride-1-methyl-1,3-dicarbanonaborane and undecahydride-1,3-dimethyl-1,3-dicarbanonaborane.

Furthermore, the following salts of metallic carboranes and metallic borane anions are also employable as the ionic compounds containing a baron atom. (In the ionic compounds enumerated below, the counter ion is tri(n-butyl) ammonium, but the counter ion is in no way limited thereto.)

That is, there can be mentioned tri(n-butyl)ammoniumbis(nonahydride-1,3-dicarbanonaborate)cobaltate(III), tri(n-butyl)ammoniumbis(undecahydride-7,8-dicarbaunadecaborate)ferrate(III), tri(n-buiyl)ammoniumbis(undecahydride-7,8-dicarlaundecaborate)cobaltate(III), tri(n-butyl)ammoniumbis(undecahydride-7,8-dicarbaundecaborate)nickelate(III), tri(n-butyl)ammoniumbis(undecatydride-7,8-dicarbaundecaborate)cuprate(III), tri(n-butyl)ammoniumbis(undecahydride-7,8-dicarbaundecaborate)aurate(III), tri(n-butyl)ammoniumbis(nonahydride-7,8-dimethyl-7,8-dicarbaundecaborate)ferrate(III), tri(n-butyl)ammoniumbis(nonahydride-7,8-dimethyl-1,8-dicarbaundecaborate)chromate(III), tri(n-butyl)ammoniumbis(tribromooctahydrde-7,8-dicarbaundecaborate)cobaltate(III), tri(n-butyl)ammoniumbis(dodecahydridedicarbadodecaborate)cobaltate(III), bis [tri(n-butyl)ammonium]bis(dodecahydridedodecaborate)nickelate(III), tris[tri(n-butyl)ammonium]bis(undecahydride-7-carbaundecaborate)chromate(III), bis[tri(n-butyl)ammonium]bis(undecahydride-7-carbaundecaborate)manganate(IV), bis[tri(n-butyl)ammonium]bis(undecahydride-7-carbaundecaborate)cobaltate(III), bis[tri(n-butyl)ammonium]bis(undecahydride-7-carbaundecaborate) nickelate(IV), triphenylcarbenium tetrakis{(2,3,5,6-tetrafluoro-4-triisopropylsilyl)pheny}borate, N,N-dimethylanirinium tetrakis{(2,3,5, 6-tetrafluoro-4-triisopropylsilyl)phenyl}borate, triphenylcarbenium tetrakis{(2,3,5,6-tetrafluoro-4-dimethyl-t-butylsilyl) phenyl}borate, N,N-dimethylanirinium tetrakis{(2,3,5,6-tetrafluoro- 4-dimethyl-t-butylsilyl)phenyl}borate, triphenylcarbenium bis(octahydrobiphenylene)borate, N,N-dimethylanirinium bis(octahydrobiphenylene)borate, triphenylcarbenium (octafluoro-1,1'-spiro)biboronole and N,N-dimethylanirinum (octafluoro-1,1'-spiro)biboronole.

The ionized ionic compounds mentioned above can be used in combination of two or more kinds.

The olefin polymerization catalyst of the invention may optionally contain the below-described organoaluminum compound (C) in addition to the above-mentioned components.

The organoaluminum compound (C) optionally used in the invention can be represented by, for example, the following formula (IV):

$$R^a{}_n AlX_{3-n} \qquad (IV)$$

wherein $R^a$ is a hydrocarbon group of 1 to 12 carbon atoms, X is a halogen atom or hydrogen, and n is 1 to 3.

In the formula (IV), $R^a$ is a hydrocarbon group of 1 to 12 carbon atoms, e.g., an alkyl group, a cycloalkyl group or an aryl group. Particular examples of the groups include methyl, ethyl, n-propyl, isopropyl, isobutyl, pentyl, hexyl, octyl, cyclopentyl, cyclohexyl, phenyl and tolyl.

Examples of such organoaluminum compounds include:

trialkylaluminums, such as trimethylaluminum, triethylaluminum, triisopropylaluminum, triisobutylaluminum, trioctylaluminum and tri-2-ethylhexylaluminum;

alkenylaluminums, such as isoprenylaluminum;

dialkylaluminum halides, such as dimethylaluminum chloride, diethylaluminum chloride, diisopropylaluminum chloride, disobutylaluminum chloride and dimethylaluminum bromide;

alkylaluminun sesquihalides, such as methylaluminuim sesquichloride, ethylaluminum sesquichloride, isopropylaluminum sesquichlorice, butylaluminum sesquichloride and ethylaluminum sesquibromide;

alkylaluminum dihalides, such as methylaluminum dichlorlde, ethylaluminum dichloride, isopropylaluminum dichloride and ethylaluminum dibromide; and alkylaluminum hydrides, such as diethylaluminum hydride and diisobutylaluminum hydride.

Also employable as the organoaluminum compound (C) is a compound represented by the following formula (V)

$$R^a AlY_{3-n} \qquad (V)$$

wherein $R^a$ is the same as above,

Y is —$OR^b$ group, —$OSiR^c_3$ group, —$OAlR^d_2$ group, —$NR^e_2$ group, —$SiR^f_3$ group or —$N(R^g)AlR^h_2$ group, n is 1 to 2, $R^b$, $R^c$, $R^d$ and $R^h$ are each methyl, ethyl, isopropyl, isobutyl, cyclchexyl, phenyl or the like, $R^e$ is hydrogen, methyl, ethyl, isopropyl, phenyl, trimethylsilyl or the like, and $R^f$ and $R^g$ are each methyl, ethyl or the like.

Examples of such organcaluminum compounds include:
(i) compounds of the formula $R^a_n Al(OR^b)_{3-n}$, e.g., dimetylaluminum methoxide, diethylaluminum ethoxide and diisobutylaluminum methoxide;
(ii) compounds of the formula $R^a_n Al(OSiR^c_3)_{3-n}$ e.g., $(C_2H_5)_2Al(OSi(CH_3)_3)$, $(iso-C_4H_9)_2Al(OSi(CH_3)_3)$ and $(iso-C_4H_9)_2Al(OSi(C_2H_5)_3)$;
(iii) compounds of the formula $R^a_n Al(OAlR^d_2)_{3-n}$, e.g., $(C_2H_5)_2Al(OAl(C_2H_5)_2)$ and $(iso-C_4H_9)_2Al(OAl(iso-C_4H_9)_2)$;
(iv) compounds of the formula $R^a_n Al(NR^e_2)_{3-n}$, e.g., $(CH_3)_2Al(N(C_2H_5)_2)$, $(C_2H_5)_2Al(NH(CH_3))$, $(CH_3)_2Al(NH(C_2H_5))$, $(C_2H_5)_2Al[N(Si(CH_3)_3)_2]$ and $(iso-C_4H_9)_2Al[N(Si(CH_3)_3)_2]$; and
(v) compounds of the formula $R^a_n Al(SiR^f_3)_{3-n}$, e.g., $(iso-C_4H_9)_2Al(Si(CH_3)_3)$.

Of these, preferable are organoaluminum compounds of the formulas $R^a_3Al$, $R^a_n Al(OR^b)_{3-n}$, and $R^a_n Al(OAlR^d_2)_{3-n}$, and particularly preferable are compounds of said formulas wherein $R^a$ is an isoalkyl group and n is 2. The organoaluminum compounds mentioned above can be used in combination of two or more kinds.

The olefin polymerization catalyst according to the invention may be a solid catalyst wherein at least one component of the component (A-1), the component (B-1), the component (B-2) and the component (C) is supported on a fine particle carrier.

The olefin polymerization catalyst according to the invention may be a prepolymerized catalyst comprising a fine particle carrier, the component (A-1), the component (B-1) (or the component (B-2)), an olefin polymer produced by prepolymerization, and optionally, the component (C)

The fine particle carrier used in the solid catalyst and the prepolymerized catalyst is an inorganic or organic compound, and is a particulate or granular solid having a particle diameter of 10 to 300 μm, preferably 20 to 200 μm.

The inorganic carrier is preferably a porous oxide, and examples thereof include $SiO_2$, $Al_2O_3$, MgO, $ZrO_2$, $TiO_2$, $B_2O_3$, CaO, ZnO, BaO, $ThO_2$ and mixtures thereof such as $SiO_2$—MgO, $SiO_2$—$Al_2O_3$, $SiO_2$—$TiO_2$, $SiO_2$—$V_2O_5$, $SiO_2$—$Cr_2O_3$ and $SiO_2$—$TiO_2$—MgO. Of these, preferable are those containing at least one component selected from the group consisting of $SiO_2$ and $Al_2O_3$ as their major component.

The above-mentioned inorganic oxides may contain carbonates, sulfates, nitrates and oxides, e.g., $Na_2CO_3$, $K_2CO_3$, $CaCO_3$, $MgCO_3$, $Na_2SO_4$, $Al_2(SO_4)_3$, $BaSO_4$, $KNO_3$, $Mg(NO_3)_2$, $Al(NO_3)_3$, $Na_2O$, $K_2O$ and $Li_2$, in small amounts.

The properties of the fine particle carrier vary depending on the kind thereof and the process for the preparation thereof, but preferably used in the invention is a carrier having a specific surface area of 50 to 1,000 m$^2$/g, preferably 100 to 700 m$^2$/g, and a pore volume of 0.3 to 2.5 cm$^3$/g. If des red, the fine particle carrier is calcined at a temperature of 100 to 1,000° C., preferably 150 to 700° C., prior to use.

Also employable as the fine particle carrier is a granular or particulate solid of an organic compound having a particle diameter of 10 to 300 μm Examples of such organic compounds include (co)polymers produced using, as their main component, an α-olefin of 2 to 14 carbon atoms such as ethylene, propylene, 1-butene or 4-methyl-1-pentene, and (co)polymers produced using, as their main component, vinylcyclohexane or styrene.

In FIG. 1, steps for preparing the olefin polymerization catalyst of the invention are shown.

In the first process for preparing an olefin polymer according to the invention, an olefin is homopolymerized or two or more kinds of olefins are copolymerized in. the presence of the olefin polymerization catalyst formed from the transition metal compound (A-1), the organoaluminum oxy-compound and/or the ionized ionic compound (B), and optionally, the organoaluminum compound (C)

Examples of the olefins used in the invention include chain or branched α-olefins of 3 to 20 carbon atoms, such as ethylene, propylene, 1-butene, 1-pentene, 1-hexene, 4-methyl-1-pentene, 3-methyl-1-pentene, 1-teptene, 1-octene, 1-nonene, 1-decene, 1-undecene, 1-dodecene, 1-tetradecene, 1-hexadecene and 1-octadecene.

Also employable are olefins having an aliphatic ring or an aromatic ring, such as cyclopentene, cycloheptene, norbornene, 5-methyl-2-norbornene, tetracyclododecene, 2-methyl-1,4,5,8-dimethano-1,2,3,4,4a,5,8a-octahydronaphthalene, styrene and vinylcyclohexane.

Together with the olefins, various polyenes can be copolymerized. Examples of the polyenes include chain or cyclic dienes, such as butadiene, isoprene, 1,4-hexadiene, dicyclopentadiene, 5-ethylidene-2-norbornene and 7-methyl-1,6-octadiene; chain or cyclic trienes, such as 6,10 dimethyl-1,5,9-undecatriene and 5,9-dimethyl-1,4,8-decatriene; and chain or cyclic tetraenes, such as 6,10,14-trimethyl-1,5,9,13-pentadecatetraene and 5,9,13-trimethyl-1,4,8,12-tetradecatriene.

In the (co)polymerization of the olefin, the transition metal compound (A-1) is used in an amount of usually about 0.00005 to 0.1 mmol, preferably about 0.0001 to 0.05 mmol, in terms of the transition metal atom, based on 1 liter of the polymerization volume.

The organoaluminum oxy-compound (B-1) is used in such an amount that the amount of the aluminum atom becomes usually about 1 to 10,000 mol, preferably 10 to 5,000 mol, based on 1 mol of the transition metal atom.

The ionized ionic compound (B-2) is used in such an amount that the amount of the boron atom becomes usually about 0.5 to 20 mol, preferably 1 to 10 mol, based on 1 mol of the transition metal atom.

The organoaluminum compound (C) is used, if necessary, in an amount of usually about 0 to 200 mol, preferably about 0 to 100 mol, based on 1 mol of the aluminum atom in the organoaluminum oxy-compound (B-1) The compound (C) is used, if necessary, in an amount o usually about 0 to 1,000 mol, preferably about 0 to 500 mol, based on 1 mol of the boron atom in the ionized ionic compound (B-2).

The (co)polymerization of the olefin can be carried out by any of a liquid phase polymerization process such as suspension polymerization process or solution polymerization process, a gas phase polymerization process and a high-pressure process.

In the liquid phase polymerization process, inert hydrocarbon media can be employed. Examples of the inert hydrocarbon media include aliphatic hydrocarbons, such as propane, butane, pentane, hexane, heptane, octane, decane, dodecane and kerosine; alicyclic hydrocarbons, Such as cyclopentane, cyclohexane and methylcyclopentene; aromatic hydrocarbons, such as benzene, toluene and xylene; and halogenated hydrocarbons, such as ethylene chloride, chlorobenzene and dichloromethane. The olefin itself can be used as a solvent. These solvents may be used in combination of two or more kinds, In the suspension polymerization process, the polymerization temperature is in the range of usually –50 to 100° C., preferably 0 to 90° C.; in the solution polymerization process, the polymerization temperature is in the range of usually 0 to 300° C., preferably 20 to 250° C.; and in the gas phase polymerization process, the polymerization temperature is in :he range of usually 0 to 120° C., preferably 20 to 100° C. In the high-pressure process, fine polymerization temperature is in the range of usually 50 to 1,000° C., preferably 100 to 500° C. The polymerization pressure is in the range of atmospheric pressure to 100 kg/cm$^2$, preferably atmospheric pressure to 50 kg/cm$^2$. In the high-pressure process, the polymerization pressure is in the range of usually 100 to 10,000 kg/cm$^2$, preferably 500 to 3,000 kg/cm$^2$. The polymerization reaction can be carried out by any of batchwise, semi-continuous and continuous processes. The copolymerization can be conducted in two or more stages under different reaction conditions.

The molecular weight of the resulting olefin polymer can be modified by allowing hydrogen to exist in the polymerization system or varying the polymerization temperature or the polymerization pressure.

In the present invention, the transition metal compound (A-1) which contains, as a ligand, an indenyl group having a specific substituent at the specific position is used as a transition metal catalyst component, and therefore there can be obtained an olefin (co)polymer of higher molecular weight and an olefin copolymer of higher comonomer content as compared with the case of using an olefin polymerization catalyst which uses as its catalyst component a transition metal compound not having such substituent.

The first olefin polymer of the invention obtained by the above process has a melt flow rate (MFR) of usually 0.01 to 200 g/10 min, preferably 0.03 to 100 g/10 min, an intrinsic viscosity [η] of usually 0.5 to 6.0 dl/g, preferably 1.0 to 4.0 dl/g, and a density of usually 0.85 to 0.95 g/cm$^3$, preferably 0.85 to 0.94 g/cm$^3$.

The molecular weight distribution (Mw/Mn, Mw: weight-average molecular weight, Mn: number-average molecular weight) measured by GPC is in the range of 1.5 to 4.

The molecular weight distribution (Mw/Mn) was measured in the following manner using a measuring device of GPC-150C produced by Millipore Co.

This measurement was carried out using a column of TSK-GNP-HT having a diameter of 72 mm and a length of 600 mm at a column temperature of 140° C. In this measurement, 500 microliters of a sample having a concentration of 0.1% by weight was introduced into the column in which o-dichlorobenzene (available from Wako Junyaku Kogyo K.K.) as a mobile phase was moved at a moving rate of 1.0 ml/min. In the mobile phase, 0.025% by weight of BHT (available from Takeda Chemical Industries, Ltd.) was contained as an antioxidant. A differential refractometer was used as a detector. With respect to the standard polystyrene of Mw<1,000 and Mw>4×10$^6$, those available from Toso Co. were used, and with respect to the standard polystyrene of 1,000<Mw<4×10$^6$, these available from Pressure Chemical Co. were used.

The olefin polymer obtained by the above process is characterized by having a narrow molecular weight distribution and a narrow composition distribution.

The first process for preparing an olefin polymer according to the invention is favorably used for preparing particularly an ethylene polymer and a propylene polymer.

For preparing the ethylene polymer, ethylene is homopolymerized or ethylene and an α-olefin of 3 to 20 carbon atoms are copolymerized in the presence of the aforesaid olefin polymerization catalyst. The term "ethylene polymer" used herein means both an ethylene homopolymer and an ethylene-α-olefin copolymer.

Examples of the c-olefins of 3 to 20 carbon atoms include the aforementioned α-olefins of 2 to 20 carbon atoms, other than ethylene. Of these, propylene, 1-butene, 1-hexene and 1-octene are preferably employed.

Together with ethylene and the α-olefin of 3 to 20 carbon atoms, the same polyenes as described above are copolymerizable.

The polymerization conditions for preparing the ethylene polymer are the same as those described above.

The first ethylene polymer obtained by the above process has an ethylene/a-olefin ratio of usually 55/45 to 100/2, preferably 60/40 to 100/5.

The first ethylene polymer has MFR of usually 0.01 to 200 g/10 min, preferably 0.03 to 100 g/10 min, an intrinsic viscosity [η] of usually 0.5 to 5.0 dl/g, preferably 1.0 to 4.0 dl/g, and a density of usually 0.85 to 0.95 g/cm$^3$, preferably 0.86 to 0.94 g/cm$^3$.

For preparing the propylene polymer, propylene is homopolymerized or propylene and an α-olefin other than propylene are copolymerized in the presence of the aforesaid olefin polymerization catalyst. The term "propylene polymer" used herein means both a propylene homopolymer and a propylene-α-olefin copolymer.

Examples of the α-olefins other than propylene include the aforementioned α-olefins of 2 to 20 carbon atoms, other than propylene. Of these, ethylene, 1-butene, 1-hexene and 1-octene are preferably used.

Together with propylene and the α-olefin other than propylene, the same polyenes as described above are copolymerizable.

The polymerization conditions for preparing the propylene polymer are the same as those described above.

The first propylene polymer obtained by the above process has a propylene/α-olefin ratio of usually 55/45 to 100/2, preferably 60/40 to 100/5.

The first propylene polymer has MFR of usually 0.01 to 200 g/10 min, preferably 0.03 to 100 g/10 min, an intrinsic viscosity [η] of usually 0.5 to 6.0 dl/g, preferably 1.0 to 4.0 dl/g, and a density of usually 0.85 to 0.95 g/cm$^3$, preferably 0.86 to 0.94 g/cm$^3$.

Of the propylene polymers, the propylene homopolymer has a mr/(mm+rr) value, in the dyad distribution measured by $^{13}$C-NMR, of 0.7 to 1.3, preferably 0.8 to 1.2.

The values for mr, mm and rr in the dyad distribution measured by $^{13}$C-NMR were determined in the following manner. In an NMR sample tube (diameter: 5 mm), a sample of 50 to 70 mg is completely dissolved in a solvent containing about 0.5 ml of hexachlorobutadiene, o-dichlorobenzene or 1,2,4-trichlorbenzene and about 0.05 ml of deuterated benzene as a lock solvent, and the $^{13}$C-NMR spectrum is measured by proton complete decoupling at 120° C. under the measuring conditions of a flip angle of 45° and a pulse interval of not shorter than 3.4 $T_1$ ($T_1$: longest time among the spin-lattice relaxation time of methyl groups). Since $T_1$ of the methylene group and $T_1$ of the methine group are shorter than that of the methyl group, the magnetization recovery under the above conditions is not less than 99%, As for the chemical shift, the methyl group of the third unit in the head-to-tail enchained propylene unit pentad sequence having the same methyl branch directions is preset to 21.59 ppm.

In the spectrum relating to the methyl carbon region (19 to 23 ppm), the peak region is classified into the first region (21.1 to 21.9 ppm), the second region (20.3 to 21.0 ppm) and the third region (19.5 to 20.3 ppm) Each peak in the spectrum is assigned by reference to "Polymer, 30(1989) 1350".

The mr, mm and rr represent the following head-to-tail enchained propylene unit triad sequences, respectively.

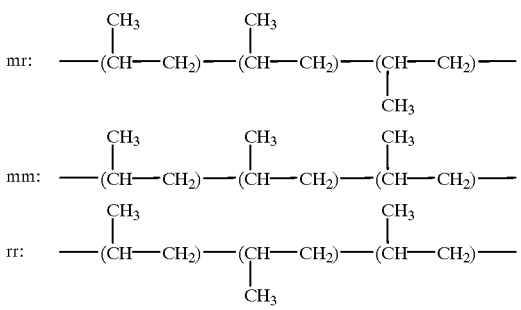

The propylene polymer obtained by the above process is characterized by having a narrow molecular weight distribution and a narrow composition distribution.

Next, the second process for preparing an olefin polymer according to the invention and the olefin polymer obtained by the process are described below.

The second process for preparing an olefin polymer according to the invention comprises homopolymerizing an olefin or copolymerizing two or more kinds of olefins in the presence of a catalyst which comprises:

(A-2) a Group IVB transition metal compound represented by the following formula (II), (B) (B-1) an organoaluminum oxy-compound, and/or
(B-2) a compound which reacts with the transition metal compound (A-2) to form an ion pair, and optionally (C) an organoaluminum compound.

First, the olefin polymerization catalyst used in the invention is described below.

The transition metal compound (A-2) used in the invention is a transition metal compound represented by the formula (II).

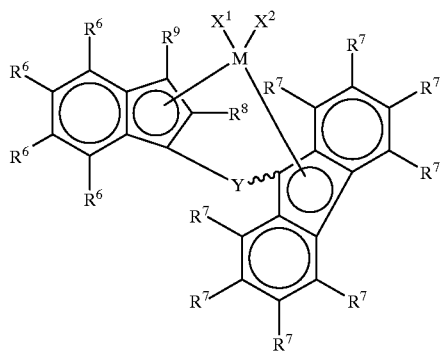

In the formula (II), M is a transition metal atom of Group IVB of the periodic table, specifically titanium, zirconium or hafnium, preferably zirconium.

$R^6$'s may be the same as or different from each other, and are each hydrogen atom, a halogen atom, an alkyl group of 1 to 10 carbon atoms, an aryl group of 6 to 10 carbon atoms, an alkenyl group of 2 to 10 carbon atoms, a silicon-containing group, an oxygen-containing group, a sulfur-containing group, a nitrogen-containing group or a phosphorus-containing group.

Examples of the halogen atoms and the alkyl groups of 1 to 10 carbon atoms are the same as those for $R^1$ in the formula (I). Examples of the silicon-containing groups, the oxygen-containing group, the sulfur-containing groups, the nitrogen-containing groups and the phosphorus-containing groups are the same as those for $R^2$ in the formula (I).

Examples of the aryl groups of 6 to 10 carbon atoms include phenyl and α- or β-naphthyl.

Examples of the alkenyl groups of 2 to 10 carbon atoms include vinyl, propenyl and cyclohexenyl.

The alkyl groups and the alkenyl groups may be substituted with halogens.

Of these, $R^6$ is preferably an alkyl group, an aryl group or hydrogen, particularly preferably a hydrocarbon group of 1 to 3 carbon atoms, i.e., methyl, ethyl, n-propyl or i-propyl, an aryl group such as phenyl, α-naphthyl or β-naphthyl, or hydrogen atom.

$R^7$'s may be the same as or different from each other, and are each hydrogen atom, a halogen atom, an alkyl group of 1 to 10 carbon atoms, an aryl group of 6 to 20 carbon atoms, an alkenyl group of 2 to 10 carbon atoms, an arylalkyl group of 7 to 40 carbon atoms, an arylalkenyl group of 8 to 40 carbon atoms, an alkylaryl group of 7 to 40 carbon atoms, a silicon-containing group, an oxygen-containing group, a sulfur-containing group, a nitrogen-containing group or a phosphorus-containing group. Examples of such atoms and groups awe the same as those for $R^2$ in the formula (I)

These alkyl groups, aryl groups, alkenyl groups, arylalkyl groups, arylalkenyl groups and alkylaryl groups may be substituted with halogens, Of these, $R^7$ is preferably hydrogen atom or an alkyl group, particularly preferably hydrogen or a hydrocarbon group of 1 to 4 carbon atoms, i.e., methyl, ethyl, n-propyl, i-propyl, n-butyl or tert-butyl.

$R^6$ and $R^7$ may be the same as or different from each other.

Any one of $R^8$ and $R^9$ is an alkyl group of 1 to 5 carbon atoms, and the other is hydrogen, a halogen atom, an alkyl group of 1 to 10 carbon atoms, an alkenyl group of 2 to 10 carbon atoms, a silicon-containing group, an oxygen-containing group, a sulfur-containing group, a nitrogen-containing group or a phosphorus-containing group, examples of which are the same as those for $R^2$ in the formula (I)

Examples of the alkyl groups of 1 to 5 carbon atoms include methyl, ethyl, propyl, butyl and pentyl.

It is preferred that any one of $R^8$ and $R^9$ is an alkyl group of 1 to 3 carbon atoms such as methyl, ethyl or propyl and the other is hydrogen atom.

$X^1$ and $X^2$ may be the same as or different from each other, and are each hydrogen atom, a halogen atom, a hydrocarbon group of 1 to 20 carbon atoms, a halogenated hydrocarbon group of 1 to 20 carbon atoms, an oxygen-containing group or a sulfur-containing group. Examples of such atoms and groups are the same as those for $X^1$ and $X^2$ in the formula (I).

Of these, the halogen atom or the hydrocarbon group of 1 to 20 carbon atoms is preferable.

Y is a divalent hydrocarbon group of 1 to 20 carbon atoms, a divalent halogenated hydrocarbon group of 1 to 20 carbon atoms, a divalent silicon-containing group, a divalent germanium-containing group, a divalent tin-containing group, —O—, —CO—, —S—, —SO—, —SO$_2$—, —NR$^5$—, —P(R$^5$)—, —P(O)(R$^5$)—, —BR$^5$— or —AlR$^5$—($R^5$ is hydrogen atom, a halogen atom, a hydrocarbon group of 1 to 20 carbon atoms or a halogenated hydrocarbon group of 1 to 20 carbon atoms). Examples of such groups are the same as those for Y in the formula (I).

Of these, Y is preferably a divalent hydrocarbon group of 1 to 5 carbon atoms, a divalent silicon-containing group or a divalent germanium-containing group, more preferably a divalent silicon-containing group, particularly preferably alkylsilylene, alkylarylsilylene or arylsilylene.

Listed below are examples of the transition metal compounds represented by the formula (II)

Ethylene(2-methyl-1-indenyl)(9-fluorenyl)zirconium dichloride,

Dimethylsilylene(2-methyl-1-indenyl)(9-fluorenyl)zirconium dichloride,

Diphenylsilylene(2-methyl-1-indenyl)(9-fluorenyl)zirconium dichloride,

Methylphenylsilylene(2-methyl-1-indenyl)(9-fluorenyl)zirconium dichloride,

Ethylene(3-methyl-1-indenyl)(9-fluorenyl)zirconium dichloride,

Dimethylsilylene(3-methyl-1-indenyl)(9-fluorenyl)zirconium dichloride,

Diphenylsilylene(3-methyl-1-indenyl)(9-fluorenyl)zirconium dichloride,

Methylphenylsilylene(3-methyl-1-indenyl)(9-fluorenyl)zirconium dichloride,

Ethylene(2-methyl-1-indenyl)(2,7-di-tert-butyl-9-fluorenyl)zirconium dichloride, Dimethylsilylene(2-methyl-1-indenyl)(2,7-di-tert-butyl-9-fluorenyl)zirconium dichloride, Diphenylsilylene(2-methyl-1-indenyl)(2,7-di-tert-butyl-9-fluorenyl)zirconium dichloride, Methylphenylsilylene(2-methyl-1-indenyl)(2,7-di-tert-butyl-9-fluorenyl)zirconium dichloride, Ethylene(2-methyl-4-phenyl-1-indenyl)(9-fluorenyl)zirconium dichloride, Dimethylsilylene(2-methyl-4-phenyl-1-indenyl)(9-fluorenyl)zirconium dichloride, Diphenylsilylene(2-methyl-4-phenyl-1-indenyl)(9-fluorenyl)zirconium dichloride, Methylphenylsilylene(2-methyl-4-phenyl-1-indenyl)(9-fluorenyl)zirconium dichloride, Ethylene(2-methyl-4-phenyl-1-indenyl)(2,7-di-tert-butyl-9-fluorenyl)zirconium dichloride, Dimethylsilylene(2-methyl-4-phenyl-1-indenyl)(2,7-di-tert-butyl-9-fluorenyl)zirconium dichloride, Diphenylsilylene(2-methyl-4-phenyl-1-indenyl)(2,7-di-tert-butyl-9-fluorenyl)zirconium dichloride, Methylphenylsilylene(2-methyl-4-phenyl-1-indenyl)(2,7-di-tert-butyl-9-fluorenyl)zirconium dichloride, Ethylene(2-methyl-4-naphthyl-1-indenyl)(9-fluorenyl)zirconium dichloride, Dimethylsilylene(2-methyl-4-naphthyl-1-indenyl)(9-fluorenyl)zirconium dichloride, Diphenylsilylene(2-methyl-4-naphthyl-1-indenyl)(9-fluorenyl)zirconium dichloride, Methylphenylsilylene(2-methyl-4-naphthyl-1-indenyl)(9-fluorenyl)zirconium dichloride, Ethylene(2-methyl-4-naphthyl-1-indenyl)(2,7-di-tert-butyl-9-fluorenyl)zirconium dichloride, Dimethylsilylene(2-methyl-4-naphthyl-1-indenyl)(2,7-di-tert-butyl-9-fluorenyl)zirconium dichloride, Diphenylsilylene(2-methyl-4-naphthyl-1-indenyl)(2,7-di-tert-butyl-9-fluorenyl)zirconium dichloride, and Methylphenylsilylene(2-methyl-4-naphthyl-1-indenyl)(2,7-di-tert-butyl-9-fluorenyl)zirconium dichloride.

Also employable are compounds wherein zirconium is replaced with titanium or hafnium in the above-exemplified zirconium compounds.

The transition metal compounds (A-2) mentioned above may be used in combination of two or more kinds.

Examples of the organoaluminum oxy-compound (B-1) used in the invention are the same as those of the aforesaid organoaluminum oxy-compound. Examples of the compound (B-2) which reacts with the transition metal compound (A-2) to form an ion pair are the same as those of the aforesaid compound which reacts with the transition metal compound (A-1) to form an ion pair.

Examples of the organoaluminum compound (C) optionally used in the invention are the same as those of the aforesaid organoaluminum compound.

The olefin polymerization catalyst used in the second process for preparing an olefin polymer according to the invention may be a solid catalyst wherein at least one of the component (A-2), the component (B-1), the component (B-2) and the component (C) is supported on a fine particle carrier.

The olefin polymerization catalyst may be a prepolymerized catalyst comprising a fine particle carrier, the component (A-2), the component (3-l) (or the component (B-2)), an olefin polymer produced by prepolymerization, and optionally, the component (C).

Examples of the fine particle carrier used in the solid catalyst or the prepolymerized catalyst are the same as those of the aforesaid fine particle carrier.

In FIG. 2, steps for preparing the olefin polymerization catalyst used in the second process for preparing an olefin polymer according to the invention are shown.

In the second process for preparing an olefin polymer according co the invention, an olefin is homopolymerized or two or more kinds of olefins are copolymerized in the presence of the olefin polymerization catalyst comprising the transition metal compound (A-2), the organoaluminum oxy-compound and/or the ionized ionic compound (B), and optionally, the organoaluminum compound (C)

Examples of the olefins used in the invention include the same chain or branched olefins and olefins having an aliphatic ring or an aromatic ring as used in the first process for preparing an olefin polymer.

Together with the olefins, the same polyenes as used in the first process for preparing an olefin polymer are copolymerizable.

In the (co)polymerization of the olefin, the transition metal compound (A-2) is used in an amount of usually about 0.00005 to 0.1 mmol, preferably about 0.0001 to 0.05 mmol, in terms of the transition metal atom, based on 1 liter of the polymerization volume.

The organoaluminum oxy-compound (B-1) is used in such an amount that the amount of the aluminum atom becomes usually about 1 to 10,000 mol, preferably 10 to 5,000 mol, based on 1 mol of the transition metal atom.

The ionized ionic compound (B-2) is used in such an amount that the amount of the boron atom becomes usually about 0.5 to 20 mol, preferably 1 to 10 mol, based on 1 mol of the transition metal atom.

The organoaluminum compound (C) is used if necessary, in an amount of usually about 0 to 200 mol. preferably about 0 to 100 mol, baser on 1 mol of the aluminum atom in the organoaluminum oxy-compound (B-1). The compound (C) is used, if necessary, in an amount of usually about 0 to 1,000 mol, preferably about 0 to 500 mol, based on 1 mol of the boron atom in the ionized ionic compound (B-2).

The (co)polymerization of the olefin can be carried out any of a liquid phase polymerization process such as suspension polymerization process or solution polymerization process, a gas phase polymerization process and a high-pressure process.

In the liquid phase polymerization process, the same inert hydrocarbon media as used in the first process for preparing an olefin polymer are employable. The olefin itself can be used as a solvent. These solvents may be used in combination of two or more kinds.

In the suspension polymerization process, the polymerization temperature is in the range of usually −50 to 100° C., preferably 0 to 90° C.; in the solution polymerization process, the polymerization temperature is in the range of usually 0 to 250° C., preferably 20 to 200° C.; and in the gas phase polymerization process, the polymerization temperature is in the range of usually 0 to 120° C., preferably 20 to 100° C. In the high-pressure process, the polymerization temperature is in the range of usually 50 to 1,000° C., preferably 100 to 500° C. The polymerization pressure is in the range of usually atmospheric pressure to 100 kg/cm$^2$, preferably atmospheric pressure to 50 kg/cm$^2$. In the high-pressure process, the polymerization pressure is in the range of usually 100 to 10,000 kg/cm$^2$, preferably 500 to 5,000 kg/cm$^2$. The polymerization reaction can be carried out by any of batchwise, semi-continuous and continuous processes. The copolymerization can be conducted in two or more stages under different reaction conditions.

The molecular weight of the resulting olefin polymer can be modified by allowing hydrogen to exist in the polymerization system or varying the polymerization temperature or the polymerization pressure.

In the present invention, the transition metal compound (A-2) which contains, as a ligand, an indenyl group having a specific substituent at the specific position is used as a transition metal catalyst component, and therefore there can be obtained an olefin (co)polymer of higher molecular weight and an olefin copolymer of higher comonomer content as compared with the case of using an olefin polymerization catalyst which uses as its catalyst component a transition metal compound not having such substituent.

The second olefin polymer of the invention obtained by the above process has MFR of usually 0.01 to 200 g/10 min, preferably 0.03 to 100 g/10 min, an intrinsic viscosity [η] of usually 0.5 to 6.0 dl/g, preferably 1.0 to 4.0 dl/g, and a density of usually 0.85 to 0.95 g/cm$^3$, preferably 0.86 to 0.94 g/cm$^3$.

The olefin polymer obtained by the above process is characterized by having a narrow molecular weight distribution and a narrow composition distribution.

The second process for preparing an olefin polymer according to the invention is favorably used for preparing particularly an ethylene polymer and a propylene polymer.

For preparing the ethylene polymer, ethylene is homopolymerized or ethylene and an α-olefin of 3 to 20 carbon atoms are copolymerized in the presence of the aforesaid olefin polymerization catalyst.

Examples of the α-olefins of 3 to 20 carbon atoms include the aforementioned α-olefins of 2 to 20 carbon atoms, other than ethylene. Of these, propylene, 1-butene, 1-hexene and 1-octene are preferably employed.

Together with ethylene and the α-olefin of 3 to 20 carbon atoms, the same polyenes as described above are copolymerizable.

The polymerization conditions for preparing the ethylene polymer are the same as those described above.

The second ethylene polymer obtained by the above process has an ethylene/α-olefin ratio of usually 55/45 to 100/2, preferably 60/40 to 100/5.

The second ethylene polymer has MFR of usually 0.01 to 200 g/10 min, preferably 0.03 to 100 g/10 min, an intrinsic viscosity [η] of usually 0.5 to 5.0 dl/g, preferably 1.0 to 4.0 dl/g, and a density of usually 0.85 to 0.95 g/cm$^3$, preferably 0.86 to 0.94 g/cm$^3$.

For preparing the propylene polymer, propylene is homopolymerized or propylene and an α-olefin other than propylene are copolymerized in the presence of tile aforesaid olefin polymerization catalyst.

Examples of the α-olefins other than propylene include the aforementioned α-olefins of 2 to 20 carbon atoms, other than propylene. Of these, ethylene, 1-butene, 1-hexene and 1-octene are preferably employed.

Together with propylene and the α-olefin other than propylene, the same polyenes as described above are copolymerizable.

The polymerization conditions for preparing the propylene polymer are the same as those described above.

The second propylene polymer obtained by the above process has a propylene/α-olefin ratio of usually 55/45 to 100/2, preferably 60/40 to 100/5.

The second propylene polymer has MFR of usually 0.01 to 200 g/10 min, preferably 0.03 to 100 g/10 min an intrinsic viscosity [η] of usually 0.5 to 6.0 dl/g, preferably 1.0 to 4.0 dl/g, and a density of usually 0.85 to 0.95 g/cm$^3$, preferably 0.86 to 0.94 g/cm$^3$.

Of the propylene polymers, the propylene homopolymer has a mr/(mm+rr) value, in the dyad distribution measured by $^{13}$C-NMR, of 0.7 to 1.3, preferably 0.8 to 1.2.

The propylene polymer obtained by the above process is characterized by having a narrow molecular weight distribution and a narrow composition distribution.

EFFECT OF THE INVENTION

The olefin polymerization catalyst of the invention uses a specific transition metal compound as an olefin polymerization catalyst component, and therefore an olefin (co)polymer having a high molecular weight can be obtained. Besides, an olefin polymer having a high comonomer content can be obtained even if a comonomer is used in a small proportion. In the polymerization using a polyene together with the olefin, an olefin polymer having a high polyene content can be obtained even if the polyene is used in a small proportion.

In the first process for preparing an olefin polymer according to the invention, a specific transition metal compound is used as an olefin polymerization catalyst component, and therefore an olefin (co)polymer having a high molecular weight can be obtained Besides, an olefin polymer having a high comonomer content can be obtained even if a comonomer is used in a small proportion. In the polymerization using a polyene together with the olefin, an olefin polymer having a high polyene content can be obtained even if the polyene is used in a small proportion.

The first olefin polymer of the invention has a narrow molecular weight distribution. When the olefin polymer is a copolymer, it has a narrow molecular weight distribution and a narrow composition distribution.

In the second process for preparing an olefin polymer according to the invention, a specific transition metal compound is used as an olefin polymerization catalyst component, and therefore an olefin (co)polymer having a high molecular weight can be obtained. Besides, an olefin polymer having a high comonomer content can be obtained even if a comonomer is used in a small proportion. In the polymerization using a polyene together with the olefin, an olefin polymer having a high polyene content can be obtained even if the polyene is used in a small proportion.

The second olefin polymer has a narrow molecular weight distribution. When the olefin polymer is a copolymer, it has a narrow molecular weight distribution and a narrow composition distribution.

EXAMPLE

The present invention will be further described with reference to the following examples, but it should be construed that the invention is in no way limited to those examples.

Preparation Example 1

Synthesis of dimethylsilylene(2-methyl-4,5-benzo-1-indenyl)(2,7-di-t-butyl-9-fluorenyl)zirconium dichloride To a 100 ml reactor, 50 ml of diethyl ether and 5.57 g (20 mmol) of 2,7-di-t-butyl-9-fluorene were introduced. Under ice-cooling, to the reactor was dropwise added 12.0 ml of a hexane solution of n-butyllithium (1.67 mmol/ml) over a period of 10 minutes, followed by stirring at room temperature for 10 hours, to obtain a mixture A.

To a 200 ml reactor, 40 ml of diethyl ether and 41.2 g (320 mmol) of dimethyldichlorosilane were introduced. Under ice-cooling, to he reactor was dropwise added the above-obtained mixture A over a period of 1 hour, followed by stirring at room temperature for 1 hour. After diethyl ether and dimethyldichlorosilane were distilled off under reduced pressure, 100 ml of methylene chloride was added and stirred. Then, a solid produced was removed by means of a glass filter. From the resulting methylene chloride solution, methylene chloride was distilled off under reduced pressure. Then, the pressure of the system was reduced by means of a vacuum pump to further distill off the solvent, whereby an orange viscous oil was obtained.

To a 100 ml reactor, 50 ml of diethyl ether and 3.60 g (20 mmol) of 2-methyl-4,5-benzoindene were introduced Under ice-cooling, to the reactor was dropwise added 12.0 ml of a hexane solution of n-butyllithium (1.67 mmol/ml) over a period of 10 minutes, followed by stirring at room temperature for 13 hours, to obtain a mixture B.

To a 200 ml reactor, 40 ml of a diethyl ether solution of the orange viscous oil obtained by the above reaction was introduced. Under ice-cooling, to the reactor was dropwise added the above-obtained mixture B over a period of 30 minutes, followed by stirring at room temperature for 1 day. The reaction liquid was poured into a saturated ammonium chloride aqueous solution. Then, the ether layer is washed with water and dried over anhydrous magnesium sulfate. After the ether layer was concentrated, it was separated and purified by silica gel column chromatography (developer: n-hexane) to obtain 4.0 g (yield: 40%) of an aimed product [dimethylsilylene(2-methyl-4,5benzo-1-indenyl)(2,7-di-t-butyl-9-fluorene)] as a light yellow amorphous solid.

Data of the N spectrum of the compound obtained are described below, $^1$H-NMR ($\delta$ value, CDCl$_3$, 90 MHz); −0.4 (s, 3H); −0.3 (d, J=3.6 Hz, 3H); 1.23–1.60 (m, 18 H); 2.29–2.40 (br. s, 3H); 3.80–3.94 (m, 1H); 4.17–4.31 (m, 1H); 7.29–8.34 (m, 13H).

To a 100 ml reactor, 50 ml of diethyl ether and 1.50 g (3.2 mmol) of the above-obtained dimethylsilylene(2-methyl-4,5-benzo-1-indenyl)(2,7-d-t-butyl-9-fluorene) were introduced. Under ice-cooling, to the reactor was added 3.8 ml of a hexane solution of n-butyllithium (1.67 mmol/ml) over a period of 10 minutes, and the reaction was continued at room temperature for 1 hour and then for another 30 minutes under reflux. The resulting dark yellow slurry was cooled to −60° C., and thereto was little by little added 0.75 g (3.2 mmol) cc zirconium tetrachloride. The temperature of the system was allowed to spontaneously rise to room temperature, and the reaction mixture was stirred at room temperature for 12 hours.

A solid produced was filtered through a glass filter. To the resulting solid was added 10 ml of diethyl ether to wash the solid, followed by filtration under reduced pressure. A solid produced was washed with 40 ml of methylene chloride and filtered through a glass filter. The methylene chloride solution was concentrated to precipitate a solid, and the solid was separated by means of a glass filter to obtain 0.84 g of an aimed product [dimethylsilylene(2-methyl-4,5-benzo-1-indenyl)(2,7-di-t-butyl-9-fluorenyl)zirconium dichloride] as an orange powder.

Data of the NMR spectrum of the compound obtained are described below.

$^1$H-NMR ($\delta$ value, CDCl$_3$, 90 MHz); 1.25 (s, 9H); 1.35 (s, 9H); 1.44 (s, 3h); 1.54 (s, 3H); 2.37 (s, 3H); 7.0–8.02 (m, 13H).

Preparation Example 2

Synthesis of dimethylsilylene(2-methyl-4,5-benzo-1-indenyl)(9-fluorenyl)zirconium dichloride To a 100 ml reactor, 50 ml of diethyl ether and 3.32 g (20 mmol) of fluorene were introduced. Under ice-cooling, to the reactor was dropwise added 12.0 ml of a hexane solution of n-butyllithium (1.67 mmol/ml) over a period of 10 minutes, followed by stirring at room temperature for 10 hours, to obtain a mixture A.

To a 200 ml reactor, 40 ml of diethyl ether and 41.2 g (320 mmol) of dimethyldichlorosilane were introduced. Under ice-cooling, to the reactor was dropwise added the above-obtained mixture A over a period of 1 hour, followed by stirring at room temperature for 1 hour. After diethyl ether and dimethyldichlorosilane were distilled off under reduced pressure, 100 ml of methylene chloride was added and stirred. Then, a solid produced was removed by means of a glass filter. From tie resulting methylene chloride solution, methylene chloride was distilled off under reduced pressure.

Then, the pressure of the system was reduced by means of a vacuum pump to further distill off the solvent, whereby an orange viscous oil was obtained.

To a 100 ml reactor, 50 ml of diethyl ether and 3.89 g (20 mmol) of 2-methyl-4,5-benzoindene were introduced. Under ice-cooling, to the reactor was dropwise added 12.0 ml of a hexane solution of n-butyllithium (1.67 mmol/ml) over a period of 10 minutes, followed by stirring at room temperature for 13 hours, to obtain a mixture B.

To a 200 ml reactor, 40 ml of a diethyl ether solution of the orange viscous oil obtained by the above reaction was introduced. Under ice-cooling, to the reactor was dropwise added the above-obtained mixture B over a period of 30 minutes, followed by stirring at room temperature for 1 day. The resulting reaction liquid was poured into a saturated ammonium chloride aqueous solution. Then, the ether phase is washed with water and dried over anhydrous magnesium sulfate. After the ether phase was concentrated, it was separated and purified by silica gel column chromatography (developer: n-hexane) to obtain 3.88 g (yield: 48%) of an aimed product [dimethylsilylene(2-methyl-4,5-benzo-1-indenyl)(9-fluorene)] as a light yellow amorphous solid.

Data of the M spectrum of the compound obtained are described below.

$^1$H-NMR ($\delta$ value, CDCl$_3$, 90 MHz); −0.4 (s, 3H); −0.3 (d, J=3.6 Hz, 3H); 2.29–2.40 (br. s, 3H); 3.94 (br. S, 1H); 4.26 (br. S, 1H); 7.09–8.31 (m, 15H);

To a 100 ml reactor, 50 ml of diethyl ether and 1.30 g (3.2 mmol) of the above-obtained cimetliylsilylene(2-methyl-4,5-benzo-1-indenyl)(9-fluorene) were introduced. Under ice-cooling, to the reactor was added 3.8 ml of a hexane solution of n-butyllithium (1.67 mmol/ml) over a period of 10 minutes, and the reaction was continued at room temperature for 1 hour and then for another 30 minutes under reflux. The resulting dark yellow slurry was cooled to −60° C., and thereto was little by little added 0.75 g (3.2 mmol) of zirconium tetrachloride. The temperature of the system was allowed to spontaneously rise to room temperature, and the reaction mixture was stirred at room temperature for 12 hours, A solid produced was filtered by means of a glass filter. To the resulting solid was added 10 ml of diethyl ether to wash the solid, followed by filtration under reduced pressure. A solid produced was washed with 40 ml of methylene chloride and filtered by means of a glass filter. The methylene chloride solution was concentrated to precipitate a solid, and the solid was separated by means of a glass filter to obtain 0.96 g of an aimed product [dimethylsilylene(2-methyl-4,5-benzo-1-indenyl)(9-fluorenyl)zirconium dichloride] as an orange powder.

Data of the NMR spectrum of the compound obtained are described below.

$^1$H-NMR ($\delta$ value, CDCl$_3$, 90 MHz); 1.44 (s, 3H); 1.54 (s, 3H); 2.37 (s, 3H); 6.99–8.00 (m, 15H).

Preparation Example 3

Synthesis of dimethylsilylene(2,6-dimethyl-4,5-benzo-1-indenyl)(2,7-di-t-butyl-9-fluorenyl) zirconium dichloride To a 100 ml reactor, 50 ml of diethyl ether and 5.57 g (20 mrol) of 2,7-di-t-butyl-9-fluorene were introduced. Under ice-cooling, to the reactor was dropwise added 12.0 ml of a hexane solution of n-butyllithium (1.67 mmol/ml) over a period of 10 minutes, followed by stirring at room temperature for 10 hours, to obtain a mixture A.

To a 200 ml reactor, 40 ml of diethyl ether and 41.2 g (320 mmol) of0 dimethyldichlorosilane were introduced. Under ice-cooling, to the reactor was dropwise added the above-obtained mixture A over a period of 1 hour, followed by stirring at room temperature for 1 hour. After diethyl ether and dimethyldichlorosilane were distilled off under reduced pressure, 100 ml of methylene chloride was added and stirred. Then, a solid produced was removed by means of a glass filter. From the resulting methylene chloride solution, methylene chloride was distilled off under reduced pressure. Then, the pressure of the system was reduced by means of a vacuum pump to further distill off the solvent, whereby an orange viscous oil was obtained.

To a 100 ml reactor, 50 ml of diethyl ether and 3.88 g (20 mmol) of 2,6-dimethyl-4,5-benzoindene were introduced. Under ice-cooling, to the reactor was dropwise added 12.0 ml of a hexane solution of n-butyllithium (1.67 mmol/ml) over a period of 10 minutes, followed by stirring at room temperature for 13 hours, to obtain a mixture B.

To a 200 ml reactor, 40 ml of a diethyl ether solution of the orange viscous oil obtained by the above reaction was introduced. Under ice-cooling, to the reactor was dropwise added the above-obtained mixture B over a period of 30 minutes, followed by stirring at room temperature for 1 day. The resulting reaction liquid was poured into a saturated ammonium chloride aqueous solution. Then, the ether phase is washed with water and dried over anhydrous magnesium sulfate. After the ether phase was concentrated, it was separated and purified by silica gel column chromatography (developer: n-hexane) to obtain 4.8 g (yield: 45%) of an aimed product [dimethylsilylene(2,6-dimethyl-4,5-benzo-1-indenyl)(2,7-di-t-butyl-9-fluorene)] as a light yellow amorphous solid.

To a 100 ml reactor, 50 ml of diethyl ether and 1.69 g (3.2 mmol) of the above-obtained dimethylsilylene( 2,6-dimethyl-4,5-benzo-1-indenyl)(2,7-di-t-butyl-9-fluorene) were introduced. Under ice-cooling, to the reactor was added 3.8 ml of a hexane solution of n-butyllithium (1.67 mmol/ml) over a period of 10 minutes, and the reaction was continued at room temperature for 1 hour and then for another 30 minutes under reflux. The resulting dark yellow slurry was cooled to −60° C., and thereto was little by little added 0.75 g (3.2 mmol) of zirconium tetrachloride. The temperature of the system was allowed to spontaneously rise to room temperature, and the reaction mixture was stirred at room temperature for 12 hours.

A solid produced was filtered by means of a glass filter. To the resulting solid was added 10 ml of diethyl ether to wash the solid, followed by filtration under reduced pressure. A solid produced was washed with 40 ml of methylene chloride and filtered by means of a glass filter. The methylene chloride solution was concentrated to precipitate a solid, and the solid was separated by means of a glass filter to obtain 1.02 g of an aimed product [dimethylsilylene(2,6-diethyl-4,5-benzo-1-indenyl)(2,7-di-t-butyl-9-fluorenyl)zirconium dichloride] as an orange powder, Data of the NMR spectrum of the compound obtained are described below.

$^1$H-NMR ($\delta$ value, CDCl$_3$, 90 MHz); 1.24 (s, 9H); 1.35 (s, 9H); 1.43 (s, 3H); 1.56 (s, 3H); 2.36 (s, 3H); 2.50 (s, 3H); 7.01–8.02 (m, 12H);

Preparation Example 4

Synthesis of dimethylsilylene(2,7-dimethyl-4,5-(2-metyl-benzo)-1-indenyl)(2,7-di-t-butyl-9-fluorenyl) zirconium dichloride To a 100 ml reactor, 50 ml of diethyl ether and 5,57 g (20 mmoxl) of 2,7-di-t-butyl-9-fluorene were introduced. Under ice-cooling, to the reactor was dropwise added 12.0 ml of a hexane solution of n-butyllithium (1.67 mmol/ml) over a period of 10 minutes, followed by stirring at room temperature for 10 hours, to obtain a mixture A.

To a 200 ml reactor, 40 ml of diethyl ether and 41.2 g (320 mmol) of dimethyldichlorosilane were introduced. Under ice-cooling, to the reactor was dropwise added the above-obtained mixture A over a period of 1 hour, followed by stirring at room temperature for 1 hour. After diethyl ether and dimethyldichlorosilane were distilled off under reduced pressure, 100 ml of methylene chloride was added and stirred. Token, a solid produced was removed by means of a glass filter. From the resulting methylene chloride solution, methylene chloride was distilled off under reduced pressure. Then, the pressure of the system was reduced by means of a vacuum pump to further distill off the solvent, whereby an orange viscous oil was obtained.

To a 100 ml reactor, 50 ml of diethyl ether and 4.16 g (20 mmol) of 2,7-dimethyl-4,5-(2-methyl-benzo)indene were introduced. Under ice-cooling, to the reactor was dropwise added 12.0 ml of a hexane solution of n-butyllithium (1.67 mmol/ml) over a period of 10 minutes, followed by stirring at room temperature for 13 hours, to obtain a mixture B.

To a 200 ml reactor, 40 ml of a diethyl ether solution of the orange viscous oil obtained by the above reaction was introduced. Under ice-cooling, to the reactor was dropwise added the above-obtained mixture 3 over a period of 30 minutes, followed by stirring at room temperature for 1 day. The reaction liquid was poured into a saturated ammonium chloride aqueous solutions Then, the ether phase is washed with water and dried over anhydrous magnesium sulfate. After the ether phase was concentrated, it was separated and purified by silica gel column chromatography (developer: n-hexane) to obtain 5.2 g (yield: 48%) of an aimed product [dimethylsilylene(2,7-dimethyl-4,5-(2-methyl-benzo)-1-indenyl)(2,7-di-t-butyl-9-fluorene)] as a light yellow amorphous solid.

To a 100 ml reactor, 50 ml of diethyl ether and 1.73 g (3.2 mmol) of the above-obtained dimethylsilylene(2,6-dimethyl-4,5-(2-methyl-benzo)1-indenyl)(2,7-di-t-butyl-9-fluorene) were introduced. Under ice-cooling, to the reactor was added 3.8 ml of a hexane solution of n-butyllithium (1.67 mmol/ml) over a period of 10 minutes, and the reaction was continued at room temperature for 1 hour and then for another 30 minutes under reflux. The resulting dark yellow slurry was cooled to −60° C., and thereto was little by little added 0.75 g (3.2 mmol) of zirconium tetrachloride. The temperature of the system was allowed to spontaneously rise to room temperature, and the reaction mixture was stirred at room temperature for 12 hours.

A solid produced was filtered by means of a glass filter. To the resulting solid was added 10 ml of diethyl ether to wash the solid, followed by filtration under reduced pressure. A solid produced was washed with 40 ml of methylene chloride and filtered by means of a glass filter. The methylene chloride solution was concentrated to precipitate a solid, and the solid was separated by means of a glass filter to obtain 0.94 g of an aimed product [dimethylsilylene(2,7-dimethyl-4,5-(2-methyl-benzo)-1-indenyl)(2,7-di-t-butyl-9-fluorenyl) zirconium dichloride] as an orange powder.

Data of the NMR spectrum of the compound obtained are described below.

$^1$H-NMR (δ value, CDCl$_3$, 90 MHz); 0.69 (s, 9H); 1.36 (s, 9H); 1.56 (s, 3H); 1.69 (s, 3H); 2.24 (s, 3H); 2.47 (s, 3H); 2.57 (s, 3H); 6.71–8.40 (m, 11H).

Preparation Example 5

Synthesis of dimethylsilylene(2-n-propyl-4-(9-phenanthryl)-1-indenyl)(9-fluorenyl)zirconium dichloride Synthesis of dimethyl(9-fluorenyl)silane chloride A 1 liter four-necked flask equipped with a reflux tube, a thermometer and a dropping funnel was thoroughly purged with nitrogen and dried. To the flask, fluorene (5.00 g, 30 mmol) and dehydrated ether (100 ml) were introduced. Under stirring at −10° C., a hexane solution of n-butyllithium (30 Tmol) was dropwise added over a period of 30 minutes. After the dropwise addition, the temperature of the system was allowed to spontaneously rise to room temperature little by little, and the reaction mixture was stirred at room temperature for 4 hours. The reaction solution turned into a yellow slurry. The slurry was dropwise added to a solution of dichlorodimethylsilane (18.24 ml, 150 mmol)/dehydrated ether (100 ml) over a period of 1 hour under stirring at ~10° C. After the temperature of the system was allowed to spontaneously rise to room temperature, the reaction mixture was stirred over night. Lithium chloride was removed by means of pressure filteration of the resulting solution using a glass filter (G-5). Further the solvent and the unreacted dichlorodimethylsilane remained in the filtrate were removed under reduced pressure. The resulting filtrate was reslurried with dehydrated hexane (100 ml) and subjected to pressure filteration using a glass filter (G-5) to obtain a white powder (3.30 g, yield: 43%).

Data of the spectrum of the obtained product:

$^1$H-NMR (CDCl$_3$); 7.2–8.0 (m, 8H); 4.1 (s, 1H); 0.15 (s, 6H).

Synthesis of dimethyl(2-n-propyl-4-(9-phenanthryl)-1-indenyl)(9-fluorenyl)silane A 200 ml four-necked flask equipped with a reflux tube, a thermometer and a dropping funnel was thoroughly purged with nitrogen and dried. To the flask, 2-n-propyl-4-(9-phenanthryl)-1-indenyl (1.60 g, 4.78 mmol) and dehydrated ether (20 ml) were introduced. Under stirring at −40° C., a hexane solution of n-butyllithium (5.02 mol) was dropwise added. After the dropwise addition, the temperature of the system was allowed to spontaneously rise to room temperature little by little, and the reaction mixture was stirred at room temperature for 7 hours, whereby a white slurry was changed, in turn, to a yellow slurry, a brown slurry and finally a yellow slurry. To the slurry was added dehydrated ether (30 ml), then the dimethyl(9-fluorenyl)silane chloride (1.24 g, 5.02 mmol) synthesized as mentioned above was added under stirring at 0° C., followed by stirring at room temperature overnight. The reaction solution turned into a yellow slurry. To the slurry was added N-methyl-2-pyrrolidone (0.1 g), followed by stirring for another 3 hours, whereby the yellow slurry was changed to an orange solution. After ether (100 ml) and a saturated ammonium chloride aqueous solution (100 ml) were added, the resulting solution was introduced into a separatory funnel to separate out an organic phase, and the organic phase was washed with a saturated ammonium chloride aqueous solution, water and a saturated sodium chloride aqueous solution, in turn, and dried over anhydrous magnesium sulfate. After the solvent was removed, the obtained product (a yellow oil) was purified by column chromatography (solvent: hexane) to obtain a white oil. When the white oil was allowed under reduced pressure by means of a vacuum pump, it was foamed to be set, whereby a white powder (2.02 g, yield: 76%) was obtained.

Data of the spectrum of the obtained product:

$^1$H-NMR (CDCl$_3$, 90 MHZ); 7.0–9.0 (m, 20H); 6.2 (d, 1H); 4.3 (d, 1h); 3.9 (br, 1H); 2.1–2.5 (t, 2H); 1.0–1.6 (br, 2H); 0.6–1.0 (t, 3H); −0.4 to −0.2 (d);

Synthesis of dimethylsilylene(2-n-propyl-4-(9-phenanthryl)-1-indenyl)(9-fluorenyl)zirconium dichloride A 50 ml Schlenk's bottle equipped with a dropping funnel was thoroughly purged with nitrogen and dried. To the bottle, the dimethyl (2-n-propyl-4-(9-phenanthryl)-1-indenyl)(9-fluorenyl)silane (0.80 g, 1.44 mmol) synthesized as mentioned above and dehydrated ether (20 ml) were introduced. Under stirring at –78° C., a hexane solution of n-butyllithium (3.02 mmol) was dropwise added. After the dropwise addition, the temperature of the system was allowed to spontaneously rise to room temperature. After the reaction mixture was stirred at room temperature for 8 hours, whereby the yellow solution was changed to a bright yellow slurry and finally to a brown slurry. To the slurry under stirring again at –78° C., zirconium tetrachloride (0.335 g, 1.44 mmol) was dropwise added. The temperature of the system was allowed co spontaneously rise to room temperature, and the reaction mixture was stirred over night to obtain a red slurry. The ether was removed by means of pressure filtration using a glass filter (G-5), the obtained cake was immediately washed with dehydrated dichloromethane (the cake was lithium chloride). After the solvent in the filtrate thus obtained was removed, the resulting product was reslurried wits dehydrated hexane (25 ml) and filtered by means of a glass filter (G-5) to obtain the aimed product metallocene as a red powder (397 mg, yield: 39%).

Preparation Example 6

Synthesis of ethylene(9-fluorenyl)(2-methyl-1-indenyl)zirconium dichloride

To a 200 ml four-necked flask equipped with a reflux tube, a thermometer and a dropping funnel, 2-methylindene (4.5 g, 34.6 mmol) and dehydrated ether (50 ml) were introduced. To the flask was dropwise added a hexane solution of n-butyllithium (1.61 mol/l, 23.7 ml, 38.1 mmol) at –78° C. over a period of 1 tour. Then, the temperature of the system was allowed to spontaneously rise to room temperature over a period of 6 hours. The reaction mixture became an yellow orange slurry.

Then, to a 500 ml four-necked flask equipped with a reflux tube, a thermometer and a dropping funnel, 1,2-dibromoethane (32.5 g, 0.173 mol) and dehydrated ether (100 ml) were introduced. To the flask was added the whole amount of the reaction mixture obtained above by means of a pipette at 0° C. over a period of 1 hour, followed by stirring at room temperature for 15 hours. The resulting yellow transparent solution was poured into 300 ml of water to separate an ether phase. The aqueous phase was extracted with ether (100 ml×3), and the combined organic phase was dried over anhydrous magnesium sulfate. Then, the solvent was distilled off, and the resulting yellow brown oil was purified by column chromatography (silica gel: 300 g, developer hexane) to obtain 6.25 g (yield: 76%) of an aimed product [3-(2-bromoethyl)-2-methylindene] as an yellow white transparent liquid.

Data of the NMR spectrum of the compound obtained are described below.

$^1$H-NMR (CDCl$_3$, 90 MHz); 1.8–2.6 (m, 2H); 1.93 (s, 3H); 2.8–3.2 (m, 2H); 3.3 (br, 1H); 6.32 (s, 1h); 6.5–7.4 (m, 4H).

To a 300 ml four-necked flask equipped with a reflux tube, a thermometer and a dropping funnel, fluorene (2.11 g, 12.7 mmol) and dehydrated ether (60 ml) were introduced. To the flask was dropwise added a hexane solution of n-butyllithium (1.51 mol/l, 8.7 ml, 14.0 mmol) at 0° C. over a period of 1 hour, and the contents of the flask were refluxed for 2 hours. The reaction mixture became dark red and transparent. Then, the mixture was cooled to –78° C. (to give an yellow slurry), and a solution of 3-(2-bromoethyl)-2-methylindene (3 g, 12.7 mmol) in dehydrated ether (20 ml) was dropwise added over a period of 1 hour. Thereafter, the temperature of the system was allowed to spontaneously rise to room temperature, followed by stirring for 15 hours. The reaction mixture gradually became an yellow slurry.

The reaction mixture was poured into a saturated ammonium chloride aqueous solution (300 ml) to separate an ether phase. The aqueous phase was extracted with ether (100 ml×3), and the combined organic phase was dried over anhydrous magnesium sulfate. Then, the solvent was distilled off, and the resulting white yellow powder was reslurried with hexane (200 ml). The resulting slurry was filtered to obtain 2.50 g (yield: 61%) of an aimed product [1-(9-fluorenyl)-2-(2-methyl-1-indenyl)ethane] as a white powder.

Data of the NMR spectrum of the compound obtained are described below.

$^1$H-NMR (CDCl$_3$, 90 MHz); 1.3–1.9 (m, 4H); 1.92 (s, 3H); 3.12 (br, 1H); 3.88 (br, 1H); 6.48 (S, 1H); 7.0–7.9 (m, 12H).

To a 300 ml four-necked flask equipped with a reflux tube, a thermometer and a dropping funnel, 1-(9-fluorenyl)-2-(2-methyl-1-indenyl)ethane (1.0 g, 3.10 mmol) and dehydrated ether (100 ml) were introduced. To the flask was dropwise added a hexane solution of n-butyllithium (1.61 mol/l, 4.04 ml, 6.51 mmol) at –78° C. over a period of 30 minutes. Then, the temperature of the system was allowed to spontaneously rise to 0° C. over a period of 5 hours, followed by stirring at 0° C. for 3 hours. The reaction mixture became an yellow slurry.

Then, the reaction mixture was cooled to –78° C., and thereto was dropwise added zirconium tetrachloride (0.760 g, 3.26 mmol) over a period of 15 minutes. Thereafter, the temperature of the system was allowed to spontaneously rise to room temperature, followed by stirring for 12 hours, The reaction mixture (orange yellow slurry) was filtered through a glass filter (G-5), and the unfiltered solid was washed with dehydrated ether (100 ml). The orange solid remaining on the filter was washed with dehydrated dichloromethane (300 ml) and filtered. Then, the solvent was distilled off from the filtrate to obtain a red orange solid (1.20 g). The solid was washed with dehydrated dichlorornethane (100 ml) and filtered to obtain 0,650 g (yield: 43%) of an aimed product [ethylene(9-fluorenyl)(2-methyl-1-indenyl)zirconium dichloride] as a red orange powder.

Data of the NMR spectrum of the compound obtained are described below.

$^1$H-NMR (CDCl$_3$, 90 MHz); 2.20 (s, 3H); 3.8–4.4 (m, 4H); 6.24 (s, 1H); 6.9–8.0 (m, 12H).

Preparation Example 7

Synthesis of dimethylsilylene(9-fluorenyl)(2-methyl-1-indenyl)zirconium dichloride To a 100 ml reactor, 20 ml of diethyl ether and 3.3 g (20 mmol) of fluorene were introduced. Under ice-cooling, to the reactor was dropwise added 12.4 ml of a hexane solution of n-butyllithium (1.61 mmol/ml) over a period of 10 minutes, followed by stirring at room temperature for 10 hours, to obtain a mixture A.

To a 200 ml reactor, 40 ml of diethyl ether and 41.2 g (320 mmol) of dimethyldichlorosilane were introduced. Under ice-cooling, to the reactor was dropwise added the above-obtained mixture A over a period of 1 hour, followed by stirring at room temperature for 1 hour. After diethyl ether and dimethyldichlorosilane were distilled off under reduced pressure, 100 ml of methylene chloride was added and stirred. Then, a solid produced was removed by means of a glass filter. From the resulting methylene chloride solution, methylene chloride was distilled off under reduced pressure. Then, the pressure of the system was reduced by means of a vacuum pump to further distill off the solvent, whereby 5.0 g of an orange oil was obtained.

To a 100 ml reactor, 40 ml of diethyl ether and 2.18 g 16.8 mmol) of 2-methylindene were introduced. Under ice-cooling, to the reactor was dropwise added 10.4 ml of a hexane solution of n-butyllithium (1.61 mmol/ml) over a period of 10 minutes, followed by stirring at room temperature for 13 hours, to obtain a mixture B.

To a 200 ml reactor, 40 ml of a diethyl ether solution of the orange oil (5.0 g) obtained by the above reaction was introduced. Under ice-cooling, to the reactor was dropwise added the above-obtained mixture B over a period of 1.5 hours, followed by stirring at room temperature for 1 day. The reaction liquid obtained was poured into a saturated ammonium chloride aqueous solution. Then, the ether phase is washed with water and dried over anhydrous magnesium sulfate. After the ether chase was concentrated, it was separated and purified by silica gel column chromatography (developer: n-hexane) to obtain 2.65 g (yield: 45%) of an aimed product [dimethylsilylene(9-fluorenyl)(2-methyl-1-indene)] as a white powder.

Data of the NMR spectrum of the compound obtained are described below.

$^1$HNMR (CDCl$_3$, 90 MHz); −4.3 (d, 6H); 2.2 (s, 3H); 3.7 (s, 1H); 4.2 (s, 1H); 6.7 (s, 1H); 7.0–8.0 (m, 12H);

To a 100 ml reactor, 50 ml of diethyl ether and 1.35 g (3.8 mmol) of dimethylsilylene(9-fluorenyl)(2-methyl-1-indene) obtained above were introduced. Under ice-cooling, to the reactor was dropwise added 4.8 ml of a hexane solution of n-butyllithium (1.60 mmol/ml) over a period of 10 minutes, and the reaction was continued at room temperature for 1 hour and then for another 2 hours under reflux. The resulting yellow slurry was cooled to −60° C., and thereto was little by little added 0.90 g (3.8 mmol) of zirconium tetrachloride. The temperature of the system was allowed to spontaneously rise to room temperature, and the reaction mixture was stirred at room temperature for 12 hours.

The mixture was refluxed over ether for 1 hour, and a solid produced was filtered through a glass filter. The solid was washed with 30 ml of diethyl ether, and the diethyl ether solution was filtered under reduced pressure. The solid obtained was washed with 100 ml of n-hexane and filtered through a glass filter to obtain 1.58 g of an aimed product [dimethylsilylene(9-fluorenyl)(2-methyl-1-indenyl) zirconium dichloride] as a brick-colored powder.

Preparation Example 8

Synthesis of diphenylsilylene(9-fluorenyl)(2-methyl-1-indenyl)zirconium dichloride To a 100 ml reactor, 30 ml of diethyl ether and 3.3 g (20 mmol) of fluorene were introduced. Under ice-cooling, to the reactor was dropwise added 12.4 ml of a hexane solution of n-butyllithium (1.61 mmol/ml) over a period of 10 minutes, followed by stirring at room temperature for 10 hours. The reaction solution was concentrated and solidified under reduced pressure. Then, the pressure of the system was reduced by means of a vacuum pump to dry the solid, whereby an yellow lithium salt was obtained.

To a 200 ml reactor, 150 ml of n-hexane and 6.6 g (26 mmol) of diphenyldichlorosilane were introduced. Under ice-cooling, to the reactor was added the lithium salt. Then, the temperature of the system was raised to room temperature, and the reaction mixture was stirred at room temperature for 12 hours. A solid produced was removed by means of a glass filter, and the filtrate was concentrated. A solid precipitated was filtered through a glass filter to obtain 4.51 g (yield: 59%) of an aimed product [9-(chlorodiphenylsilyl)fluorene] as a white powder.

Data of the NMR spectrum of the compound obtained are described below.

$^1$H-NMR (CDCl$_3$, 90 MHz); 4.58 (s, 1H); 7.0–7.90 (m, 18H).

To a 100 ml reactor, 40 ml of diethyl ether and 1:53 g (11.8 mmol) of 2-methylindene were introduced. Under ice-cooling, to the reactor was dropwise added 7.3 ml of a hexane solution of n-butyllithium (1.61 mmol/ml) over a period of 10 minutes, followed by stirring at room temperature for 10 hours, to obtain a mixture C.

To a 200 ml reactor, 50 ml of diethyl ether, 4.51 g (11.6 mmol) of 9-(chlorodiphenylsilyl)fluorene and 14.4 mg (1.2 mmol) of copper thiocyanate were introduced. Under ice-cooling, to the reactor was dropwise added the above-obtained mixture C over a period of 1 hour, and the reaction was continued at room temperature for 15 hours. After the reaction was completed, a solid precipitated was removed by means of a glass filter. The filtrate obtained was concentrated and solidified. The resulting solid was reslurried and washed with 30 ml of diethyl ether to obtain 2.10 g (yield: 37%) of an aimed product [diphenylsilylene(9-fluorenyl)(2-methyl-1-indene)] as a white powder.

Data of the NMR spectrum of the compound obtained are described below.

$^1$H-NMR (CDCl$_3$, 90 MHz); 1.98 (s, 3H); 4.42 (s, 1H); 4.95 (s, 1H); 6.20 (s, 1H); 6.60–8.40 (m, 22H).

To a 100 ml reactor, 50 ml of diethyl ether and 1.50 g (3.15 mmol) of diphenylsilylene(9-fluorenyl)(2-methyl-1-indene) obtained above were introduced. Under ice-cooling, to the reactor was dropwise added 3.9 ml of a hexane solution of n-butyllithium (1.60 mmol/mi) over a period of 10 minutes, and the reaction was continued at room temperature for 1 hour and then for another 2 hours under reflux. The resulting yellow slurry was cooled to −60° C., and thereto was little by little added 0.73 g (3.15 mmol) of zirconium tetrachloride. Then, the temperature of the system was allowed to spontaneously rise to room temperature, and the reaction mixture was stirred at room temperature for 12 hours.

The mixture was refluxed over ether for 1 hour, and a solid produced was filtered through a glass filter. The solid obtained was washed with 30 ml of diethyl ether, and the diethyl ether solution was filtered under reduced pressure. The resulting solid was washed with 100 ml of n-hexane and filtered through a glass filter to obtain 1.80 g of an aimed product [diphenylsilylene(9-fluorenyl)(2-methyl-1-indenyl) zirconium dichloride] as an orange powder.

Data of the NMR spectrum of the compound obtained are described below.

$^1$H-NMR (CDCl$_3$, 90 MHz); 2.12 (s, 3H); 6.70–8.40 (m, 13H).

Preparation Example 9

Synthesis of ethylene(9-fluorenyl)(1-indenyl) zirconium dichloride

To a 300 ml four-necked flask equipped with a reflux tube, a thermometer and a dropping funnel, indene (10 g, 86.1 mmol) and dehydrated ether (100 ml) were introduced. To the flask was dropwise added a hexane solution of n-butyllithium (1.61 mol/l, 59 ml, 94.7 mmol) at −78° C. over a period of 30 minutes. Thereafter, the temperature of the system was allowed to spontaneously rise to room temperature over a period of 3 hours. The reaction mixture became orange and transparent.

Then, to a 1 liter four-necked flask equipped with a reflux tube, a thermometer and a dropping funnel, 1,2-dibromoethane (81 g, 0.431 mol) and dehydrated ether (150 ml) were introduced. To the flask was dropwise added the whole amount of the reaction mixture obtained above over a period of 2 hours, followed by stirring at room temperature for 15 hours. The yellow transparent solution obtained was poured into 300 ml of water to separate an ether phase. The aqueous phase was extracted with ether (100 ml×3), and the combined organic phase was dried over anhydrous magnesium sulfate. Then, the solvent was distilled off, and the resulting yellow brown oil was purified by column chromatography (silica gel 500 g, developer: hexane) to obtain 16.36 g (yield: 85%) of an aimed product [3-(2-bromoethyl)indene] as a light green yellow transparent liquid.

Data of the M spectrum of the compound obtained are described below.

$^1$H-NMR (CDCl$_3$, 90 MHz); 1.8–2.6 (m, 2H); 3.40 (t, J=1.9 Hz, 2H); 3.5–3.8 (m, 1H); 6.48 (d, J=1.6 Hz, 1H); 6.83 (d, J=1.6 Hz, 1H); 7.1–7.6 (m, 4H).

To a 300 ml four-necked flask equipped with a reflux tube, a thermometer and a dropping funnel, fluorene (3.72 g, 22.4 mmol) and dehydrated ether (100 ml) were introduced. To the flask was dropwise added a hexane solution of n-butyllithium (1.61 mol/l, 15.3 ml, 24.6 mmol) a 0° C. over a period of 1 hour, and the contents of the flask were refluxed for 2 hours. The reaction mixture became dark red and transparent. Then, the mixture was cooled to −78° C. (yellow slurry), and a solution of 3-(2-bromoethyl)indene (5 g, 22.4 mmol) in dehydrated ether (50 ml) was dropwise added over a period of 1 hour. The temperature of the system was allowed o spontaneously rise to room temperature, followed by stirring for 15 hours. The reaction mixture gradually became an orange yellow homogeneous solution.

The reaction solution was poured into a saturated ammonium chloride aqueous solution (200 ml) to separate an ether layer. The aqueous layer was extracted with ether (100 ml×3), and the combined organic layer was dried over anhydrous magnesium .sulfate. Then, the solvent was distilled off, and the resulting white yellow semi-solid was purified by column chromatography (silica gel: 400 g, developer: haxane) to obtain 3.42 g (yield: 49%) of an aimed product [1-(9-fluorenyl)-2-(1-indenyl)ethylene] as a white powder.

Data of the N spectrum of the compound obtained are described below.

$^1$H-NMR (CDCl$_3$, 90 MHz); 1.1–2.6 (m, 4H); 3.35 (br, 1H); 3.97 (br, 1H); 6.48 (d, J=1.6 Hz, 1H); 6.83 (d, J=1.6 Hz, 1H); 7.1–8.0 (m, 12H); FD-MS; 308 (m$^+$).

To a 100 ml four-necked flask equipped with a reflux tube, a thermometer and a dropping funnel, 1-(9-fluorenyl)- 2-(1-indenyl)ethylene (1.0 g, 3.24 mmol) and dehydrated ether (50 ml) were introduced. To the flask was dropwise added a hexane solution of n-butyllithium (1.61 mol/l, 4.2 ml, 6.80 mmol) at −78° C. over a period of 1 hour. Then, the temperature of the system was allowed to spontaneously rise over a period of 5 hours, and the contents of the flask were refluxed for 1 hour. The reaction mixture became an orange yellow slurry.

Then, the reaction mixture was cooled to −78° C., and thereto was added zirconium tetrachloride (0.792 g, 3.40 mmol) over a period of 15 minutes. The temperature of the system was allowed to spontaneously rise to room temperature, and the reaction mixture was stirred for 12 hours. The reaction mixture (orange yellow slurry) was filtered through a glass filter (G-5), and the unfiltered solid was washed with dehydrated ether (50 ml). The orange solid remaining on the filter was washed with dehydrated dichloroethane (150 ml) and filtered. Then, the solvent was distilled off 5 from the filtrate to obtain a red orange solid (1.29 g). The solid was reslurried with dehydrated haxane (100 ml), and the resulting slurry was filtered to obtain 0.924 g (yield: 61%) of an aimed product [ethylene(9-fluorenyl)(1-indenyl)zirconium dichloride] as a red orange powder.

Data of the NMR spectrum of the compound obtained are described below.

$^1$H-NMR (CDCl$_3$, 90 MHz); 3.7–4.4 (m, 4H); 6.20 (d, J=0.8 Hz, 1H); 6.35 (d, J=0.8 Hz, 1H); 6.9–8.1 (m, 12H).

Preparation Example 10

Synthesis of dimethylsilylene(9-fluorenyl)(2-methyl-4-phenyl-1-indenyl)zirconium dichloride A 100 ml four-necked flask equipped with a reflux tube, a thermometer and a dropping fennel was thoroughly purged with nitrogen and dried. To the flask, 2-methyl-4-phenylindene (1.50 g, 7.27 mmol) prepared in accordance with the process described in Japanese Patent Laid-Open Publication No. 100579/1994 and dehydrated diethyl ether (40 ml) were introduced. Then, an n-hexane solution of n-butyllithium (7.63 mmol) was dropwise added at −78° C. with stirring. Aster the dropwise addition, the temperature of the reaction solution was allowed to spontaneously rise slowly to room temperature, and the solution was stirred at room temperature for one night, but the slurry concentration became too high to continue stirring. Therefore, dehydrated diethlyl ether (10 ml) was added. Then, 1.88 g (7.27 mmol) of dimethylsilylfluorenyl monochloride synthesized in Preparation Example 2 was added at 0° C. with stirring, and the mixture was further stirred at room temperature for 12 hours, whereby an yellow slurry was obtained. To the yellow slurry were added diethyl ether (100 ml) and a saturated ammonium chloride aqueous solution (100 ml), and the mixture was transferred into a separatory funnel to separate an organic phase. The organic phase was washed with a saturated ammonium chloride aqueous solution, water and a saturated sodium chloride aqueous solution in this order, and dried over magnesium sulfate. The solvent was removed and the remainder was purified by column chromatography (solvent: n-hexane) to obtain 1.75 g (yield: 56%) of a light yellow powder.

Data of the NMR spectrum of the compound obtained are described below.

$^1$H-NMR (CDCl$_3$, 90 MHz); −0.35 (d, 6H); 2.2 (s, 3H); 3.8 (t, 1H); 4.2 (s, 1H); 6.8 (s, 2H); 6.9–7.9 (m, 16H).

A 50 ml reactor equipped with a dropping funnel was thoroughly purged with nitrogen and dried. To the reactor, dimethylsilylene (9-fluorenyl)(2-methyl-4-phenyl-1-indene (0.80 g, 1.87 mmol) and dehydrated diethyl ether (20 ml) were introduced. Then, to the reactor was dropwise added an n-hexane solution of n-butyllithium (3.93 mmol) at −78° C. After the dropwise addition, the temperature of the reaction solution was allowed to spontaneously rise slowly to room temperature. Then, the reaction solution was stirred at room temperature for 12 hours, and to the solution was dropwise added zirconium tetrachloride (0.435 g, 1.87 mmol) at 0° C. with stirring. After the dropwise addition, the temperature of the solution was allowed to spontaneously rise slowly to room temperature. The solution was then stirred at room temperature for 6 hours. The resulting red slurry was filtered through a glass filter, and the solid obtained was quickly washed with dried dichloromethane. The solvent was removed from the filtrate, and the remainder was reslurried with 40 ml of dehydrated hexane. The resulting slurry was filtered through a glass filter to obtain 560 mg (yield: 51%) of an aimed compound as a red powder.

Preparation Example 11

Synthesis of ethylene(2,7-di-t-butyl-9-fluorenyl)(2-methyl-1-indenyl)zirconium dichloride Synthesis of 2,7-di-t-butyl-9-fluorene To a 100 ml four-necked flask equipped with a reflux tube, a thermometer and a dropping funnel, fluorene (3.4 g, 20.5 mmol), 2,6-di-butyl-p-cresol (4.4 g, 20.0 mmol) and nitromethane (30 ml) were introduced. In a water bath (10° C.), to the flask was dropwise added a solution of anhydrous aluminum chloride (4 g) in nitromethane (6 ml) with stirring over a period of 1 hour (the reaction liquid gradually became a purple heterogenous mixture) After a three hours stirring, the resultant reaction mixture was powered into 300 ml of ice-cold water and indroduced into a separatory funnel to separate an organic phase. The aqueous phase was extracted with ether (200 ml×3) and the organic phases thus obtained were combined. From the combined organic phase, ether and nitromethane were completely removed by means of an evaporator and an oil pump, and the residue was dissolved in 200 ml of ether, followed by washing with a 10% aqueous solution of sodium hydroxide (150 ml×3). The resultant product was dried over anhydrous magnesium sulfate. Then, the solvent was distilled off, and the resulting white yellow powder was recrystallized from methanol to obtain 3.5 g (yield: 63%) of an aimed product of a white yellow needle-like crystal.

Data of the NMR spectrum of the compound obtained are described below.

$^1$H-NMR (CDCl$_3$, 90 MHz); 1.38 (s, 18H); 3.85 (s, 2H); 7.2–7.8 (m, 6H).

Synthesis of 3-(2-bromoethyl)-2-methylindene

To a 200 ml four-necked flask equipped with a reflux tube, a thermometer and a dropping funnel, 2-methylindene (4.5 g, 34.6 mmol) and dehydrated ether (50 ml) were introduced. To the flask was dropwise added a hexane solution of n-butyllithium (1.61 mol/l, 23.7 ml, 38.1 mmol) at −78° C. over a period of 1 hour. Then, the temperature of the system was allowed to spontaneously rise to room temperature over a period of 6 hours. The reaction mixture became a yellow orange anionic slurry.

Then, to a 500 ml four-necked flask equipped with a reflux tube, a thermometer and a dropping funnel, 1,2-dibromethane (32.5 g, 0.173 mol) and dehydrated ether (100 ml) were introduced. To the flask was added the whole amount of the anionic slurry obtained above at 0° C. over a period of 1 hour, followed by stirring at room temperature for 15 hours. The resulting yellow transparent solution was poured into 300 ml of water to separate an ether phase. The aqueous phase was extracted with ether (100 ml×3), and a combined organic phase was dried over anhydrous magnesium sulfate. Then, the solvent was distilled off, and the resulting yellow brown oil was purified by column chromatography (solvent: hexane) to obtain 6.25 g (yield: 76%) of an aimed product of a yellow white transparent liquid.

Data of the NMR spectrum of the compound obtained are described below.

$^1$H-NMR (CDCl$_3$, 90 Mz); 1.8–2.6 (m, 2H); 1.93 (s, 3H); 2.8–3.2 (m, 2H); 3.3 (br, 1H); 6.32 (s, 1H); 6.5–7.4 (m, 4H).

Synthesis of 1-(2,7-di-t-butyl-9-fluorenyl)-2-(2-methyl-1-indenyl)ethylene

To a 100 ml four-necked flask equipped with a reflux tube, a thermometer and a dropping funnel, 2,7-di-t-butylfluorene (1.18 g, 4.22 mmol) and dehydrated ether (30 ml) were introduced. To the flask was dropwise added a hexane solution of n-butyllithium (1.67 mol/l, 2.8 ml, 4.64 mmol) at 0° C. over a period of 1 hour, followed by stirring at room temperature for 7 hours. The reaction liquid became red orange transparent. Then, the liquid was cooled to −78° C. (a yellow orange slurry), to which a solution of 3-(2-bromoethyl)-2-methylindene (1 g, 4.22 mmol) in dehydrated ether (10 ml) was dropwise added over a period of 30 minutes. Then, the temperature of the system was allowed to spontaneously rise to room temperature, followed by stirring for 15 hours. The reaction mixture gradually became a yellow slurry. The resulting yellow slurry was poured into 200 ml of a saturated ammonium chloride aqueous solution to separate an ether phase. The aqueous phase was extracted with ether (100 ml×2), and a combined organic phase was dried over anhydrous magnesium sulfate, Then, the solvent was distilled off, and the resulting white yellow powder was reslurried with hexane (100 ml) and filtrated to obtain 1.70 g (yield: 93%) of an aimed product of a white powder.

Data of the NMR spectrum of the compound obtained are described below.

$^1$H-NMR (CDCl$_3$, 90 MHz); 1.3–1.9 (m, 4H); 1.40 (s, 18H); 1.91 (br, 3H); 3.08 (br, 1H); 3.85 (br, 1H); 6.48 (br, 1H); 7.0–7.9 (m, 10H).

Synthesis of ethylene(2,7-di-t-butyl-9-fluorenyl)(2-methyl-1-indenyl)zirconium dichloride To a 300 ml four-necked flask equipped with a reflux tube, a thermometer and a dropping funnel, 1-(2,7-di-t-butyl-9-fluorenyl)-2-(2-methyl-1-indenyl)ethylene (0.5 g, 1.15 mmol) and dehydrated ether (50 ml) were introduced. To the flask was dropwise added a hexane solution of n-butyllithium (1.67 mol/l, 1.45 ml, 2.42 mmol) at −78° C. over a period of 30 minutes. Then, the temperature of the system was allowed to spontaneously rise to room temperature over a period of 15 hours. The reaction liquid became a orange yellow slurry.

Then, the slurry was cooled to −78° C., to which zirconium tetrachloride (0.282 g, 1.21 mmol) was added over a period of 15 minutes. The temperature of the system was allowed to spontaneously rise to room temperature, followed by stirring for 12 hours. The reaction mixture (orange yellow slurry) was faltered under pressure through a glass filter (G-5), and the substance remained on the filter was washed with dehydrated ether (20 ml×2). Then, the solvent was distilled off from the filtrate by means of an oil pump to obtain a red orange solid. The solid was washed with dehydrated hexane (10 ml×2) to obtain 0.300 g (yield: 44%) of an aimed product of a red orange powder.

Data of the NMR spectrum of the compound obtained are described below.

$^1$H-NMR (CDCl$_3$, 90 MHz); 1.2–1.4 (m, 18H); 2.20 (s, 3H); 3.6–4.2 (m, 4H); 6.10 (s, 1H); 6.8–7.8 (m, 10H).

Preparation Example 12

Synthesis of dimethylsilylene(3-methyl-1-indenyl)(9-fluorenyl)zirconium dichloride Synthesis of dimethyl(9-fluorenyl)silane chloride A 1 liter four-necked flask equipped with a reflux tube, a thermometer and a dropping funnel was thoroughly purged with nitrogen and dried. To the flask, fluorene (5.00 g, 30 mmol) and dehydrated ether (100 ml) were introduced and, then, a hexane solution of n-butyllithium (30 mmol) was dropwise added at −10° C. with stirring over a period of 30 minutes. After the dropwise addition of the hexane solution, the temperature of the system was allowed to spontaneously and slowly rise to room temperature, followed by stirring at room temperature for 4 hours. The reaction liquid became a yellow slurry. Them, the slurry was dropwise added to a dichlorodimethylsilane (18.24 ml, 150 mmol)/dehydrated ether (100 nl) solution at −10° C. with stirring over a period of 1 hour. The temperature of the system was allowed to spontaneously rise to room temperature, followed by stirring over night. The reaction solution was filtered under pressure through a glass filter (G-5) to remove lithium chloride, and the solvent and the unreacted dichlorodimethylsilane remained in the filtrate were removed under reduced pressure. The resultant product was reslurried with dehydrated ether (100 ml) and the obtained slurry was filtered under pressure through a glass filter (C-5) to obtain 3.30 g of a white powder (yield: 43%).

Data of the NMR spectrum of the compound obtained are described below.

$^1$H-NMR (CDCl$_3$); 7.2–8.0 (m); 4.1 (s, 1H); 0.15 (s, 6H).
Synthesis of dimethyl(1-indenyl)(9-fluorenyl)silane A 200 ml four-necked flask equipped with a reflux tube, a thermometer and a dropping funnel was thoroughly purged with nitrogen and dried. To the flask, indene (3.00 g, 25.8 mmol) and dehydrated ether (40 ml) were introduced. To the flask was dropwise added a hexane solution of n-butyllithium (25.8 mmol) at 0° C. with stirring. Then, the temperature of the system was allowed to spontaneously and slowly rise to room temperature, followed by stirring at room temperature for 2 hours. The reaction liquid became an orange solution. To the solution, the dimethyl(9-fluorenyl) silane chloride obtained above (6.69 g, 25.8 mmol) was dropwise added at a 0° C. with stirring. Then, the temperature of the reaction mixture was allowed to slowly and spontaneously rise to room temperature. The reaction mixture was stirred at room temperature for 2 hours to obtain a yellow slurry. To the slurry, ether (100 ml) and a saturated aqueous solution (100 ml) of ammonium chloride were added and the mixture obtained was introduced into a separatory funnel to separate the organic phase. The aqueous phase was extracted by ether (100 ml×3) and a combined organic phase was washed with a saturated aqueous solution of sodium chloride and dried over anhydrous magnesium sulfate. After the solvent was distilled off, it was purified by column chromatography (developer: hexane) to obtain 4.70 g of a white powder (yield: 54%).

Data of the NMR spectrum of the compound obtained are described below.

$^1$H-NMR (CDCl$_3$); 7.2–8.0 (m); 6.9 (m, 1H); 6.3 (dd, 1H); 4.1 (s, 1H); 3.6 (t, 1H); −0.2 (s. 3H); −0.4 (s, 3H).
Synthesis of dimethyl(3-methyl-1-indenyl)(9-fluorenyl) silane A 200 ml four-necked flask equipped with a reflux tube, a thermometer and a dropping tunnel was thoroughly purged with nitrogen and dried. To the flask, dimethyl(1-indenyl) (9-fluorenyl)silane (2.00 g, 5.91 mmol) synthesized above and dehydrated ether (50 ml) were introduced. To the flask was dropwise added a hexane solution of n-butyllithium (6.21 mmol) at −40° C. with stirring. The temperature of the reaction liquid was allowed to spontaneously and slowly rise to room temperature. After stirring over night, the reaction liquid became a yellow solution. To the solution, methyl iodide (3.78 g, 26.6 mmol) was added and the temperature of the system was allowed to spontaneously and slowly rise to room temperature, followed by stirring for one day. The reaction liquid became an orange solution. To the resulting solution, 100 ml of ether and 100 ml of a saturated aqueous solution of ammonium chloride were added and the mixture was introduced into a separatory funnel to separate an organic phase. The organic phase was washed with water and a saturated aqueous solution of sodium chloride and dried over anhydrous magnesium sulfate. After the solvent was distilled off, it was purified by column chromatography (developer: hexane) to obtain two kinds of isomers (one was a colourless transparent liquid, the other was a yellow liquid) totalling to 1.85 g (yield: 89%).

Data of the NMR spectrum of the compound obtained are described below.

$^1$H-NMR (CDCl$_3$); two kinds of isomers (A:B=4:1);
Isomer A; 7.2–8.0 (m, 12H); 6.5 (d, 1H); 4.1 (s, 1H); 3.6 (dd, 1H); 1.2 (d, 3H); 0.1 (d, 6H);
Isomer B 7.2–8.0 (m, 12H); 6.1 (d, 1H); 4.0 (s, 1H); 3.6 (dd, 1H); 2.1 (d, 3H); −0.3 (d, 6H).

Synthesis of dimethylsilylene(3-methyl-1-indenyl) (9-fluorenyl)zirconium dichloride A 50 ml Schlenk's bottle equipped with a dropping funnel was thoroughly purged with nitrogen and dried. To the bottle, the dimethyl(3-methyl-1-indenyl)(9-fluorenyl)silane (0.80 g, 2.27 mmol) synthesized above and dehydrated ether (20 ml) were introduced. Under stirring at −78° C, a hexane solution of n-butyllithium (4.76 mmol) was dropwise added. After the dropwise addition, the temperature of the system was allowed to spontaneously and slowly rise to room temperature. By an over night stirring, the yellow solution became a red solution. To the resultant solution, zirconium tetrachloride (0,53 g, 2.27 mmol) was dropwise added at −78° C. with stirring. After the addition, the temperature of the system was allowed to spontaneously and slowly rise to room temperature and the reaction mixture was stirred over night. The reaction liquid became a red slurry. The ether was removed by means of pressure filteration through a glass filter (G-5), the substance remained on the filter was immediately washed with dehydrated dichloromethane (the substance was lithium chloride). After the solvent in the filtrate thus obtained was removed, the resultant product was reslurried with dehydrated hexane (25 ml) and filtered by means of a glass filter (G-5) to obtain the aimed product metallocene as an orange powder (330 mg, yield: 28%).

Preparation Example 13

Synthesis of ethylene(2-methyl-4-phenyl-1-indenyl) (9-fluorenyl)zirconium dichloride
Synthesis of 3-(2-bromoethyl)-2-methyl-4-phenylindene A 200 ml four-necked flask equipped with a reflux tube, a thermometer and a dropping funnel was thoroughly purged with nitrogen and dried. To the flask, 2-methyl-4-phenylindene (2.50 g, 12.12 mmol) and dehydrated ether (50 ml) were introduced. To the flask, a hexane solution of n-butyllithium (12.73 mmol) was dropwise added at 0° C. over a period of 30 minutes. Then, the temperature of the system was allowed to spontaneously and slowly rise to room temperature, followed by stirring at room temperature For 4 hours. The reaction liquid became a yellow slurry.

Then, the slurry was dropwise added to a dibromoethane (5.22 ml, 60.6 mmol)/dehydrated ether (20 ml) solution at 0° C. with stirring over a period of 1 hour. The resultant mixture was allowed to become at room temperature, followed by stirring at this temperature over night. The reaction liquid was a yellow solution. The solution was poured into 100 ml of ether and 100 ml of a saturated aqueous solution of ammonium chloride, and the mixture was introduced into a separatory funnel to separate an organic phase. The organic phase was washed with a saturated aqueous solution of ammonium chloride, water and a saturated aqueous solution of sodium chloride, and dried over anhydrous magnesium sulfate. After the solvent was distilled off, the yellow oil thus obtained was purified by column chromatography (developer: hexane) to obtain 3.00 g of a light yellow oil (yield: 79%).

Data of the NMR spectrums of the compound obtained are described below.

$^1$H-NMR (CDCl$_3$, 90 MHz); 2.0–2.8 (m, 2H); 2.1 (s, 3H); 3.0–3.8 (m); 3.5 (br, 1H); 6.7 (s, 1H); 7.1–7.8 (m, 8H).

Synthesis of 1-(9-fluorenyl)-2-(2-methyl-4-phenyl-1-indenyl)ethylene

A 200 ml four-necked flask equipped with a reflux tube, a thermometer and a dropping funnel was thoroughly purged with nitrogen and dried. To the flask, fluorene (1.29 g, 7.76 mmol) and dehydrated ether (23 ml) were introduced. To the flask, a hexane solution of n-butyllithium (8.15 mmol) was dropwise added at 0° C. with stirring over a period of 30 minutes. The temperature of the reaction mixture was allowed to spontaneously and slowly rise to room temperature and the reaction mixture was stirred at room temperature for 1.5 hours. The reaction liquid became a brown slurry. The slurry was dropwise added to a 3-(2-bromomethyl)-2-methyl-7-phenylindene (2.42 g, 7.73 mmol)/dehydrated ether (40 ml) solution at 0° C. with stirring over a period of 1 hour. The resultant mixture was allowed to become at room temperature, followed by stirring at this temperature over night. The red purple solution became a dark orange solution. To the solution, ether (100 ml) and a saturated aqueous solution (100 ml) of ammonium chloride were added and the mixture was introduced into a separatory funnel to separate an organic phase. The organic phase was washed with a saturated aqueous solution of ammonium chloride, water and a saturated aqueous solution of sodium chloride, and dried over anhydrous magnesium sulfate. After the solvent was distilled off, it was purified by column chromatography (developer: hexane) to obtain an orange oil. The oil was foamed and solidified under reduced pressure by means of a vacuum pump, thereby to obtain 1.10 g of a pale orange powder (yield: 36%).

Data of the NNR spectrum of the compound obtained are described below.

$^1$H-NMR (CDCl$_3$, 90 MHz); 1.3–1.9 (m, 4H); 1.91 (br, 3H); 3.08 (br, 1H); 3.85 (br, 1H); 6.48 (br, 1H); 7,0–7.9 (m, 10H).

Synthesis of ethylene(2-methyl-4-phenyl-1-indenyl)9-fluorenyl)zirconium dichloride A 50 ml Schlenk's bottle equipped with a dropping funnel was thoroughly purged with nitrogen and dried. To the bottle, the 1-(9-fluorenyl)-2-(2-methyl-4-phenyl-1-indenyl) ethylene (0.50 g, 1.25 mmol) obtained above and dehydrated ether (20 ml) were introduced. To the flask, a hexane solution of n-butyllithium (2.63 mmol) was dropwise added at –78° C. with stirring. Then, the temperature of the system was allowed to spontaneously and slowly rise to room temperature. The reaction was stirred at room temperature over night, whereby a yellow orange solution came, through a brown solution and a dark orange slurry, to a brown orange slurry, Then, zirconium tetrachloride (0.307 g, 1.31 mmol) was dropwise added at –78° C. with stirring and the temperature of the system was allowed to spontaneously rise to room temperature. By stirring overnight at room temperature, the yellow brown slurry became an orange slurry, The ether was removed by means of pressure filteration through a glass filter (G-5), the substance remained on the filter was immediately washed with dehydrated dichloromethane (the substance was lithium chloride). After the solvent in the filtrate thus obtained was removed, the resultant product was reslurried with dehydrated hexane (30 ml) and filtered by means of a glass filter (G-5) to obtain the aimed product metallocene as a red orange powder (320 mg, yield: 46%)

Data of the NMR spectrum of the compound obtained are described below.

$^1$H-NMR (CDCl$_3$, 90 MHz); 2.20 (s, 3H); 3.6–4.2 (m, 4H); 6.10 (s, 1H); 6.8–8.0 (m, 16H).

Preparation Example 14

Synthesis of dimethylsilylene(2-methyl-4-i-propyl-7-methyl-1-indenyl)(9-fluorenyl)zirconium dichloride Synthesis of dimethyl(9-fluorenyl)silane chloride A 1 liter four-neck flask equipped with a reflux tube, a thermometer and a dropping funnel was thoroughly purged with nitrogen and dried. To the flask, fluorene (5.00 g, 30 mmol) and dehydrated ether (100 ml) were introduced. Under stirring at –10° C., a hexane solution of n-butyllithium (30 mmol) was dropwise added over a period of 30 minutes. After the dropwise addition, the temperature of the system was allowed to spontaneously and slowly rise to room temperature, followed by stirring at room temperature for 4 hours. The reaction, liquid became a yellow slurry. The slurry was dropwise added to a dichlorodimehylsilane (18.24 ml, 150 mmol)/dehydrated ether (100 ml) solution under stirring at –10° C. over a period of 1 hour. After the temperature of the system was allowed to spontaneously rise to room temperature, the reaction mixture was stirred over night. Lithium chloride was removed by means of pressure filteration of the resulting solution using a glass filter (G-5). Further the solvent and the unreacted dichlorodimethylsilane remained in the filtrate were removed under reduced pressure. The resulting filtrate was reslurried with dehydrated hexane (100 ml) and subjected to pressure filteration using a glass filter (G-5) to obtain a white powder (3.30 g, yield: 43%).

Data of the NMR spectrum of the compound obtained are described below.

$^1$H-NMR (CDCl$_3$); 7.2–8.0 (m, 8H); 4.1 (s, 1H); 0.15 (s, 6H).

Synthesis of dimethyl(2-methyl-4-i-propyl-7-methyl-1-indenyl)(9-fluorenyl)silane A 100 ml four-necked flask equipped with a reflux tube, a thermometer and a dropping funnel was thoroughly purged with nitrogen and dried. To the flask, 2-methyl-4-i-propyl-7-methylindene (1.50 g, 8.06 mmol) and dehydrated ether (25 ml) were introduced. Under stirring at –78° C., a hexane solution of n-butyllithium (8.46 mmol) was dropwise added. After the dropwise addition, the temperature of the system was allowed to spontaneously and slowly rise to room temperature. The reaction mixture was stirred at room temperature over night, whereby a colourless solution came, through a white slurry and a light yellow slurry, to a yellow slurry. To the slurry, the dimethyl(9-fluorenyl)silane chloride (2.06 g, 8.06 mmol) synthesized above was added under stirring at 0° C., followed by stirring at room temperature for 1.5 hours. After ether (100 ml) and a saturated ammonium chloride aqueous solution (100 ml) were added, the resulting mixture was introduced into a separatory funnel to separate out an organic phase. The organic phase was washed with a saturated ammonium chloride aqueous solution, water and a saturated sodium chloride aqueous solution, and dried over anhydrous magnesium sulfate. After the solvent was removed, the obtained product (a yellow oil) was purified by column chromatography (developer: hexane) to obtain 1.50 g so a yellow oil (yield: 46%).

Data of the NMR spectrum of the compound obtained are described below.

$^1$H-NMR (CDCl$_3$, 90 MHz); 6.6–8.0 (m, 11H); 4.2 (s, 1H); 3.7 (s, 1H); 2.65–3.05 (m, 1H); 2.45 (s, 3H); 2.25 (s, 3H); 1.1–1.3 (d, 6H); –0.35 (d, 6H).

Synthesis of dimethylsilylene(2-methyl-4-i-propyl-7-methyl-1-indenyl)(9-fluorenyl)zirconium dichloride A 50 ml Schlienk's bottle equipped with a dropping funnel was thoroughly purged with nitrogen and dried. To the bottle, the dimethyl(2-methyl-4-i-propyl-7-methyl-1-indenyl)(9-fluorenyl)silane (0.80 g, 1.96 mmol) synthesized above and dehydrated ether (20 ml) were introduced. Under stirring at −78° C., a hexane solution of n-butyllithium (4.11 mmol) was dropwise added. After the dropwise addition, the temperature of the system was allowed to spontaneously and slowly rise to room temperature. By the overnight stirring, the lemon yellow solution became a bright yellow solution, then a red brown solution. To the solution, zirconium tetrachloride (0.436 g, 1.96 mmol) was dropwise added at −78° C. Under stirring. The temperature of the system was allowed to spontaneously and slowly rise to room temperature. The reaction mixture was stirred for 8 hours at room temperature to obtain a red slurry. The ether was removed by means of pressure filteration using a glass filter (G-5), and the substance remained on the filter was immediately washed with dehydrated dichloromethane (the substance was lithium chloride). After the solvent in the filtrate thus obtained was removed, the resultant product was reslurried with dehydrated hexane (30 ml) and filtered by means of a glass filter (G-4) to obtain the aimed product metallocene as a red powder (50 mg, yield: 4%).

Preparation Example 15

Synthesis of dimethylsilylene(2,3-dimethyl-1-indenyl)(9-fluorenyl)zirconium dichloride Synthesis of dimethyl(9-fluorenyl)silane chloride A 1 filter four-necked flask equipped with a reflux tube, a thermometer and a dropping funnel was thoroughly purged with nitrogen and dried. To the flask, fluorene (5.00 g, 30 mmol) and dehydrated ether (100 ml) were introduced and, then, a hexane solution of n-butyllithium (30 mmol) was dropwise added thereto at −10° C. with stirring over a period of 30 minutes. After he dropwise addition of the hexane solution, the temperature of the system was allowed to spontaneously and slowly rise to room temperature, followed by stirring at room temperature for 4 hours. The reaction liquid became a yellow slurry.

Then, the slurry was dropwise added to a dichlorodimethylsilane (18.24 ml, 150 mmol)/dehydrated ether (100 ml) solution at −10° C. with stirring over a period of 1 hour. The temperature of the system was allowed to spontaneously rise to room temperature, followed by stirring over night. The reaction solution was filtered under pressure through a glass filter (G-5) to remove lithium chloride, and the solvent and the unreacted dichlorodimethylsilane remained in the filtrate were removed under reduced pressure. The resultant product was reslurried with dehydrated ether (100 ml) and the obtained slurry was filtered under pressure through a glass filter (G-5) to obtain 3.30 g of a white powder(yield: 43%).

Data of the NMR spectrum of the compound obtained are described below.

7.2–8.0 (m, 8H); 4.1 (s, 1H); 0.15 (s, 6H).

Synthesis of 1,2-dimethylindene

A 200 ml four-necked flask equipped with a reflux tube, a thermometer and a dropping funnel was thoroughly purged with nitrogen and dried. To the flask, methylmagnesium bromide (3.0 mol/l ether solution) (16.9 ml, 50.7 mmol) and dehydrated ether (50 ml) were introduced. To the flask, a solution of 2-methyl-1-indanon (3.70 g, 25.3 mmol) in dehydrate ether (20 ml) was dropwise added at room temperature with stirring. Then, the reaction mixture was stirred for 2 hours and poured into cold water. The resultant mixture was introduced into a separatory funnel to separate an organic phase. The aqueous phase was extracted by ether (100 ml×3) and a combined organic phase was washed with a saturated aqueous solution of ammonium chloride, water and a saturated aqueous solution of sodium chloride, and dried over anhydrous magnesium sulfate. The solvent was distilled off to obtain 1,2-dimethyl-1-hydroxy-indene. The compound thus obtained was dissolved in toluene (30 ml) and, thereto, 0.1 g of p-toluenesulphonic acid was added. The reaction mixture was refluxed for 3 hours to remove water. The organic phase thus obtained was introduced into a separatory funnel and washed with a saturated aqueous solution of ammonium chloride, water and a saturated aqueous solution of sodium chloride, and dried over anhydrous magnesium sulfate. After removing a solvent, it was purified by column chromatography (developer; hexane) to obtain 2.70 g (GC 94%) of a pale yellow solution (yield: 74%).

Data of the NMR spectrum of the compound obtained are described below.

$^1$H-NMR (CDCl$_3$, 90 MHz); 7.1–7.6 (m, 4H); 3.2 (s, 2H); 2.0 (s, 6H).

Synthesis of dimethyl(2,3-dimethyl-1-indenyl)(9-fluorenyl)silane

A 200 ml four-necked flask equipped with a reflux tube, a thermometer and a dropping funnel was thoroughly purged with nitrogen and dried. To tale flask, the 1,2-dimethiylindene (1.60 g, 11.09 mmol) synthesized above and dehydrated ether (40 ml) were introduced. To the flask, a hexane solution of n-butyllithium (11.6 mmol) was dropwise added at 0° C. with stirring. The temperature of the system was allowed to spontaneously and slowly rise to room temperature. After stirring over night, the reaction liquid became a milk white slurry. To the slurry, the dimethyl (9-fluorenyl)silane chloride (2.72 g, 10.51 mmol) synthesized above was added, followed by stirring at room temperature for 2 hours. The reaction liquid became a yellow slurry. To the slurry, N-methyl-2-pyrrolidine (0.1 g) was added, followed by stirring at room temperature for 1.5 hours. To the resultant mixture, 100 ml of ether and 100 ml of a saturated aqueous solution of ammonium chloride were added and the mixture was introduced into a separatory funnel to separate an organic phase. The organic phase was washed with a saturated aqueous solution of ammonium chloride, water and a saturated aqueous solution of sodium chloride, and dried over anhydrous magnesium sulfate. After the solvent was distilled off, it was purified by column chromatography (developer; hexane) to obtain 1.10 g of a yellow powder (yield: 27%).

Data of the NMR spectrum of the compound obtained are described below.

$^1$H-NMR (CDCl$_3$, 90 MHz); 6.7–8.0 (m, 12H); 4.5 (s, 1H); 3.6 (t, 1H); 2.0 (s, 6H); –0.4 (s, 6H).

Synthesis of dimethylsilylene(2,3-dimethyl-1-indenyl)(9-fluorenyl)zirconium dichloride A So ml Schlenk's bottle equipped with a dropping funnel was thoroughly purged with nitrogen and dried. To the bottle, the dimethyl(2,3-dimethyl-1-indenyl)(9-fluorenyl) silane (0.80 g, 2.18 mmol) synthesized above and dehydrated ether (15 ml) were introduced. Under stirring at −78° C., a hexane solution of n-butyllithium (4.58 mmol) was dropwise added. After the dropwise addition, the temperature of the system was allowed to spontaneously and slowly rise to room temperature. By stirring for 8 hours at room temperature, the pale yellow solution came, through a yellow solution, to a yellow slurry. To the slurry, zirconium tetrachloride (0.509 g, 2.18 mmol) was dropwise added at −78° C. with stirring. After the addition, the temperature of the system was allowed to spontaneously and slowly rise to room temperature and the reaction mixture was stirred overnight. The reaction liquid became a red slurry. The ether was removed by means of pressure filteration through a glass filter (G-5), the substance remained on the filter was immediately washed with dehydrated dichloromethane (the substance was lithium chloride) After the solvent in the filtrate thus obtained was removed, the resultant product was reslurried with dehydrated hexane (30 ml ) and filtered by means of a glass filter (G-5) to obtain the aimed product metallocene as a red powder (427 mg, yield: 37%).

Example 1

Preparation of Catalyst Solution

To a glass flask thoroughly purged with nitrogen, 5.8 mg of dimethylsilylene(2-methyl-4,5-benzo-1-indenyl)(2,7-di-t-butyl-9-fluorenyl)zirconium dichloride (compound a) was introduced, and thereto were added 1.57 ml of a toluene solution of methylaluminoxane (MAO) (Al: 1.1 mol/l) and 2.76 ml of toluene to obtain a catalyst solution.

Polymerization

To a 2 liter stainless steel autoclave thoroughly purged with nitrogen, 600 ml of hexane and 150 ml of 1-octene were introduced, and the temperature of the system was raised to 130° C. Then, 1 mmol of triisobutylaluminum (TIBA) and 1.0 ml (0.002 mmol in terms of Zr) of the catalyst solution prepared above were injected into the system together with ethylene to initiate polymerization. Thereafter, only ethylene was continuously fed so that the total pressure was kept at 30 kg/cm$^2$-G, and the polymerization was carried out at 140° C. for 8 hours. To the system was added a small amount of ethanol to terminate the polymerization, and the unreacted ethylene was purged out. The resulting polymer solution was introduced into a large excess of methanol to precipitate a polymer. The polymer was recovered by filtration and dried overnight at 130° C. Under reduced pressure. As a result, 61.3 g of an ethylene-1-octene copolymer having MFR of 0.21 g/10 min and a density of 0.898 g/cm$^3$ was obtained. The results are set forth in Table 1.

Example 2

To a 2 liter stainless steel autoclave thoroughly purged with nitrogen, 600 ml of hexane and 400 ml of 1-octene were introduced, and the temperature of the system was raised to 130° C. Then, 1 mmol of triisobutylaluminum and 1.0 ml (0.002 mmol in terms of Zr) of the catalyst solution prepared above were injected into the system together with ethylene to initiate polymerization. Thereafter, only ethylene was continuously fed so that the total pressure was kept at 30 kg/cm$^2$-G, and the polymerization was carried out at 140° C. for 15 minutes. To the system was added a small amount of ethanol to terminate the polymerization, and the unreacted ethylene was purged out. The resulting polymer solution was introduced into a large excess of methanol to precipitate a polymer. The polymer was recovered by filtration and dried overnight at 130° C. Under reduced pressure. As a result, 75.7 g of an ethylene-1-octene copolymer having MFR of 0.47 g/10 min and a density of 0.875 g/cm$^3$ was obtained. The results are set forth in Table 1.

Example 3

Polymerization of ethylene and 1-octene was carried out in the same manner as in Example 1 except that dimethylsilylene(2-methyl-4,5-benzo-1-indenyl)(9-fluorenyl)zirconium dichloride (compound b) synthesized in Preparation Example 2 was used instead of the compound a and the polymerization time was changed to 30 minutes.

The results are set forth in Table 1.

Example 4

Polymerization of ethylene and 1-octene was carried out in the same manner as in Example 1 except that dinethylsilylene(2,6-dimethyl-4,5-benzo-1-indenyl)(2,7-di-t-butyl-9-fluorenyl)zirconium dichloride (compound c) synthesized in Preparation Example 3 was used instead of the compound a and the polymerization time was changed to 15 minutes.

The results are set forth in Table 1.

Example 5

Polymerization of ethylene and 1-octene was carried out in the same manner as in example 1 except that dimethylsilylene(2,7-dimethyl-4,5-(2-methyl-benzo)-1-indenyl)(2,7-di-t-butyl-9-fluorenyl)zirconium dichloride (compound d) synthesized in Preparation Example 4 was used instead of the compound a and the polymerization time was changed to 15 minutes.

The results are set forth in Table 1.

Example 6

Polymerization of ethylene and 1-octene was carried out in the same manner as in Example 1 except that dimethylsilylene(2-n-propyl-4-(9-phenanthryl)-1-indenyl)(9-fluorenyl)zirconium dichloride (compound e) synthesized in Preparation Example 5 was used instead of the compound a and the polymerization time was changed to 30 minutes.

The results are set forth in Table 1.

Example 7

Preparation of Catalyst Solution

To a glass flask thoroughly purged with nitrogen, 5 ml of n-texane, and further, 1 ml (0.002 mmol in terms of Zr atom) of a toluene solution of dimethylsilylene(2-methyl-4,5-benzo-1-indenyl)(2,7-di-t-butyl-9-fluorenyl)zirconium dichloride (compound a) and 1 ml (0.004 mmol in terms of B atom) of a toluene solution of triphenylcarbeniumtetrakis (pentafluorophenyl) borate were introduced to obtain a catalyst solution.

Polymerization

To a 2 liter stainless steel autoclave thoroughly purged with nitrogen, 600 ml of hexane and 150 ml of 1-octene were introduced, and the temperature of the system was raised to 130° C. Then, 0.5 mmol of triisobutylaluminum (TIBA) and the catalyst solution prepared above were injected into the system together with ethylene to initiate polymerization. Thereafter, only ethylene was continuously fed so that the total pressure was kept at 30 kg/cm²-G, and the polymerization was carried out at 140° C. for 30 minutes. To the system was added a small amount of ethanol to terminate the polymerization, and the unreacted ethylene was purged out. The resulting polymer solution was purged into a large excess of methanol to precipitate a polymer. The polymer was recovered by filtration and dried overnight at 130° C. Under reduced pressure. As a result, 98.8 g of an ethylene-1-octene copolymer having MFR of 0.51 g/10 min. a density of 0.892 g/cm³ and Mw/Mn of 2.0 was obtained.

Comparative Example 1

An ethylene-1-octene copolymer was prepared in the same manner as in Example 1 except that dimethylsilylene (1-indenyl)(9-fluorenyl)zirconium dichloride (compound x) was used in place of the compound a and the polymerization time was varied to 30 minutes. As a result, 17.7 g of an ethylene-1-octene copolymer having MFR, of 15.9 g/10 min, a density of 0.920 g/cm³ and Mw/Mn of 2.3 was obtained. The results are set forth in Table 1.

TABLE 1

| | Component (A) | | | | | |
|---|---|---|---|---|---|---|
| | Kind | Amount (mmol) | MAO (mmol) | TIBA (mmol) | 1-Oct-ene (ml) | Hexane (ml) | Pressure *1 |
| Ex. 1 | a | 0.002 | 0.4 | 1.0 | 150 | 850 | 30 |
| Ex. 2 | a | 0.002 | 0.4 | 1.0 | 400 | 600 | 30 |
| Ex. 3 | b | 0.002 | 0.4 | 1.0 | 150 | 850 | 30 |
| Ex. 4 | c | 0.002 | 0.4 | 1.0 | 150 | 850 | 30 |
| Ex. 5 | d | 0.002 | 0.4 | 1.0 | 150 | 850 | 30 |
| Ex. 6 | e | 0.002 | 0.4 | 1.0 | 150 | 850 | 30 |
| Comp. Ex. 1 | x | 0.002 | 0.4 | 1.0 | 150 | 850 | 30 |

| | Temperature °C. | Time (min.) | Yield (g) | MFR (g/10 min) | Density (g/cm³) | Polymerization activity *2 | Molecular weight distribution Mw/Mn |
|---|---|---|---|---|---|---|---|
| Ex. 1 | 140 | 8 | 61.3 | 0.21 | 0.898 | 230 | 2.1 |
| Ex. 2 | 140 | 15 | 75.7 | 0.47 | 0.875 | 151 | 2.0 |
| Ex. 3 | 140 | 30 | 29.1 | 0.98 | 0.9902 | 29 | 2.2 |
| Ex. 4 | 140 | 15 | 140 | 0.18 | 0.894 | 280 | 2.1 |
| Ex. 5 | 140 | 15 | 109 | 0.27 | 0.899 | 218 | 2.0 |
| Ex. 6 | 140 | 30 | 38.2 | 1.10 | 0.887 | 38 | 2.1 |
| Comp. Ex. 1 | 140 | 30 | 17.7 | 15.9 | 0.920 | 17.7 | 2.3 |

*1: unit: kg/cm²g
*2: unit: kg/mmol-Zr.hr.
(a): dimethylsilylene(2-methyl-4,5-benzo-1-indenyl)(2,7-di-t-butyl-9-fluorenyl)zirconium dichloride
(b): dimethylsilylene(2-methyl-4,5-benzo-1-indenyl)(9-fluorenyl)zirconium dichloride
(c): dimethylsilylene(2,6-dimethyl-4,5-benzo-1-indenyl)(2,7-di-t-)butyl-9-fluorenyl)zirconium dichloride
(d): dimethylsilylene(2,7-dimethyl-4,5-(2-methyl-benzo)-1-indenyl)(2,7-di-t-butyl-9-fluorenyl)zirconium dichloride
(e): dimethylsilylene(2-n-propyl-4-(9-phenanthryl)-1-indenyl)(9-fluorenyl)zirconium dichloride
(x): dimethylsilylene(1-indenyl)(9-fluorenyl)zirconium dichloride Example 8

To a 2 liter glass reactor thoroughly purged with nitrogen, 400 ml of purified toluene was introduced, Then, ethylene (100 l/hr) was passed through the system, and the system was maintained at 70° C. for 10 minutes with stirring at 800 rpm. To the system was then added 4 ml of a toluene solution containing 0.80 mg·atom (in terms of aluminum atom) off methylaluminoxane and 0.0008 mg-atom (in terms of zirconium atom) of ethylene(9-fluorenyl)(2-methyl-1-indenyl) zirconium dichloride. After polymerization was carried out at 80° C. Under atmospheric pressure for 5 minutes, a small amount of isopropanol was added to terminate the polymerization. After the reaction, the reaction solution was introduced into 400 ml of a methanol solution of dilute hydrochloric acid. Then, the catalyst residue was removed, and the resulting polymer was dried overnight under reduced pressure.

The yield of the ethylene homopolymer obtained was 7.53 g. The results are set forth in Table 2.

Example 9

Polymerization of ethylene was carried out in the same manner as in Example 8 except that dimethylsilylene(9-fluorenyl)(2-methyl-1-indenyl)zirconium dichloride synthesized in Preparation Example 7 was used in place of ethylene (9-fluorenyl)(2-methyl-1-indenyl)zirconium dichloride.

The yield of the ethylene homopolymer obtained was 6.00 g. The results are set forth in Table 2.

Example 10

Polymerization of ethylene was carried out in the same manner as in Example 8 except that diphenylsilylene(9-fluorenyl)(2-methyl-1-indenyl)zirconium dichloride synthesized in Preparation Example 6 was used in place of ethylene (9-fluorenyl)(2-methyl-1-indenyl)zirconium dichloride.

The yield of the ethylene homopolymer obtained was 0.7 g. The results are set forth in Table 2.

Example 11

Polymerization of ethylene was carried out in the same manner as in Example 8 except that dimethylsilylene(9-fluorenyl)(2-methyl-4-phenyl-1-indenyl)zirconium dichloride synthesized in Preparation Example 10 was used in place of ethylene (9-fluorenyl)(2-methyl-1-indenyl) zirconium dichloride.

The yield of the ethylene homopolymer obtained was 1.38 g. The results are set forth in Table 2.

Comparative Example 2

Polymerization of ethylene was carried out in the same manner as in Example 8 except that ethylene(9-fluorenyl) (1-indenyl)zirconium dichloride synthesized in Preparation Example 9 was used in place of ethylene(9-fluorenyl)(2-methyl-1-indenyl)zirconium dichloride.

The yield of the ethylene homopolymer obtained was 0.85 g. The results are set forth in Table 2.

Comparative Example 3

Polymerization of ethylene was carried out in the same manner as in Example 8 except that dimethylsilylene(9-fluorenyl)(1-indenyl)zirconium dichloride synthesized in accordance with the process described in Japanese Patent Laid-Open Publication No. 345793/1993 was used in place of ethylene(9-fluorenyl)(2-methyl-1-indenyl)zirconium dichloride.

The yield of the ethylene homopolymer obtained was 0.98 g. The results are set forth in Table 2.

TABLE 2

| | Transition metal compound | Yield (g) | Polymerization activity *1 | Intrinsic viscosity (dl/g) |
|---|---|---|---|---|
| Ex. 8 | (f) | 7.53 | 113 | 4.98 |
| Ex. 9 | (g) | 6.00 | 90.0 | 5.15 |
| Ex. 10 | (h) | 0.70 | 10.5 | 7.22 |
| Ex. 11 | (k) | 1.38 | 20.7 | 4.83 |
| Comp. Ex. 2 | (i) | 0.85 | 12.8 | 4.02 |
| Comp. Ex. 3 | (j) | 0.98 | 14.7 | 3.10 |

*1: kg/mmol-Zr.hr
(f): ethylene(9-fluorenyl)(2-methyl-1-indenyl)zirconium dichloride
(g): dimethylsilylene(9-fluorenyl)(2-methyl-1-indenyl)zirconium dichloride
(h): diphenylsilylene(9-fluorenyl)(2-methyl-1-indenyl)zirconium dichloride
(i): ethylene(9-fluorenyl)(1-indenyl)zirconium dichloride
(j): dimethylsilylene(9-fluorenyl)(1-indenyl)zirconium dichloride
(k): dimethylsilylene(9-fluorenyl)(2-methyl-4-phenyl-1-indenyl)zirconium dichloride

Example 12

To a glass flask thoroughly purged with nitrogen, 0.0087 mg·atom (in terms of zirconium atom) of ethylene(9-fluorenyl)(2-methyl-1-indenyl)zirconium dichloride was introduced. To the flask were added 1.57 ml of a toluene solution of methylaluminoxane (Al: 1.1 mol/l) and 2.76 ml of toluene to obtain a catalyst solution. 0 147 0

To a 2 liter stainless steel autoclave thoroughly purged with nitrogen, 850 ml of hexane and 150 ml of 1-octene were introduced, The temperature of the system was raised to 130° C. Then, 1 mmol of triisobutylaluminum and 1.0 ml (0.002 mmol in terms of Zr) of the catalyst solution prepared above were injected into the system together with ethylene to initiate polymerization. Thereafter, only ethylene was continuously fed so that the total pressure was kept at 30 kg/cm$^2$-G, and the polymerization was carried out at 140° C. for 30 minutes. To the system was then added a small amount of ethanol to terminate the polymerization, and the unreacted ethylene was purged out. The resulting polymer solution was introduced into a large excess of methanol to precipitate a polymer. The polymer was recovered by filtration and dried overnight at 130° C. Under reduced pressure. As a result, 17.1 g or an ethylene-1-octene copolymer was obtained. The results are set forth in Table 3.

Example 13

Polymerization of ethylene and 1-octene was carried out in the same manner as in Example 12 except that dimethylsilylene(9-fluorenyl)(2-methyl-1-indenyl)zirconium dichloride synthesized in Preparation Example 7 was used in place of ethylene(9-fluorenyl)(2-methyl-1-indenyl)zirconium dichloride.

The yield of the ethylene-1-octene copolymer obtained was 15.7 g. The results are set forth in Table 3.

Example 14

Polymerization of ethylene and 1-octene was carried out in the same manner as in Example 12 except that diphenylsilylene(9-fluorenyl)(2-methyl-1-indenyl)zirconium dichloride synthesized in Preparation Example 8 was used in place of ethylene (9-fluorenyl)(2-methyl-1-indenyl)zirconium dichloride.

The yield of the ethylene-1-octene copolymer obtained was 23.5 g. The results are set forth in Table 3.

Example 15

Polymerization of ethylene and 1-octene was carried out in the same manner as in Example 12 except that dimethylsilylene(9-fluorenyl)(2-methyl-4-phenyl-1-indenyl)zirconium dichloride synthesized in Preparation Example 10 was used in place of ethylene (9-fluorenyl)(2-methyl-1-indenyl)zirconium dichloride.

The yield of the ethylene-1-octene copolymer obtained was 21.8 g. The results are set north in Table 3.

Example 16

Polymerization of ethylene and 1-octene was carried out n the same manner as in Example 12 except that ethylene (2-methyl-1-indenyl)(2,7-di-t-butyl-9-fluorenyl))zirconium dichloride synthesized in Preparation Example 11 was used in place of ethylene(9-fluorenyl)(2-methyl-1-indenyl) zirconium dichloride.

The yield or the ethylene-1-octene copolymer obtained was 12.2 g. The results are set forth in Table 3.

Example 17

Polymerization of ethylene and 1-octene was carried out in the same manner as in Example 12 except that dimnethylsilylene(9-fluorenyl)(3-methyl-1-indenyl)zirconium dichloride synthesized in Preparation Example 12 was used in place of ethylene(9fluorenyl)(2-methyl-1-indenyl)zirconium dichloride.

The yield of the ethylene-1-octene copolymer obtained was 26.8 g, The results are set forth in Table 3.

Example 18

Polymerization of ethylene and 1-octene was carried out in the same manner as in Example 12 except that ethylene (9-fluorenyl)(2-methyl-4-phenyl-1-indenyl)zirconium dichloride synthesized in Preparation Example 13 was used in place of ethylene(9-fluorenyl)(2-methyl-1-indenyl) zirconium dichloride.

The yield of the ethylene-1-octene copolymer obtained was 8.4 g. the results are set forth in Table 3.

Example 19

Polymerization of ethylene and 1-octene was carried out in the same manner as in Example 12 except that dimethylsilylene(9-fluorenyl)(2-methyl-4-i-propyl-7-methyl-1-indenyl)zirconium dichloride synthesized in Preparation Example 14 was used in place of ethylene(9-fluorenyl)(2-methyl-1-indenyl)zirconium dichloride.

The yield of the ethylene-1-octene copolymer obtained was 13.1 g. The results are set forth in Table 3.

Example 20

Polymerization of ethylene and 1-octene was carried out in the same manner as in Example 12 except that dimethylsilylene(9-fluorenyl)(2,3-dimethyl-1-indenyl)zirconium dichloride synthesized in Preparation Example 15 was used in place of ethylene(9-fluorenyl)(2-methyl-1-indenyl)zirconium dichloride.

The yield of the ethylene-1-octene copolymer obtained was 27.5 g. The results are set forth in Table 3.

Comparative Example 4

Polymerization of ethylene and 1-octene was carried out in the same manner as in Example 12 except that ethylene (9-fluorenyl)(1-indenyl)zirconium dichloride synthesized in Preparation Example 9 was used in place of ethylene(9-fluorenyl)(2-methyl-1-indenyl)zirconium dichloride.

The yield of the ethylene-1-octene copolymer obtained was 17.7 g. The results are Set forth in Table 3.

TABLE 3

| | Transition metal compound | Yield (g) | Polymerization activity *1 | MFR (g/ 10 min) | Density (g/cm³) | Molecular weight distribution Mw/Mn |
|---|---|---|---|---|---|---|
| Ex. 12 | (f) | 17.1 | 17.1 | 5.82 | 0.922 | 2.0 |
| Ex. 13 | (g) | 15.7 | 15.7 | 0.27 | 0.903 | 2.1 |
| Ex. 14 | (h) | 23.5 | 23.5 | 0.67 | 0.894 | 2.1 |
| Ex. 15 | (k) | 21.8 | 21.8 | 1.95 | 0.887 | 2.0 |
| Ex. 16 | (l) | 12.2 | 12.2 | 3.03 | 0.916 | 2.0 |
| Ex. 17 | (m) | 26.8 | 26.8 | 3.28 | 0.915 | 2.1 |
| Ex. 18 | (n) | 8.4 | 8.4 | 9.5 | 0.694 | 2.1 |
| Ex. 19 | (o) | 13.1 | 13.1 | 0.31 | 0.898 | 2.1 |
| Ex. 20 | (p) | 27.5 | 27.5 | 1.07 | 0.992 | 2.0 |
| Comp. Ex. 4 | (i) | 17.7 | 17.7 | 15.9 | 0.924 | 2.3 |

*1: kg/mmol-Zr.hr
(f): ethylene(9-fluorenyl)(2-methyl-1-indenyl)zirconium dichloride
(g): dimethylsilylene(9-fluorenyl)(2-methyl-1-indenyl)zirconium dichloride
(h): diphenylsilylene(9-fluorenyl)(2-methyl-1-indenyl)zirconium dichloride
(i): ethylene(9-fluorenyl)(1-indenyl)zirconium dichloride
(k): dimethylsilylene(9-fluorenyl)(2-methyl-4-phenyl-1-indenyl)zirconium dichloride
(l): ethylene(2,7-di-t-butyl-9-fluorenyl)(2-methyl-1-indenyl)zirconium dichloride
(m): dimethylsilylene(3-methyl-1-indenyl)(9-fluorenyl)zirconium dichloride
(n): ethylene(2-methyl-4-phenyl-1-indenyl)(9-fluorenyl)zirconium dichloride
(o): dimethylsilylene(2-methyl-4-i-propyl-7-methyl-1-indenyl)(9-fluorenyl)zirconium dichloride
(p): dimethylsilylene(2,3-dimethyl-1-indenyl)(9-fluorenyl)zirconium dichloride

Example 21

To a 2 liter glass reactor thoroughly purged with nitrogen, 400 ml of purified toluene was introduced. Then, propylene was passed through the system at a rate of 100 l/hr, and the system was maintained at 45° C. for 10 minutes with stirring at 800 rpm. Thereafter, 2.88 mg·atom (in terms of aluminum atom) of triisobutylaluminum was added, and 4 ml of a toluene solution containing 3.50 mg·atom (in terms of aluminum atom) of methylaluminoxane and 0.010 mg·atom (in terms of zirconium atom) of ethylene(9-fluorenyl)(2-methyl-1-indenyl)zirconium dichloride was further added. After polymerization was carried out at 50° C. for 15 minutes under atmospheric pressure, a small amount of isopropanol was added to terminate the polymerization. After the reaction, the reaction solution was introduced into 400 ml of a methanol solution of dilute hydrochloric acid. Then, the catalyst residue was removed, and the resulting polymer was dried overnight under reduced pressure.

The yield of the propylene homopolymer obtained was 2.2 g. The results are set forth in Table 4.

Example 22

Polymerization of propylene was carried out in the same manner as n Example 21 except that dimethylsilylene(9-fluorenyl)(2-methyl-1-indenyl)zirconium dichloride synthesized in Preparation Example 7 was used in place of ethylene (9-fluorenyl)(2-methyl-1-indenyl)zirconium dichloride.

The yield of the propylene homopolymer obtained was 3.8 g. The results are set forth in Table 4.

Example 23

Polymerization of propylene was carried out in the same manner as in Example 21 except that diphenylsilylene(9-fluorenyl)(2-methyl-1-indenyl)zirconium dichloride synthesized in Preparation Example 8 was used in place of ethylene (9-fluorenyl)(2-methyl-1-indenyl)zirconium dichloride.

The yield of the propylene homopolymer obtained was 0.1 g. The results are set forth in Table 4.

Comparative Example 5

Polymerization of propylene was carried out in the same manner as in Example 21 except that ethylene(9-fluorenyl) (1-indenyl)zirconium dichloride synthesized in Preparation Example 9 was used in place of ethylene(9-fluorenyl)(2-methyl-1-indenyl)zirconium dichloride.

However, any propylene polymer was not obtained. The results are set forth In Table 4.

Comparative Example 6

Polymerization of propylene was carried out in the same manner as in Example 21 except that dimethylsilylene(9-fluorenyl)(1-indenyl)zirconium dichloride synthesized in accordance with the process described in Japanese Patent Laid-Open Publication No. 345793/1993 was used in place of ethylene(9-fluorenyl)(2-methyl-1-indenyl)zirconium dichloride.

As a result, trace amounts of a propylene homopolymer were obtained. The results are set forth in Table 4.

TABLE 4

| | Transition metal compound | Yield (g) | Polymerization activity *1 | Intrinsic viscosity (dl/g) | Molecular weight distribution Mw/Mn |
|---|---|---|---|---|---|
| Ex. 21 | (f) | 2.2 | 2.2 | 0.68 | 2.1 |
| Ex. 22 | (g) | 3.8 | 3.6 | 0.97 | 2.0 |
| Ex. 23 | (h) | 0.1 | 0.1 | 0.67 | 1.9 |
| Comp. Ex. 5 | (i) | 0 | 0 | — | — |
| Comp. Ex. 6 | (j) | <0.1 | <0.1 | unmeasurable | — |

*1: kg/mmol-Zr.hr
(f): ethylene(9-fluorenyl)(2-methyl-1-indenyl)zirconium dichloride
(g): dimethylsilylene(9-fluorenyl)(2-methyl-1-indenyl)zirconium dichloride
(h): diphenylsilylene(9-fluorenyl)(2-methyl-1-indenyl)zirconium dichloride
(i): ethylene(9-fluorenyl)(1-indenyl)zirconium dichloride
(j): dimethylsilylene(9-fluorenyl)(1-indenyl)zirconium dichloride

Example 24

Preparation of Solid Catalyst Component

A suspension of 3.0 g of silica having been dried at 250° C. for 10 hours in 50 ml of toluene was cooled to 0° C. To the suspension, 17.8 ml of toluene solution of methylaluminoxane (Al=1.29 mmol/ml) was dropwise added. During the dropwise addition, the temperature of the system was maintained at 0° C. After the addition, the reaction was proceeded at 0° C. for 30 minutes. Then, the temperature the system was elevated to 95° C. over a period of 30 minutes and, at the temperature, the reaction was further proceeded for 4 hours. After lowering the temperature of the system to 60° C., the supernatant liquid was removed by delectation.

The solid component thus obtained was washed with toluene two times and reslurried with 50 ml of toluene. To the system, 4.9 ml of a toluene solution of dimethylsilylenebis(2,6-dimethyl-4,5-benzo-1-indenyl)(2, 7-di-t-butyl-9-fluorenyl)zirconium dichloride (Zr=0.0233 mmol/ml) was dropwise added at 20° C. over 30 minutes. The temperature of the system was elevated to 80° C. and, at the temperature, the reaction was proceeded for 2 hours. The supernatant liquid was removed and the remained product was washed with hexane two times to obtain a solid catalyst containing 2.1 mg/g of zirconium.

Preparation of Prepolymerized Catalyst 4 g of the solid catalyst obtained above was resuspended in 200 mol of hexane. To the system, 5.0 ml of a decane solution of triisobutylaluminum (1 mmol/ml) and 0.35 g of 1-hexene were added and, in the system, ethylene was prepolymerized at 35° C. for 2 hours to obtain a prepolymerized catalyst containing, per 1 g of the solid catalyst, 2.0 mg of zirconium and 3 g of polyethylene.

Polymerization

To a 2 liter stainless steel autoclave thoroughly purged with nitrogen, 1 liter of purified and dehydrated hexane was introduced. Then, the autoclave was purged with ethylene. After elevating the temperature of the system to 60° C., 1.5 mmol of triisobutylaluminum, 20 ml of 1-hexene and 0.23 mg, in terms of zirconium atom, of the prepolymerized catalyst thus prepared were introduced.

Thereafter, ethylene was fed so that the total pressure became 8 kg/cm²-G, and the polymerization was carried out for 1.5 hours with keeping the total pressure at 8 g/cm²-G.

After finishing the prepolymerization, the polymer was recovered by filtration and dried overnight at 80° C. As a result, 323 g of an ethylene-;-hexene copolymer having Mw/Mn of 1.99

Example 25

Polymerization was carried out in the same manner as in Example 24 except that ethylene was changed to a mixed gas of ethylene and hydrogen (hydrogen content: 0.1 mol %) As a result, 120 g of an ethylene/1-hexene copolymer having an intrinsic viscosity (η) of 1.29 dl/g and a density of 0.948 g/cm³ was obtained.

Example 26

Polymerization was carried out in the same manner as in Example 24 except that 1-hexene was not added. As a result, 202 g of an ethylene polymer having Mw/Mn of 2.20 was obtained.

Example 27

Polymerization was carried out in the same manner as in Example 26 except that ethylene was changed to a mixed gas of ethylene and hydrogen (hydrogen content: 0.46 mol %). As a result, 108 g of an ethylene polymer having an intrinsic viscosity (η) of 1.59 dl/g and a density of 0.973 g/cm³ was obtained.

What is claimed is:

1. A process for preparing an olefin polymer, comprising homopolymerizing an olefin or copolymerizing two or more kinds of olefins in the presence of an olefin polymerization catalyst selected from the group consisting of (1) an olefin polymerization catalyst comprising:
  (A-1) a Group IVB transition metal compound represented by the following formula (I),
  (B) (B-1) an organoaluminum oxy-compound, and/or
    (B-2) a compound which reacts with the transition metal compound (A-1) to form an ion pair, and, optionally,
  (C) an organoaluminum compound;

(2) an olefin polymerization catalyst comprising:
  a fine particle carrier,
  (A-1) a Group IVB transition metal compound represented by the following formula (I),
  (B) (B-1) an organoaluminum oxy-compound, and/or
    (B-2) a compound which reacts with the transition metal compound (A-1) to form an ion pair and, optionally,
  (C) an organoaluminum compound; and (3) an olefin polymerization catalyst formed by prepolymerizing an olefin onto: a solid catalyst component which comprises:
  (A-1) a Group IVB transition metal compound represented by the following formula (I), and
  (B) (B-1) an organoaluminum oxy-compound, and/or
    (B-2) a compound which reacts with the transition metal compound (A-1) to form an ion pair, said components (A-1) and (B) being supported on a fine particle carrier, and, optionally,
  (C) an organoaluminum compound;

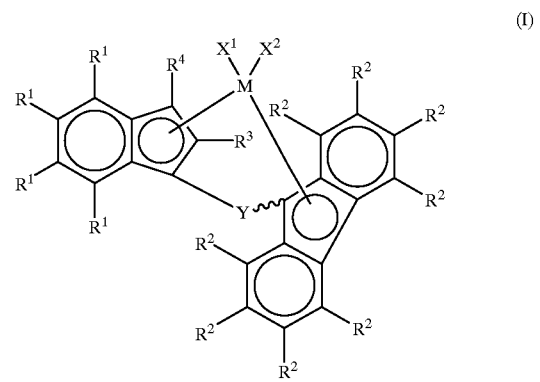

wherein M is a transition metal atom of Group IVB of the periodic table, $R^1$'s may be the same or different, and, are selected from the group consisting of hydrogen atom, halogen atom, and alkyl group of 1 to 10 carbon atoms, and at least two adjacent $R^1$ groups form an aromatic ring or an aliphatic ring together with carbon atoms to which said at least two $R^1$ groups are bonded, said rings formed by said $R^1$ groups having 4 to 20 carbon atoms, as a whole;

$R^2$'s may be the same or different, and are selected from the group consisting of hydrogen atom, halogen atom, alkyl group of 1 to 10 carbon atoms, aryl group of 6 to 20 carbon atoms, alkenyl group of 2 to 10 carbon atoms, arylalkyl group of 7 to 40 carbon atoms, arylalkenyl group of 8 to 40 carbon atoms, alkylaryl group of 7 to 40 carbon atoms, silicon-containing group, oxygen-containing group, sulfur-containing group, nitrogen-containing group and phosphorus-containing group;

at least one of $R^3$ and $R^4$ is a methyl group and the other is selected from the group consisting of hydrogen atom, halogen atom, alkyl group of 1 to 10 carbon atoms, aryl group of 6 to 20 carbon atoms, alkenyl group of 2 to 10 carbon atoms, arylalkyl group of 7 to 40 carbon atoms, arylalkenyl group of 8 to 40 carbon atoms, alkylaryl group of 7 to 40 carbon atoms, silicon-containing group, oxygen-containing group, sulfur-containing group, nitrogen-containing group and phosphorus-containing group;

$X^1$ and $X^2$ may be the same as or different from each other and are selected from the group consisting of hydrogen atom, halogen atom, hydrocarbon group of 1 to 20 carbon atoms, halogenated hydrocarbon group of 1 to 20 carbon atoms, oxygen-containing group, and sulfur-containing group; and Y represents divalent hydrocarbon group of 1 to 20 carbon atoms, divalent halogenated hydrocarbon group of 1 to 20 carbon atoms, divalent silicon-containing group, divalent germanium-containing group, divalent tin-containing group, —O—, —CO—, —S—, —SO—, —SO$_2$—, —NR$^5$—, —P(R$^5$)—, —P(O)(R$^5$)—, —BR$^5$— or —AlR$^5$—, wherein, R$^5$ is a hydrogen atom, a halogen atom, a hydrocarbon group of 1 to 20 carbon atoms or a halogenated hydrocarbon group of 1 to 20 carbon atoms.

2. The olefin polymerization process according to claim 1, wherein the homo- or co-polymerization is carried out in the presence of the olefin polymerization catalyst (1), comprising (A-1) said transition metal compound of formula (I), (B) (B-1) an organoaluminum oxy-compound, and/or (B-2) a compound which reacts with the transition metal compound (A-1) to form an ion pair, and optionally (C) an organoaluminum compound.

3. The olefin polymerization process according to claim 1, wherein the homo- or co-polymerization is carried in the presence of the olefin polymerization catalyst (2) which comprises:

(A-1) said transition metal compound of formula (I), and (B) (B-1) an organoaluminum oxy-compound, and/or (B-2) a compound which reacts with the transition metal compound (A-1) to form an ion pair; said components (A-1) and (B) being supported on the fine particle carrier, and optionally (C) an organoaluminum compound.

4. The olefin polymerization process according to claim 1, wherein the transition metal compound (A-1) comprises dimethylsilylene (2-methyl-4,5-benzo-1-indenyl)(2,7-di-t-butyl-9-fluorenyl)zirconium dichloride.

5. The olefin polymerization process according to claim 1, wherein the transition metal compound (A-1) comprises dimethylsilylene (2-methyl-4,5-benzo-1-indenyl)(9-fluorenyl)zirconium dichloride.

6. The olefin polymerization process according to claim 1, wherein the transition metal compound (A-1) comprises dimethylsilylene (2,6-dimethyl-4,5-benzo-1-indenyl)(2,7-di-t-butyl-9-fluorenyl)zirconium dichloride.

7. The olefin polymerization process according to claim 1, wherein the transition metal compound (A-1) comprises dimethylsilylene (2,7-dimethyl-4,5-(2-methyl-benzo)-1-indenyl)(2,7-di-t-butyl-9-fluorenyl)zirconium dichloride.

8. The olefin polymerization process according to claim 1, which comprises homopolymerizing ethylene.

9. The olefin polymerization process according to claim 1, which comprises copolymerizing ethylene and at least one α-olefin of 3 to 20 carbon atoms.

10. The olefin polymerization process according to claim 1, which comprises homopolymerizing propylene.

11. The olefin polymerization process according to claim 1, which comprises copolymerizing propylene with at least one of ethylene and α-olefin of from 4 to 20 carbon atoms.

* * * * *